US010385411B2

(12) United States Patent
Huang

(10) Patent No.: US 10,385,411 B2
(45) Date of Patent: *Aug. 20, 2019

(54) METHODS FOR DETERMINING RESISTANCE OR SUSCEPTIBILITY TO HIV ENTRY INHIBITORS

(71) Applicant: Monogram Biosciences, Inc., South San Francisco, CA (US)

(72) Inventor: Wei Huang, Foster City, CA (US)

(73) Assignee: Monogram BioSciences, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/362,141

(22) Filed: Nov. 28, 2016

(65) Prior Publication Data

US 2017/0145523 A1 May 25, 2017

Related U.S. Application Data

(62) Division of application No. 11/921,751, filed as application No. PCT/US2006/022071 on Jun. 6, 2006, now Pat. No. 9,506,121.

(60) Provisional application No. 60/765,333, filed on Feb. 4, 2006, provisional application No. 60/688,170, filed on Jun. 6, 2005.

(51) Int. Cl.
*C12Q 1/70* (2006.01)
(52) U.S. Cl.
CPC ....... *C12Q 1/703* (2013.01); *C12Q 2600/156* (2013.01); *C12Q 2600/158* (2013.01)
(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,800,159 A | 1/1989 | Mullis et al. |
| 4,965,188 A | 10/1990 | Mullis et al. |
| 5,631,734 A | 5/1997 | Stern et al. |
| 5,723,320 A | 3/1998 | Dehlinger et al. |
| 5,744,305 A | 4/1998 | Fodor et al. |
| 5,834,758 A | 11/1998 | Trulson et al. |
| 5,837,464 A | 11/1998 | Capon et al. |
| 5,837,832 A | 11/1998 | Chee et al. |
| 5,919,523 A | 7/1999 | Sundberg et al. |
| 6,022,963 A | 2/2000 | Mcgall et al. |
| 6,040,138 A | 3/2000 | Lockhart et al. |
| 6,141,096 A | 10/2000 | Stern et al. |
| 6,156,501 A | 12/2000 | Mcgall et al. |
| 6,168,948 B1 | 1/2001 | Anderson et al. |
| 6,197,506 B1 | 3/2001 | Fodor et al. |
| 6,225,625 B1 | 5/2001 | Pirrung et al. |
| 6,261,776 B1 | 7/2001 | Pirrung et al. |
| 6,284,465 B1 | 9/2001 | Wolber |
| 6,287,850 B1 | 9/2001 | Besemer et al. |
| 6,291,183 B1 | 9/2001 | Pirrung et al. |
| 6,308,170 B1 | 10/2001 | Balaban |
| 6,309,823 B1 | 10/2001 | Cronin et al. |
| 6,333,155 B1 | 12/2001 | Lockhart et al. |
| 6,342,355 B1 | 1/2002 | Hacia et al. |
| 6,355,432 B1 | 3/2002 | Fodor et al. |
| 6,379,895 B1 | 4/2002 | Fodor |
| 6,391,550 B1 | 5/2002 | Lockhart et al. |
| 6,410,229 B1 | 6/2002 | Lockhart et al. |
| 6,451,536 B1 | 9/2002 | Fodor et al. |
| 6,489,114 B2 | 12/2002 | Laayoun et al. |
| 6,505,125 B1 | 1/2003 | Ho |
| 6,548,257 B2 | 4/2003 | Lockhart et al. |
| 6,551,784 B2 | 4/2003 | Fodor et al. |
| 6,617,112 B2 | 9/2003 | Beals |
| 6,670,124 B1 | 12/2003 | Chow et al. |
| 6,733,188 B2 | 5/2004 | Brezina et al. |
| 7,097,970 B2 | 8/2006 | Petropoulos et al. |
| 7,247,439 B1 | 7/2007 | Richman et al. |

OTHER PUBLICATIONS

HIV/AIDS Surveillance Report 11 (1); Centers for Disease Control &Prevention, 1999.
Guidelines for the Use of Antiretroviral Agents in HIV-Infected Adults and Adolescents, Department of Health and Human Services (DHHS), Henry Kaiser Family Foundation, Jan. 28, 2000.
"AIDS Epidemic Update", UNAIDS/World Health Organization, Dec. 1999.
"HIV-1 vector pNL4-3", GenBank Accession No. AF324493, complete sequence, 1986.
U.S. Appl. No. 11/921,751 , "Final Office Action", dated Dec. 10, 2015, 7 pages.
U.S. Appl. No. 11/921,751 , "Final Office Action", dated Feb. 27, 2014, 9 pages.
U.S. Appl. No. 11/921,751 , "Non Final Office Action", dated Sep. 25, 2014, 9 pages.
U.S. Appl. No. 11/921,751 , "Non-Final Office Action", dated Apr. 10, 2015, 12 pages.
U.S. Appl. No. 11/921,751 , "Notice of Allowance", dated Jul. 18, 2016, 7 pages.

(Continued)

*Primary Examiner* — Nicole Kinsey White
(74) *Attorney, Agent, or Firm* — Kilpatrick Townsend & Stockton LLP

(57) ABSTRACT

The invention provides a method for determining whether a human immunodeficiency virus is likely to be more resistant to a viral entry inhibitor than a reference HIV. In certain aspects, the methods comprise comparing the length of one or more variable regions of an envelope protein of the HIV or a number of glycosylation sites on the envelope protein of the HIV to a length of one or more corresponding variable regions of an envelope protein of the reference HIV or a number of glycosylation sites on the envelope protein of the reference HIV, wherein the HIV is likely to be more resistant to the CD4 binding site entry inhibitor than the reference HIV when the HIV has longer variable regions than the reference HIV or the HIV has more glycosylation sites than the reference HIV.

Figure 2A:
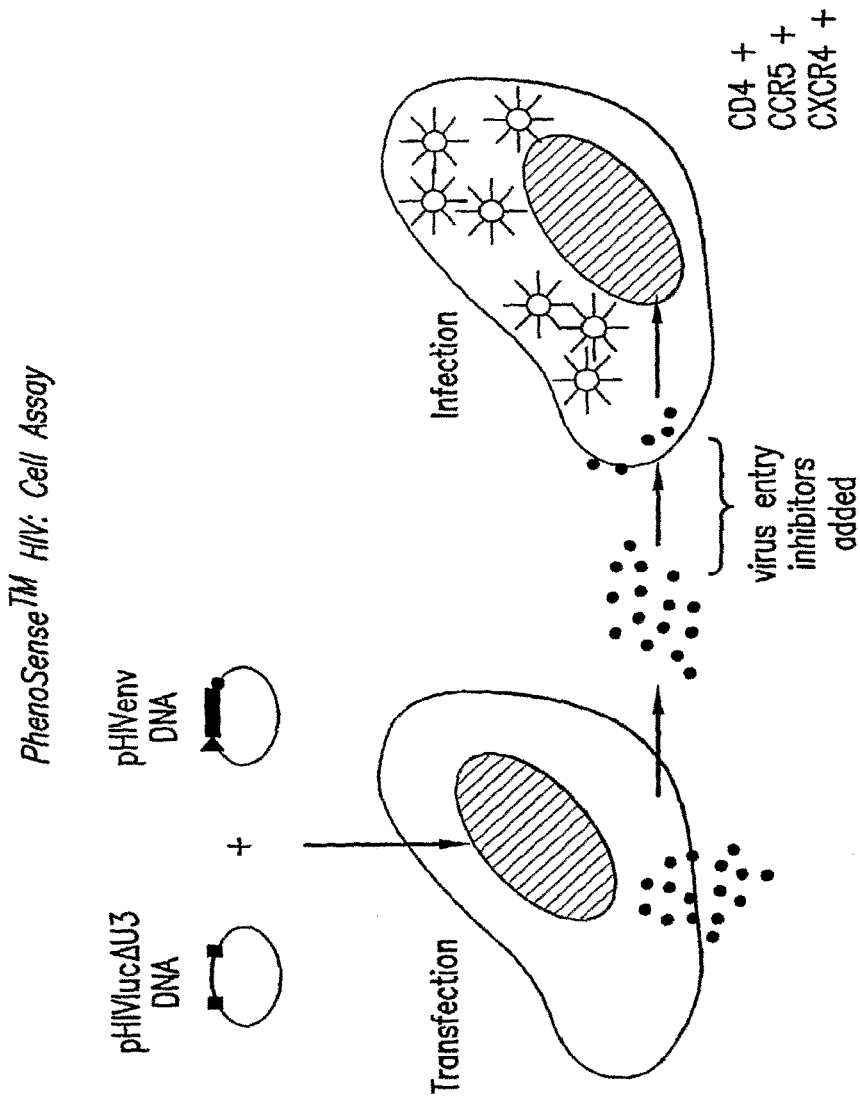

6 Claims, 16 Drawing Sheets
Specification includes a Sequence Listing.

(56) References Cited

OTHER PUBLICATIONS

U.S. Appl. No. 11/921,751 , "Office action", dated Sep. 26, 2011, 6 pages.
Abravaya et al., "Detection of point mutations with a modified ligase chain reaction (Gap-LCR)", 1995, Nucleic Acids Research, 24(4):675-682.
Adachi et al., "Production of acquired immunodeficiency syndrome-associated retrovirus in human and nonhuman cells transfected with an infectious molecular clone", 1986, Journal of Virology, 59(2):284-291.
Alkhatib et al., "cc CKR5: A RANTES, MIP-1 a, MIP-113 receptor as a fusion cofactor for macrophage-tropic HIV-1", 1996, Science, 272:1955-1958.
Allaway et al., "Synergistic Inhibition of HIV-1 Envelope-Mediated Cell Fusion by CD4-based molecules in combination with antibodies to gp120 or gp41", 1993, AIDS Res. Hum. Retroviruses, 9:581-287.
Altschul et al., "Basic local alignment search tool", 1990, J Mol Biol., 215(3):403-410.
Altschul et al., "Gapped BLAST and PSI-BLAST: a new generation of protein database search programs", 1997, Nucleic Acids Res., 25(17):3389-402.
Ausubel et al., Current Protocols in Molecular Biology, 2001.
Baba et al., "A small-molecule, nonpeptide CCR5 antagonist with highly potent and selective anti-HIV-1 activity", 1999, Proc. Natl. Acad. Sci. USA, 96: 5698-5703.
Barany , "Genetic disease detection and DNA amplification using cloned thermostable ligase", 1991, Proc Natl Acad Sci U S A. 88(1):189-93.
Barnes , "PCR amplification of up to 35-kb DNA with high fidelity and high yield from II bacteriophage templates", 1994, Proc. Natl. Acad. Sci. USA, 91:2216-2220.
Baxter et al., "A pilot study of the short term effects of antiretroviral management based on plasma genotypic antiretroviral resistance testing in patients failing antiretroviral therapy", 2000, AIDS. 14(9):F83-93.
Bernard et al., "Cell killing by the F plasmid CcdB protein involves poisoning of DNA-topoisomerase II complexes", 1992, J. Mol. Bio., 226:735-745.
Bernard et al., "The F plasmid CcdB protein induces efficient ATP-dependent DNA cleavage by gyrase", 1993, J. Mol. Biol. 234:534-541.
Bleul et al., "The lymphocyte chemoattractant SDF-1 is a ligand for LESTR/fusin and blocks HIV-1 entry", 1996, Nature, 382:829-33.
Bridger et al., "Synthesis and structure-activity relationships of phenylenebis(methylene)-linked bis-azamacrocycles that inhibit HIV-1 and HIV-2 replication by antagonism of the chemokine receptor CXCR4", 1999, J. Med. Chem., 42:3971-3981.
Coffin et al., "Retroviruses", 1997, Cold Spring Harbor Laboratory Press, New York, NY.
Coffin , "HIV population dynamics in vivo: implications for genetic variation, pathogenesis and therapy", 1995, Science, 267:483-489.
Colonno et al., "Identification of 150Las the Signature Atazanavir (ATV)-Resistance Mutation in Treatment-Naive HIV-1-Infected Patients Receiving ATV-Containing Regimens", 2004, Journal of Infectious Diseases, 1(189):802-1810.
Cotton et al., "Reactivity of cytosine and thymine in single-base-pair mismatches with hydroxylamine and osmium tetroxide and its application to the study of mutations", 1988, Proc. Natl. Acad. Sci. USA, 85:4397-4401.
Eisenberg et al., "Analysis of Membrane and Surface Protein Sequences with the Hydrophobic Moment Plot", 1984, Journal of Molecular Biology, 179(1):125-142.
Faham et al., "A Novel In Vivo Method to Detect DNA Sequence Variation", 1995, Genome Research, 5:474-482.
Fischer et al., "DNA fragments differing by single base-pair substitutions are separated in denaturing gradient gels: correspondence with melting theory", 1983, Proc. Natl. Acad. Sci. USA, 80:1579-1583.

Gerdes et al., "The hok killer gene family in gram-negative bacteria", 1990, The New Biologist, 2:946-956.
Gupta et al., "Combinations of mutations in the connection domain of human immunodeficiency virus type 1 reverse transcriptase: assessing the impact on nucleoside and nonnucleoside reverse transcriptase inhibitor resistance", 2010, Antimicrobial Agents and Chemotherapy, 54(5):1973-80.
Hammond et al., "Mutations in Retroviral Genes Associated with Drug Resistance", Los Alamos National Laboratory III-36, 1999, pp. 542-591.
Hertogs et al., "A Rapid Method for Simultaneous Detection of Phenotypic Resistance to Inhibitors of Protease and Reverse Transcriptase in Recombinant Human Immunodeficiency Virus Type 1 Isolates from Patients Treated with Antiretroviral Drugs", 1998, Antimicrob. Agents Chemo., 42(2):269-276.
Hirsch et al., "Antiretroviral Drug Resistance Testing in Adult HIV-1 Infection: 2008 Recommendations of an International AIDS Society-USA Panel", 2008, Clinical Infectious Diseases, 47:266-285.
Hwang et al., "A conditional self-inactivating retrovirus vector that uses a tetracyclineresponsive expression system", 1997, J. Virol., 71:7128-7131.
Japour et al., "Standardized peripheral blood mononuclear cell culture assay for determination of drug susceptibilities of clinical human immunodeficiency virus type 1 isolates", 1993, Antimicrob. Aqents Chemother., 37:1095-1101.
Kan et al., "Antenatal diagnosis of sickle-cell anemia by D.N.A analysis of amniotic-fluid cells", 1978, Lancet, 2:910-912.
Kilby et al., "Potent suppression of HIV-1 replication in humans by T-20, a peptide inhibitor of gp41-mediated virus entry", 1998, Nature Med., 4:1302-1307.
Kroodsma et al., "Detection of Drug Resistance Mutations in the Human Immunodeficiency Virus Type 1 (HIV-1) pol Gene: Differences in Semen and Blood HIV-1 RNA and Proviral DNA", 1994, J. Infectious Diseases, 170:1292-1295.
Kuritzkes et al., "Antiretroviral Activity of the Anti-CD4 Monnoclonal Antibody TNX-355 in Patients Infected With HIV Type 1", 2004, Journal of Infectious Diseases, 189:286-291.
Landegren et al., "A ligase-mediated gene detection technique", 1988, Science, 241:1077-1080.
Mascola et al., "Protection of macaques against vaginal transmission of a pathogenic HIV-1/SIV chimeric virus by passive infusion of neutralizing antibodies", 2000, Nature Med., 6:207-210.
Maxam et al., "Sequencing End-Labeled DNA with Base-Specific Chemical Cleavages", 1980, In: Methods i499-560n Enzymology, Grossman, I., and Moldave, K., eds., 65:499-560.
Mellors et al., "Mutations in HIV-1 Reverse Transcriptase and Protease Associated with Drug Resistance", 1995, Mutations in RT and Protease, iii, 93-105.
Messing et al., "A system for shotgun DNA sequencing", 1981, Nuc. Acids Res., 9:309-321.
Miyoshi et al., "Development of a Self-inactivating Lentivirus Vector", 1998, Journal of Virology, 72(10):8150-8157.
Myers et al., "Detection of Single Base Substitutions by Ribonuclease Cleavage at Mismatches in RNA:DNA Duplexes", 1985, Science, 230(4731):1242-1246.
Naviaux et al., "The pCL Vector System: Rapid Production of Helper-Free, High-Titer, Recombinant Retroviruses", 1996, Journal of Virology, 70:5701-5705.
Nikiforov et al., "Genetic Bit Analysis: a solid phase method for typing single nucleotide polymorphisms", Nucl. Acids Res., vol. 22, No. 20, 1994, pp. 4167-4175.
Orita et al., "Detection of polymorphisms of human DNA by gel electrophoresis as singlestrand conformation polymorphisms", 1989, Proc. Natl. Acad. Sci. USA, 86:2766-2770.
Orita et al., "Rapid and sensitive detection of point mutations and DNA polymorphisms using the polymerase chain reaction", 1989, Genomics, 5:874-879.
Orum et al., "Single base pair mutation analysis by PNA directed PCR clamping", 1993, Nucleic Acids Res., 21(23):5332-5336.

(56) References Cited

OTHER PUBLICATIONS

Pantophlet et al., "Fine mapping of the interaction of neutralizing and nonneutralizing monoclonal antibodies with the CD4 binding site of human immunodeficiency virus type 1 gp120", 2003, Journal of Virology, 77(1):642-658.
PCR Strategies, "Innis, M. et al., eds.", 1995, Academic Press, Inc., San Diego, CA.
Petropoulos et al., "A novel phenotypic drug susceptibility assay for human immunodeficiency virus type 1", 2000, Antimicrob. Agents Chemother, 44(4):920-928.
Piketty et al., "Efficacy of a five-drug combination including ritonavir, saquinavir and efavirenz in patients who failed on a conventional triple-drug regimen: phenotypic resistance to protease inhibitors predicts outcome of therapy", 1999, AIDS, 13(11):F71-F77.
Porter et al., "Cationic liposomes enhance the rate of transduction by a recombinant retroviral vector in vitro and in vivo", 1998, J. Virol., 72:4832-4840.
Reimann et al., "In Vivo Administration of CD4-Specific Monoclonal Antibody: Effect on Provirus Load in Rhesus Monkeys Chronically Infected with the Simian Immunodeficiency Virus of Macaques", 1995, AIDS Res. Hum. Retroviruses, 11:517-25.
Reynard et al., "HIV-1 acute infection env glycomutants designed from 3D model: effects on processing, antigenicity, and neutralization sensitivity", 2004, Virology, 324(1):90-102.
Richman, "Nailing down another HIV target", 1998, Nature Med, 4:1232-1233.
Rimsky et al., "Determinants of human immunodeficiency virus type 1 resistance to gp41-derived inhibitory peptides", 1998, J. Virol., 72:986-993.
Rodriquez et al., "Introduction of HIV drug-resistance testing in clinical practice", 1999, AIDS, 13:1007-1014.
Rusnak et al., "Identification of phosphorylated and glycosylated sites in peptides by chemically targeted proteolysis", 2002, J. Biomol. Tech., 13:228-237.
Russell et al., "Specific-locus test shows ethylnitrosourea to be the most potent mutagen in the mouse", 1979, Proc. Nat. Acad. Sci. USA, 76:818-5819.
Sambrook et al., "Molecular Cloning: A Laboratory Manual", 3rd ed.,vol. 1, 2001, Spring Harbor laboratory New York, NY, pp. v-xx.
Sanger et al., "DNA sequencing with chain-terminating inhibitors", 1977, Proc. Natl. Acad. Sci., 74(12):5463-5467.
Sarkar et al., "The 'Megaprimer' Method of Site-Directed Mutagenesis", 1990, BioTechniques, 8(4):404-407.
Schurmann et al., "SCH D: Antiviral Activity of a CCR5 Receptor Antagonist", 11th Conference on Retroviruses and Opportunistic Infections, Feb. 2004, 8-11.
Shi et al., "A recombinant retroviral system for rapid in vivo analysis of human immunodeficiency virus type 1 susceptibility to reverse transcriptase inhibitors", 1997, Antimicrob. Aqents Chemother., 41:2781-2785.
Southern, "Detection of Specific Sequences Among DNA Fragments Separated by Gel Electrophoresis", 1975, J. Mol. Biol., 98:503-517.
Stephenson, "New Class of Anti-HIV Drugs", 1999, JAMA, 282(21):1994.
Syvanen et al., "A Primer-Guided Nucleotide Incorporation Assay in the Genotyping of Apolipoprotein E", 1990, Genomics, 8(4):684-692.
Thiede et al., "Simple and sensitive detection of mutations in the ras proto-oncogenes using PNA-mediated PCR clamping", 1996, Nucl. Acids Res., 24(5):983-984.
Wagner et al., "Mutation detection using immobilized mismatch binding protein (MutS)", 1995, Nucl. Acids Res., 23(19):3944-3948.
Wei et al., "Antibody neutralization and escape by HIV-1", 2003, Nature, 307-312.
Wild et al., "A synthetic peptide inhibitor of human immunodeficiency virus replication: correlation between solution structure and viral inhibition", 1992, Proc. Natl. Acad. Sci. USA, 89:10537-10541.
Youil et al., "Screening for mutations by enzyme mismatch cleavage with T4 endonuclease VII", 1995, Proc. Natl. Acad. Sci. USA, 92:87-91.
Zennou et al., "Loss of viral fitness associated with multiple Gag and Gag-Pol processing defects in human immunodeficiency virus type 1 variants selected for resistance to protease inhibitors in vivo", 1998, J. Virol., 72:3300-3306.
Ziermann et al., "A Mutation in Human Immunodeficiency Virus Type 1 Protease, N88S, that Causes in Vitro Hypersensitivity to Amprenavir", 2000, Journal of Virology, vol. 74(9):4414-4419.

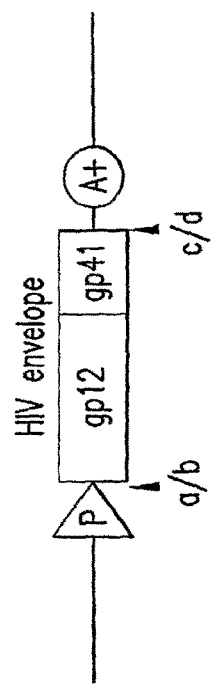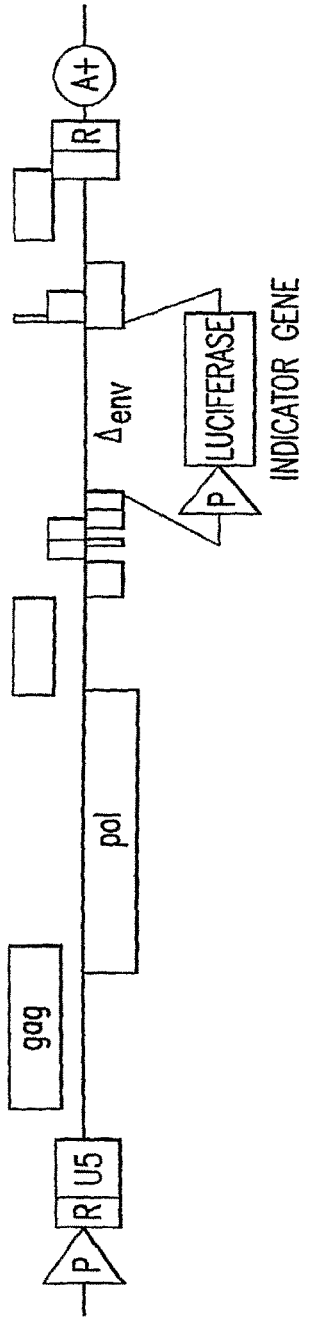

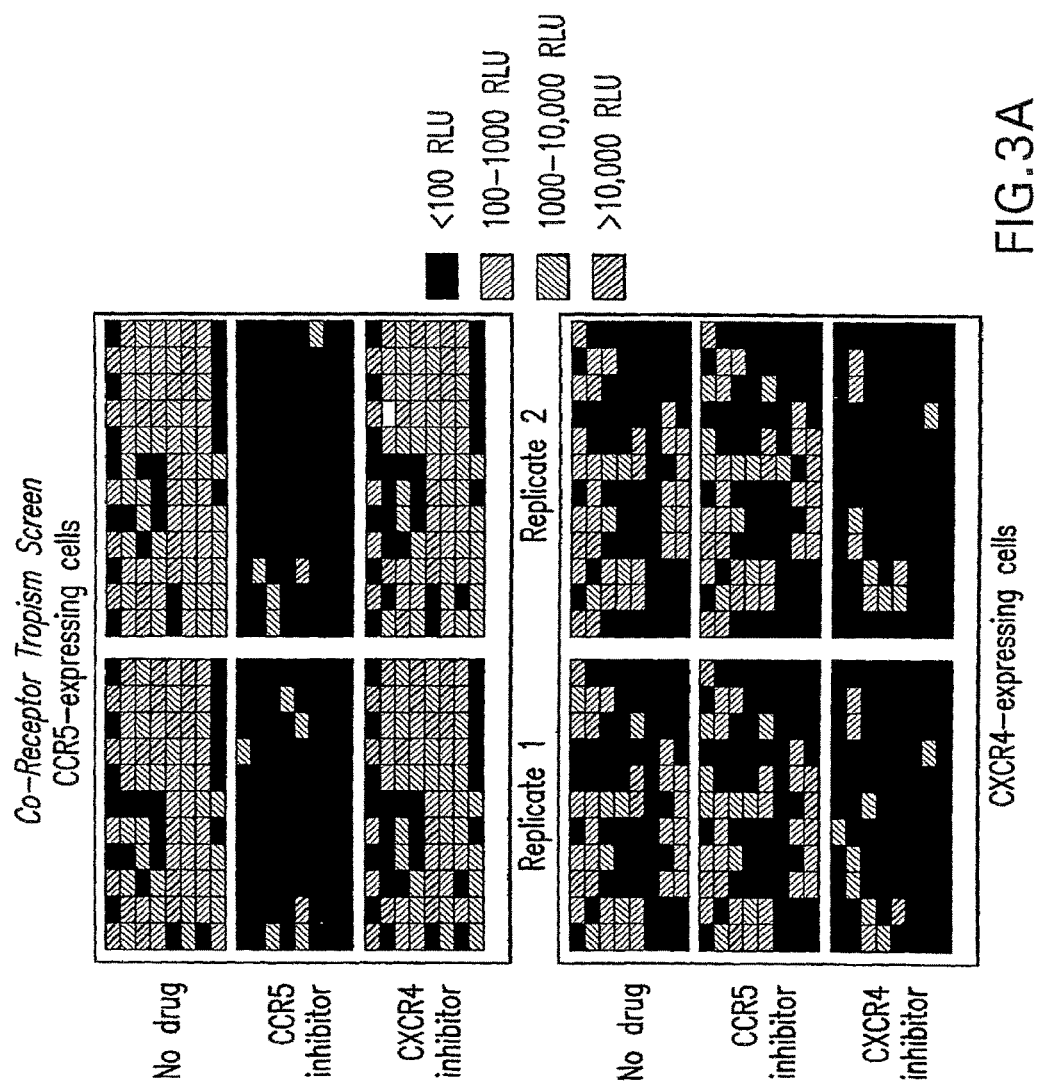

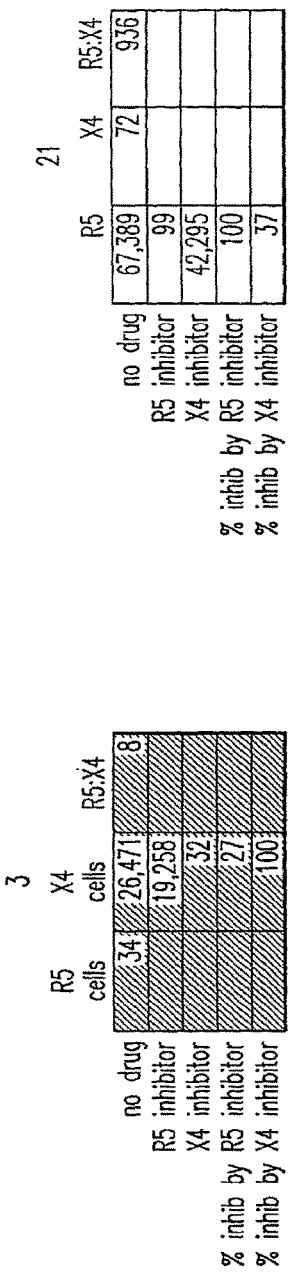
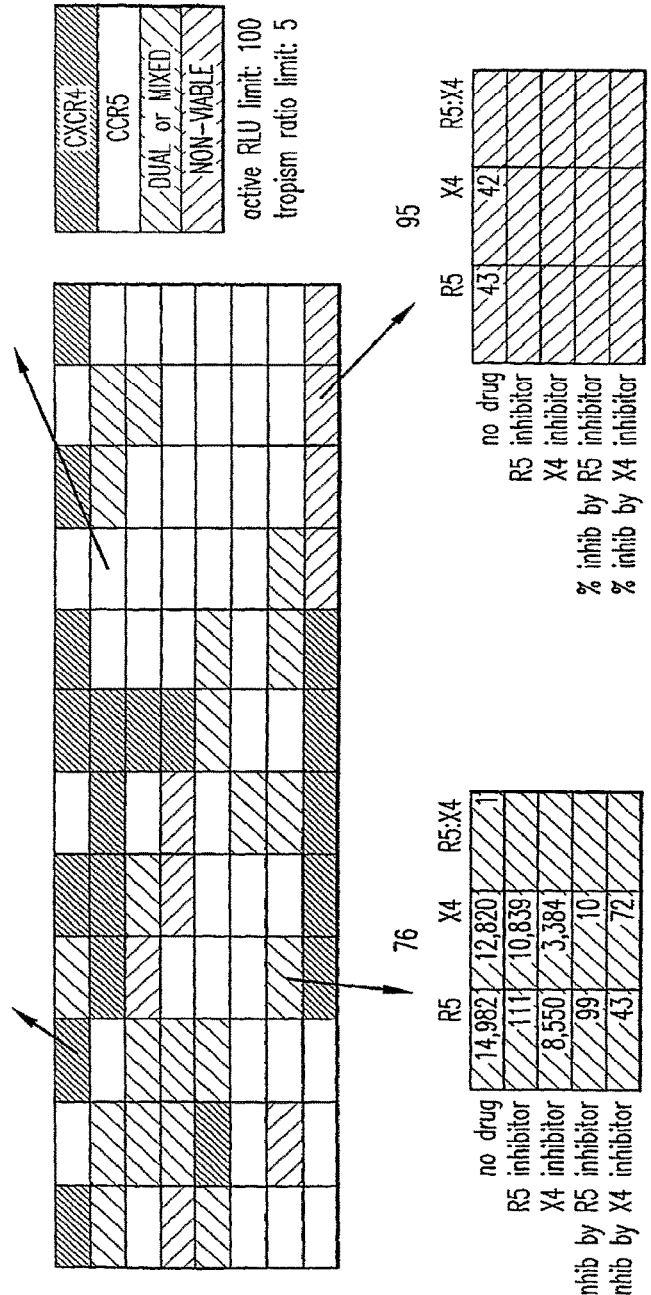
FIG. 3B

| clone | | V1 | |
|---|---|---|---|
| 3  | CTEYNATYSKNTT | ----------------- | TDNTTVNATDTNINDSIWRQVKNCS |
| 20 | CTEYNATYSKNTT | ----------------- | TDNTTVNATDTNINDSIWRQVKNCS |
| 39 | CTEYNATYSKDTT | ----------------- | TDNTTVNATDTNINDSIWRQVKNCS |
| 47 | CTEYNATYSKNTT | ----------------- | TDNTTVNATDTNINDSIWRQVKNCS |
| 48 | CTEYNATYSKNTT | ----------------- | TDNTTVNATDTNINDSIWRQVKNCS |
| 18 | CTEYNATYSKNTT | ----------------- | TDNTTVNATDTNINDSIWRQVKNCS |
| 17 | CTEYNATYSKNTT | ----------------- | TDNTTVNATDTNINDSIWRQVKNCS |
| 35 | CTEYNATYSKNTT | ----------------- | TDNTTVNATDTNINDSIWRQVKNCS |
| 11 | CTEYNATYSKNTT | ----------------- | TDNTTVNATDTNINDSIWRQVKNCS |
| 24 | CTEYNATYSKNTT | ----------------- | TDNTTVNATDTNINDSIWRQVKNCS |
| 5  | CTEYNATYSKNTT | ----------------- | TDNTTVNATDTNINDSIWRQVKNCS |
| 21 | CTEYNATYSKNTT | VSTTSTTTSTTTTSSQTTSATVPNIT | VNPTTININDSIWRQVKNCS |
| 26 | CTEYNATYSKNTT | VSTTSTTTSTTTTSSQTTSATVPNIT | VNPTTININDSIWRQVKNCS |
| 6  | CTEYNATYSKNTT | VSTTSTTTSTTTATSSQTTSATVPNIT | VNPTTININDSIWRQVKNCS |
| 36 | CTEYNATYSKNTT | VSTTSTTTSTTTSPTTTSSQTTSATVT | NTTVNPTTININDSIWRQVKNCS |
| 43 | CTGYNATYSKNTT | VSTTSTTTSPTTTSPTTTTSSQTTSATVT | NTTVNPTTININDSIWRQVKNCS |

Different length in V1 region

FIG.7

More fusion, sensitive to P542, less sensitive to CD4 Ab,

Less fusion, less sensitive

| | | |
|---|---|---|
| 3 | CNTSQLFNSTW--NSTGENDIS-ESNSTEGIITLPC |
| 20 | CNTSQLFNSTW--NSTGENDIS-ESNSTEGIITLPC |
| 39 | CNTSQLFNSTW--NSTGENDIS-ESNSTEGIITLPC |
| 47 | CNTSQLFNSTW--NSTGENDIS-ESNSTEGIIALPC |
| 48 | CNTSQLFNSTW--NSTGENDIS-ESNSTEGIITLPC |
| 18 | CNTSQLFNSTW--NSTGENDIS-ESNSTEGIITLPC |
| 17 | CNTSQLFNSTW--NSTGENDIS-ESNSTEGIITLPC |
| 35 | CNTSQLFNSTW--NSTGENDIS-ESNSTEGIITLPC |
| 11 | CNTSQLFNSTW--NSTGENDIS-ESNSTEGIITLPC |
| 24 | CNTSQLFNSTW--NSTGENGIS-ESNSTEGIITLPC |
| 5  | CNTSQLFNSTW--NSTGENDIS-ESNSTEGIITLPC |
| 21 | CNTSQLFNSTW--NSTEENDIS-ESNSTRGNITLPC |
| 26 | CNTSQLFNSTW--NSTEENDIS-ESNSTRGNITLPC |
| 6  | CNTSQLFNSTW--NSTEENDIS-ESNSTRGNITLPC |
| 36 | CNTSQLFNSTWLGNSTLENDTTTESNSTRGNITLPC |
| 43 | CNTSQLFNSTWLGNSTLENDTTTESNSTRGNITLPC |

Sensitive to P542, less sensitive to CD4 Ab, more fusion

Less sensitive to P542, sensitive to CD4 Ab, less fusion

Different in glycosylation sites in V4 region

FIG.8

Different length and glycosylation site in V5 region

V5

More fusion, sensitive to P542, less sensitive to CD4 Ab,

| | |
|---|---|
| 3 | GGNDGS----NNTEIFRPGGGNMK |
| 20 | GGNDGS----NNTEIFRPGGGNMK |
| 39 | GGNDGS----NNTEIFRPGGGNMK |
| 47 | GGNDGS----NNTEIFRPGGGNMK |
| 48 | GGNDGS----NNTEIFRPGGGNMK |
| 18 | GGNDGS----NNTEIFRPGGGNMK |
| 17 | GGNDGS----NNTEIFRPGGGNMK |
| 35 | GGNDGS----NNTEIFRPGGGNMK |
| 11 | GGNDGS----NNTEIFRPGGGNMK |
| 24 | GGNDGS----NNTEIFRPGGGNMK |
| 5 | GGNDGS----NNTEIFRPGGGNMK |

Less fusion, less sensitive to P542, sensitive to CD4 Ab,

| | |
|---|---|
| 21 | GGKKGNETDGNETEIFRPGGGDMR |
| 26 | GGKKGNETDGNETEIFRPGGGDMR |
| 6 | GGKKGNETDGNGTEIFRPGGGDMR |
| 36 | GGKNGNKTDGNETEIFRPGGGNMR |
| 43 | GGKNGNKTDGNETEIFRPGGGNMR |

METHODS FOR DETERMINING RESISTANCE OR SUSCEPTIBILITY TO HIV ENTRY INHIBITORS

1. CROSS REFERENCE TO RELATED APPLICATIONS

This application is a divisional application of U.S. application Ser. No. 11/921,751 (issued as U.S. Pat. No. 9,506,121) filed Dec. 4, 2007, which is a § 371 national phase application of PCT Application No. PCT/US2006/022071 filed Jun. 6, 2006 (expired), which claims priority to U.S. Provisional Application No. 60/765,333 filed Feb. 4, 2006 and U.S. Provisional Application No. 60/688,170 filed Jun. 6, 2005. The contents of each of these applications are hereby incorporated by reference in their entirety.

Throughout this application, various publications are referenced by author and date within the text. Full citations for these publications may be found listed alphabetically at the end of the specification immediately preceding the claims. All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

2. BACKGROUND

Enveloped animal viruses attach to and enter the host cell via the interaction of viral proteins in the virion membrane (envelope proteins) and cell surface proteins (virus receptors). Receptor recognition and binding are mediated by the surface envelope protein. Virus entry is an attractive target for anti-viral treatment; numerous drugs that are designed to block virus attachment or membrane fusion have been or are currently being evaluated in preclinical or clinical studies (Richman, 1998; PhRMA, 1999; Stephenson, 1999). For example, the attachment inhibitor SCH-D, which blocks the interaction between viral membrane proteins and CCR5, is currently being evaluated in clinical studies for its effectiveness as an anti-viral treatment (Shurman, 2004). Other entry inhibitors currently under investigation include UK-427857 (Pfizer), TNX-355 (Tanox Inc.), AMD-070 (AnorMED), Pro 140 (Progenics), FP-21399 (EMD Lexigen), BMS-488043 (Bristol-Myers Squibb), and GSK-873, 140 (GlaxoSmithKline). One entry inhibitor, T-20 (Roche/Trimeris), has been approved for treatment of HIV infection by the United States Food and Drug Administration.

As these drugs continue to be developed and enter the clinic, assays are needed that can rapidly and easily detect the emergence of viruses with reduced susceptibility to entry inhibitors. In particular, methods for determining whether an HIV is resistant to an entry inhibitor, e.g., PRO542, TNX-355, monoclonal antibody B4, monoclonal antibody B12, etc., are needed. These and other unmet needs are provided by the present invention.

3. SUMMARY

In certain aspects, the invention provides a method for determining whether an human immunodeficiency virus ("HIV") is likely to be more resistant to an HIV entry inhibitor than a reference virus. In certain aspects, the invention provides a method for determining whether an HIV is likely to be more resistant to a CD4 binding site entry inhibitor than a reference HIV, comprising comparing the length of one or more variable regions of an envelope protein of the HIV or the number of glycosylation sites on the envelope protein of the HIV to the length of one or more corresponding variable regions of an envelope protein of the reference HIV or the number of glycosylation sites on the envelope protein of the reference HIV, respectively, wherein the HIV is likely to be more resistant to the CD4 binding site entry inhibitor than the reference HIV when the HIV has a longer variable region or regions than the reference HIV and/or the HIV has more glycosylation sites than the reference HIV. In certain embodiments, the CD4 binding site entry inhibitor is selected from the group consisting of PRO542, TNX-355 and monoclonal antibody B12. In certain embodiments, the reference HIV is NL4-3, HXB2, or SF2. In certain embodiments, the HIV has a longer variable region or regions than the reference HIV. In certain embodiments, the HIV has more glycosylation sites than the reference HIV. In certain embodiments, the HIV has a longer variable region or regions and more glycosylation sites than the reference HIV.

In another aspect, the invention provides a method for determining whether an HIV is likely to be more resistant to a CD4-blocking entry inhibitor than a reference HIV, comprising comparing the length of one or more variable regions of an envelope protein of the HIV or the number of glycosylation sites on the envelope protein of the HIV to the length of one or more corresponding variable regions of an envelope protein of the reference HIV or the number of glycosylation sites on the envelope protein of the reference HIV, respectively, wherein the HIV is likely to be more resistant to the CD4 binding site entry inhibitor than the reference HIV when the HIV has shorter variable regions than the reference HIV and/or the HIV has fewer glycosylation sites than the reference HIV. In certain embodiments, the CD4-blocking entry inhibitor is monoclonal antibody B4. In certain embodiments, the reference HIV is NL4-3, HXB2, or SF2. In certain embodiments, the HIV has a shorter variable region or regions than the reference HIV. In certain embodiments, the HIV has fewer glycosylation sites than the reference HIV. In certain embodiments, the HIV has shorter variable regions and fewer glycosylation sites than the reference HIV.

In another aspect, the invention provides a method for determining whether an HIV is likely to exhibit altered susceptibility to an entry inhibitor, comprising detecting, in a nucleic acid encoding an envelope protein of the HIV, a mutation in a codon corresponding to codon 261 of reference HIV strain HXB2, wherein the presence of a mutation in codon 261 indicates that the HIV is likely to be resistant to the entry inhibitor.

In another aspect, the invention provides a method for determining whether an HIV is likely to exhibit altered susceptibility to an entry inhibitor, comprising detecting, in a nucleic acid encoding an envelope protein of the HIV, a mutation in a codon corresponding to codon 117 and at codon 421 of reference HIV strain HXB2, wherein the presence of the mutations indicates that the HIV is likely to be resistant to the entry inhibitor.

In another aspect, the invention provides a method for determining whether an HIV is likely to exhibit altered susceptibility to an entry inhibitor, comprising detecting, in a nucleic acid encoding an envelope protein of the HIV, a mutation in a codon corresponding to codon 121 or codon 298 reference HIV strain HXB2, wherein the presence of the mutations indicates that the HIV is likely to be resistant to the entry inhibitor.

4. BRIEF DESCRIPTION OF THE FIGURES

FIG. 1A: Structure of Envelope Expression and Viral Expression Vectors.

The HIV envelope expression vector (pHIVenv) is modified to accept envelope sequences that have been amplified from subject plasma samples. The designations a/b and c/d, refer to restriction endonuclease sites positioned at the 5' and 3' end of the HIV-1 envelope polyprotein (gp160). The HIV expression vector (pHIVlucΔU3) encodes all HIV proteins except the envelope polyprotein. A portion of the envelope gene has been deleted to accommodate an indicator gene cassette, in this case, firefly luciferase, that is used to monitor the ability of the virus to replicate in the presence or absence of anti-viral drugs. The 3' U3 region has been partially deleted to prevent transcription from the 5' LTR in infected cells. Virus produced in this system is limited to a single round of replication.

FIG. 1B: Cell Based Entry Assay

In this embodiment, drug susceptibility, co-receptor tropism and virus neutralization testing are performed by co-transfecting a host cell with pHIVenv and pHIVlucΔU3. The host cell produces HIV particles that are pseudo-typed with HIV envelope sequences derived from the test virus or subject sample. Virus particles are collected (~48 h) after transfection and are used to infect target cells that express HIV receptors (e.g. CD4) and co-receptors (e.g. CXCR4, CCR5). After infection (~72 h) the target cells are lysed and luciferase activity is measured. HIV must complete one round of replication to successfully infect the target host cell and produce luciferase activity. If the virus is unable to enter the target cell, luciferase activity is diminished. This system can be used to evaluate susceptibility to entry inhibitors, receptor and co-receptor tropism, and virus neutralization.

Figure 2B:
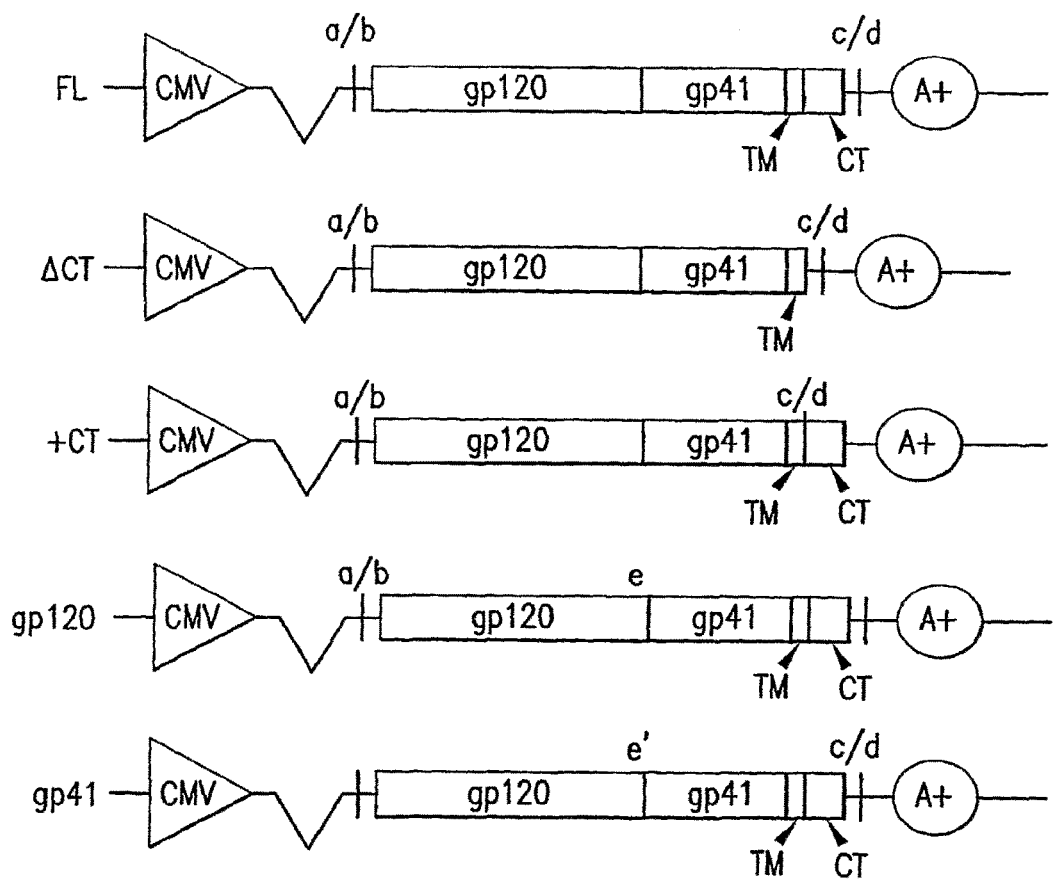

FIG. 2A and FIG. 2B: HIV Envelope Expression Vectors.

HIV envelope sequences are amplified from subject samples and inserted into expression vectors using restriction endonuclease sites (5' a/b and 3'c/d). Envelope transcription is driven by the immediate early gene promoter of human cytomegalovirus (CMV). Envelope RNA is polyadenylated using an simian virus 40 (SV40) polyadenylation signal sequence (A+). An intron located between the CMV promoter and the HIV envelope sequences is designed to increase envelope mRNA levels in transfected cells. FL-express full-length envelope proteins (gp120, gp41); ΔCT-express envelope proteins (gp120, gp21) lacking the C-terminal cytoplasmic tail domain of gp41; +CT-express envelope proteins (gp120, gp41) containing a constant pre-defined gp41 cytoplasmic tail domain; gp120-express gp120 proteins derived from the subject together with a constant pre-defined gp41; and gp41-express a constant pre-defined gp120 together with gp41 proteins derived from the subject.

FIG. 3A: Co-Receptor Tropism Screening Assay.

In this figure, the assay is performed using two cell lines. One cell line expresses CD4 and CCR5 (top six panels). The other cell line expresses CD4 and CXCR4 (bottom six panels). The assay is performed by infecting cells with a large number of recombinant virus stocks derived from cells transfected with pHIVenv and pHIVlucΔU3 vectors. The example shown represents the analysis of 96 viruses formatted in a 96 well plate infections are performed in the absence of drug (no drug), or in the presence of a drug that preferentially inhibits either R5 tropic (CCR inhibitor) or X4 tropic (CXCR4 inhibitor) viruses. Co-receptor tropism is assessed by comparing the amount of luciferase activity produced in each cell type, both in the presence and absence of drug (see FIG. 3B for interpretation of assay results).

FIG. 3B: Determining Co-Receptor Tropism.

In this figure, the results of the assay are interpreted by comparing the ability of each sample virus to infect (produce luciferase activity) in cells expressing CD4/CCR5 (R5 cells) or cells expressing CD4/CXCR4 (X4 cells). The ability of a CCR5 or CXCR4 inhibitor to specifically block infection (inhibit luciferase activity) is also evaluated. X4 tropic viruses infect X4 cells but not R5 cells. Infection of X4 cells is blocked by the CXCR4 inhibitor. R5 tropic viruses infect R5 cells but not X4 cells. Infection of R5 cells is blocked by the CCR5 inhibitor. Dual tropic or X4/R5 mixtures infect X4 and R5 cells. Infection of R5 cells is blocked by the CCR5 inhibitor and infection of X4 cells is blocked by the CXCR4 inhibitor. Non-viable viruses do not replicate in either X4 or R5 cells.

Figure 4A:
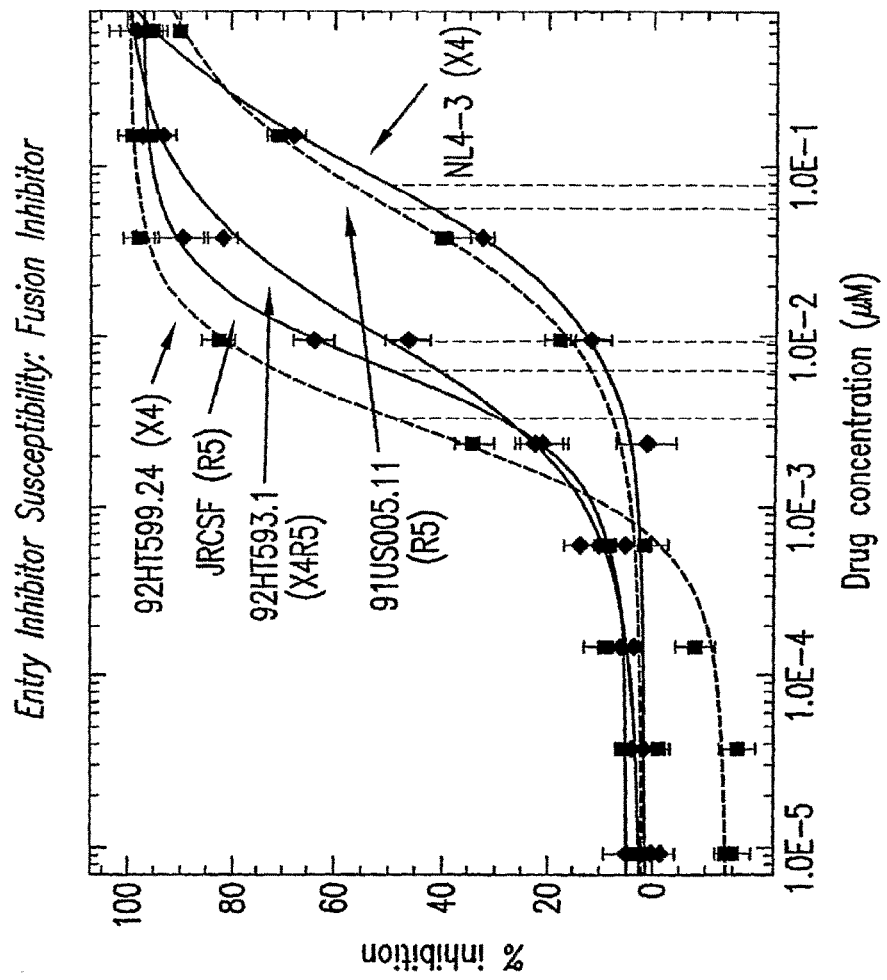

FIG. 4A: Measuring Entry Inhibitor susceptibility: Fusion Inhibitor.

In this figure, susceptibility to the fusion inhibitor T-20 is demonstrated. Cells expressing CD4, CCR5 and CXCR4 were infected in the absence of T-20 and over a wide range of T-20 concentrations α-axis log 10 scale). The percent inhibition of viral replication (y-axis) was determined by comparing the amount of luciferase produced in infected cells in the presence of T-20 to the amount of luciferase produced in the absence of T-20. R5 tropic, X4 tropic and dual tropic viruses were tested. Drug susceptibility is quantified by determining the concentration of T-20 required to inhibit 50% of viral replication ($IC_{50}$, shown as vertical dashed lines). Viruses with lower $IC_{50}$ values are more susceptible to T-20 than viruses with higher $IC_{50}$ values. NL4-3: well-characterized X4 tropic strain JRCSF; well-characterized R5 tropic strain 91US005.11: R5 tropic isolate obtained from the NIH AIDS Research and Reference Reagent Program (ARRRP) 92HT593.1: Dual tropic (X4R5) isolate obtained from the NIH ARRRP.92HT599.24: X4 tropic isolate obtained from the NIH ARRRP.

Figure 4B:
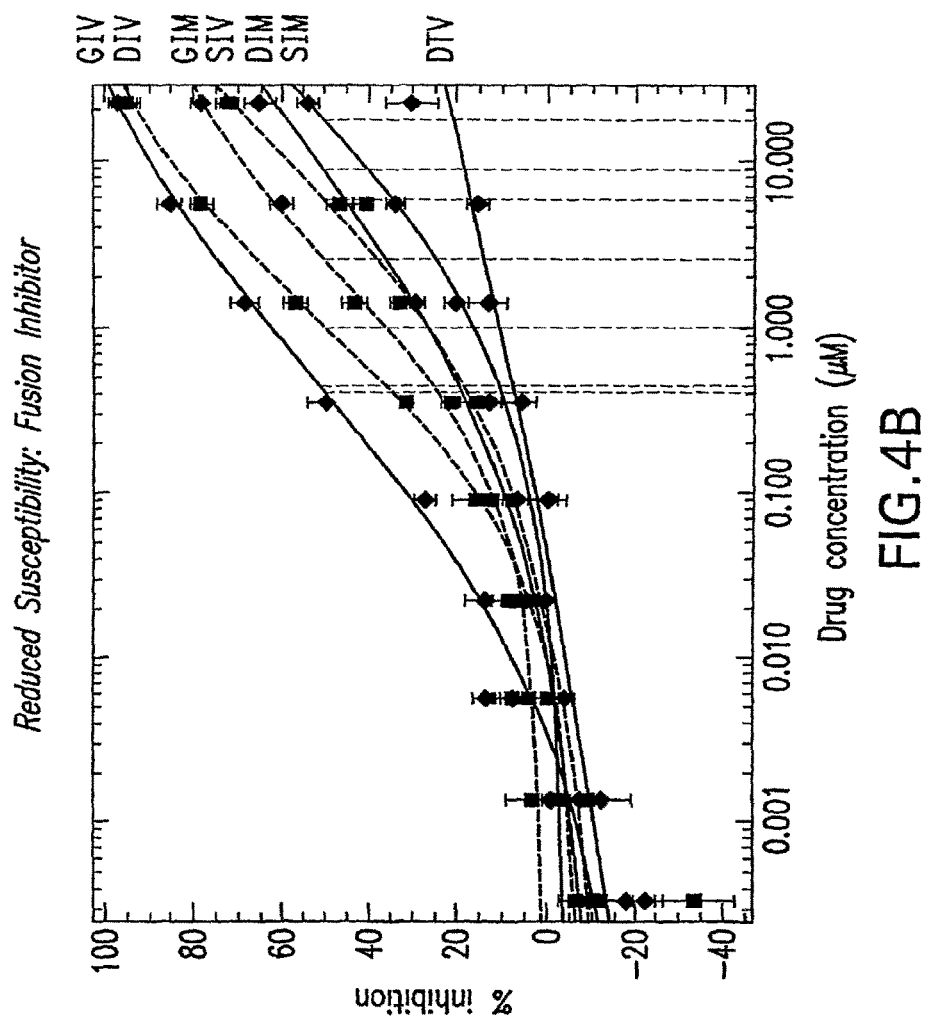

FIG. 4B: Measuring Entry Inhibitor Susceptibility: Drug Resistance Mutations.

In this figure, reduced susceptibility to the fusion inhibitor T-20 conferred by specific drug resistance mutations in the gp41 envelope protein is demonstrated. Cells expressing CD4, CCR5 and CXCR4 were infected in the absence of T-20 and over a wide range of T-20 concentrations (x-axis log 10 scale). The percent inhibition of viral replication (y-axis) was determined by comparing the amount of luciferase produced in infected cells in the presence of T-20 to the amount of luciferase produced in the absence of T-20. Isogenic viruses containing one or two specific mutations in the gp41 transmembrane envelope protein were tested (highlighted in red in the figure legend). Drug susceptibility is quantified by determining the concentration of T-20 required to inhibit 50% of viral replication ($IC_{50}$, shown as vertical dashed lines). Viruses with lower $IC_{50}$ values are more susceptible to T-20 than viruses with higher $IC_{50}$ values. No mutation (wildtype sequence): GIV; Single mutations: GIV, DIM, SIV; Double mutations: DIM, SIM, DTV.

Figure 5:
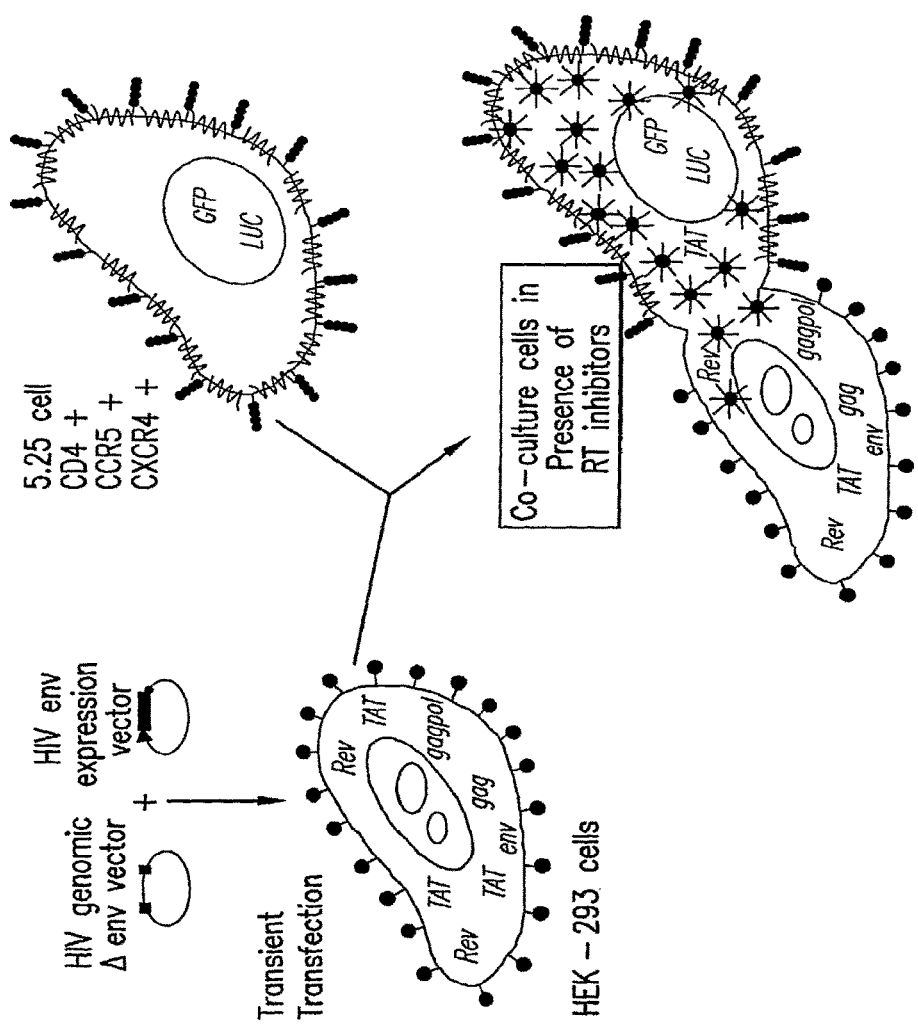

FIG. 5: Fusogenicity Assay.

FIG. 5 presents a diagrammatic representation of a fusogenicity assay performed to assess the fusogenic activity of HIV envelope proteins.

Figure 6:
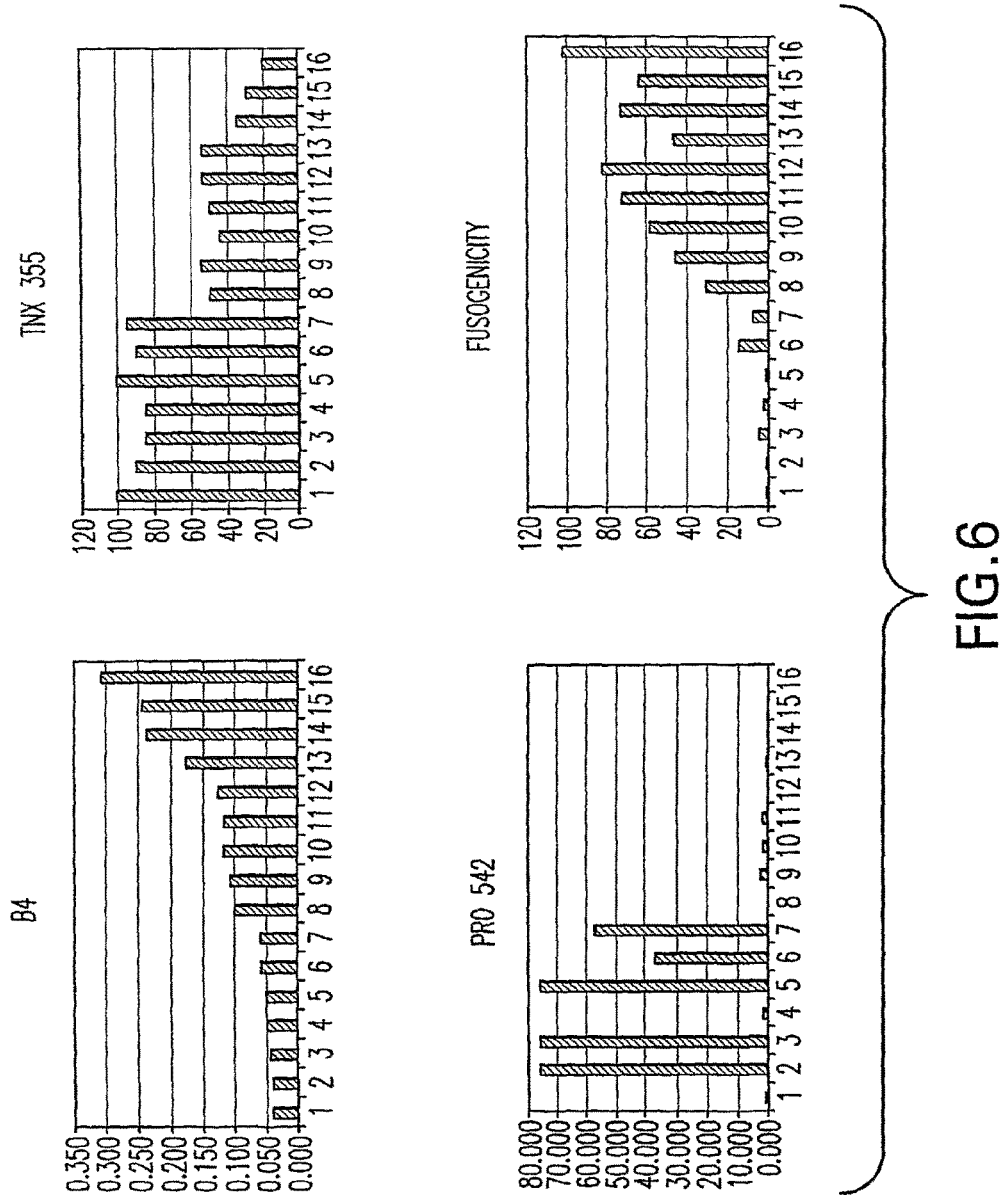

FIG. 6: Sensitivity or Resistance to Monoclonal Antibody B4, TNX 355, and PRO 542 and Fusogenicity of Sixteen Clones.

FIG. 6 presents a graphical representation of resistance or sensitivity to B4, TNX 355, and PRO542 and fusogenicity of sixteen individual HIV obtained from a single patient sample. The Y-axis for the different inhibitors represents the IC$_{50}$ for the drugs, while the fusogenicity panel represents the fusogenicity of the clones as a percentage of fusogenicity observed for reference strain HXB2.

FIG. 7: Alignment of Variable Region 1 (V1) of the Envelope Protein of Sixteen Clones isolated from a Single Patient. Specifically, FIG. 7 shows the amino acid sequences of the V1 region, including glycosylation site motifs contained within, from clones 3, 20, 47, 48, 18, 17, 35, 11, 24, and 5 (SEQ ID NO:1), from clone 39 (SEQ ID NO:2), from clones 21 and 26 (SEQ ID NO:3), from clone 6 (SEQ ID NO:4), from clone 36 (SEQ ID NO:5), and from clone 43 (SEQ ID NO:6), respectively.

FIG. 7 presents an alignment of variable region 1 from the envelope protein of the sixteen clones isolated from a single HIV-infected subject. Glycosylation sites are indicated by arrows.

FIG. 8: Alignment of Variable Region 4 (V4) of the Envelope Protein of Sixteen Clones isolated from a Single Patient. Specifically, FIG. 8 shows the amino acid sequences of the V4 region, including glycosylation site motifs contained within, from clones 3, 20, 47, 48, 18, 17, 35, 11 and 5 (SEQ ID NO:7); from clone 39 (SEQ ID NO:8); from clone 24 (SEQ ID NO:9). from clones 21, 26, and 6 (SEQ ID NO:10); and from clones 36 and 43 (SEQ ID NO:11), respectively.

FIG. 8 presents an alignment of variable region 4 from the envelope protein of the sixteen clones isolated from a single HIV-infected subject. Glycosylation sites are indicated by the arrows; arrows at the top of the alignment indicate glycosylation sites present in all clones, while arrows at the bottom of the alignment indicate glycosylation sites present in subsets of clones. The left arrow at the bottom indicates a glycosylation site present only in clones 36 and 43; the right arrow at the bottom indicates a glycosylation site present in all clones shown except clone 39.

FIG. 9: Alignment of Variable Region 5 (V5) of the Envelope Protein of Sixteen Clones isolated from a Single Patient. Specifically, FIG. 9 shows the amino acid sequences of the V5 region, including glycosylation site motifs contained within, from clones 3, 20, 39, 47, 48, 18, 17, 35, 11, 24, and 5 (SEQ ID NO:12); from clones 21 and 26 (SEQ ID NO:13); from clone 6 (SEQ ID NO:14); and from clones 36 and 43 (SEQ ID NO:15), respectively.

FIG. 9 presents an alignment of variable region 5 from the envelope protein of the sixteen clones isolated from a single HIV-infected subject. Glycosylation sites are indicated by the arrows; the arrow at the top of the alignment indicates a glycosylation site present in all clones, while the arrow at the bottom of the alignment indicates a glycosylation site present in a subset of clones.

Figure 10:
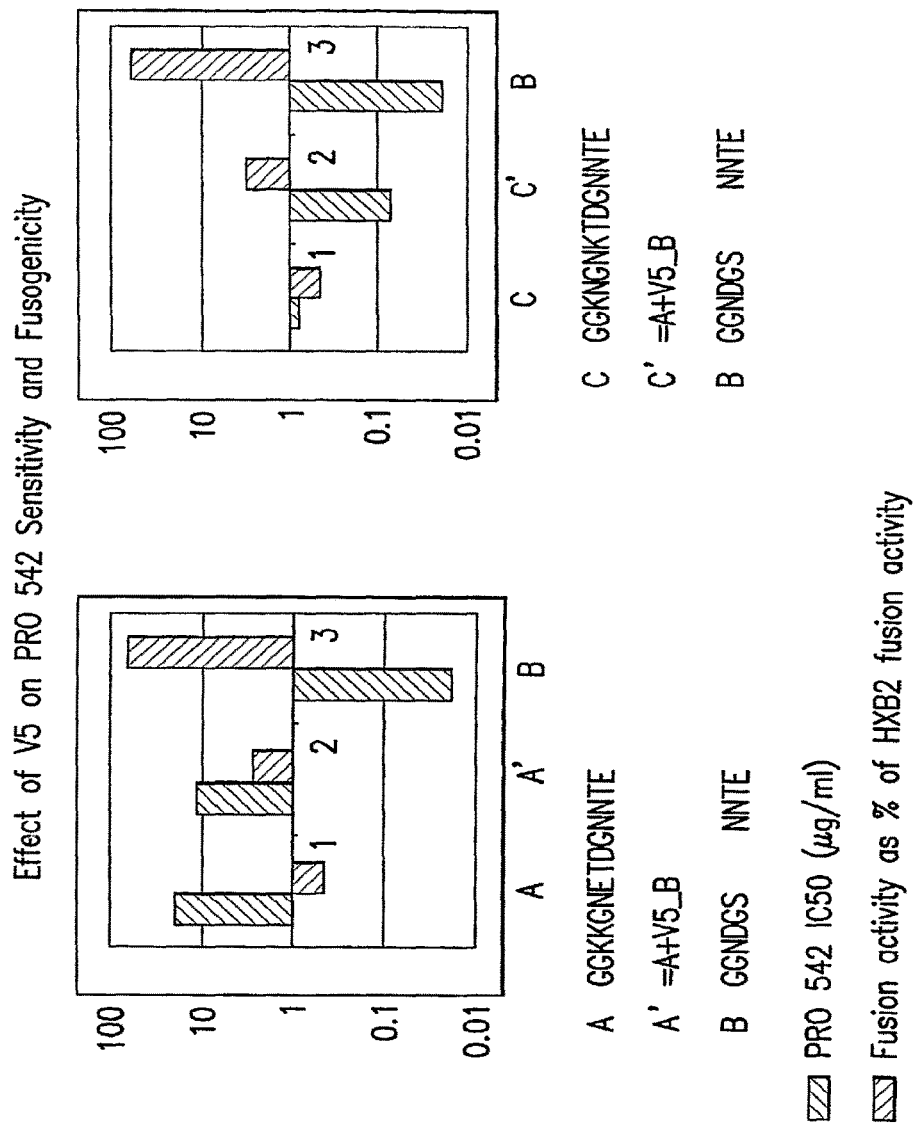

FIG. 10: Effects of Changes in Variable Region 5 on Sensitivity to PRO542 and Fusogenicity.

FIG. 10 presents a graphical representation of the effects of changes in the V5 region of the envelope protein on sensitivity to PRO542 and fusogenicity. Strains A (amino acids 1-14 of SEQ ID NO:13), B (amino acids 1-10 of SEQ ID NO:12), and C (amino acids 1-14 of SEQ ID NO:15), are individual viral isolates with a V5 sequence as presented in FIG. 10. Strains A' and C' are strains A and C, respectively, with their V5 sequences substituted with the B strain V5 sequence.

Figure 11:
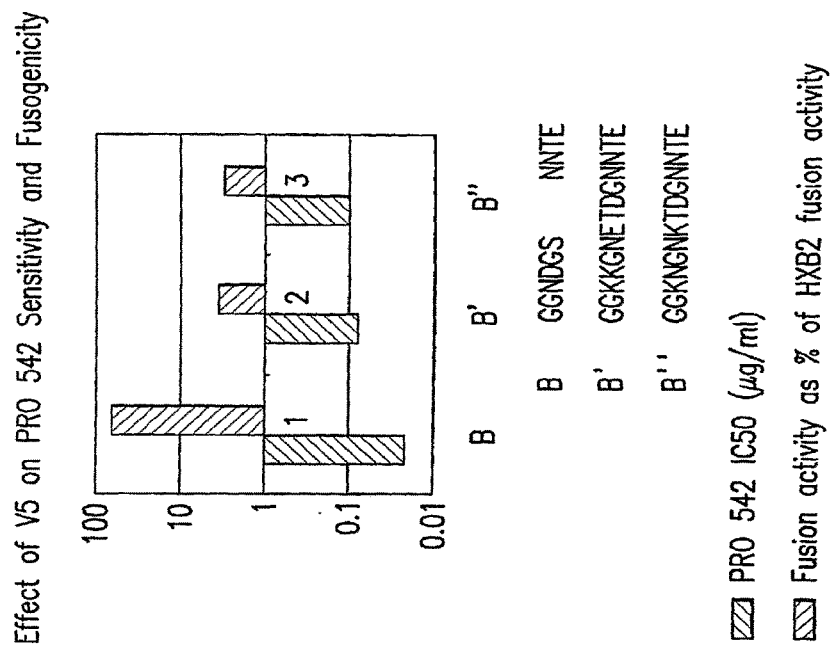

FIG. 11: Effects of Changes in Variable Region 5 on Sensitivity to PRO542 and Fusogenicity.

FIG. 11 presents a graphical representation of the effects of changes in the V5 region of the envelope protein on sensitivity to PRO542 and fusogenicity. Strain B (amino acids 1-10 of SEQ ID NO:12); strain B' (amino acids 1-14 of SEQ ID NO:13) and strain B" (amino acids 1-14 of SEQ ID NO:15) are strain B with their V5 sequence replaced with the V5 regions of strains A and C, respectively, where strains A and C are also as described above in the legend to FIG. 10.

Figure 12:
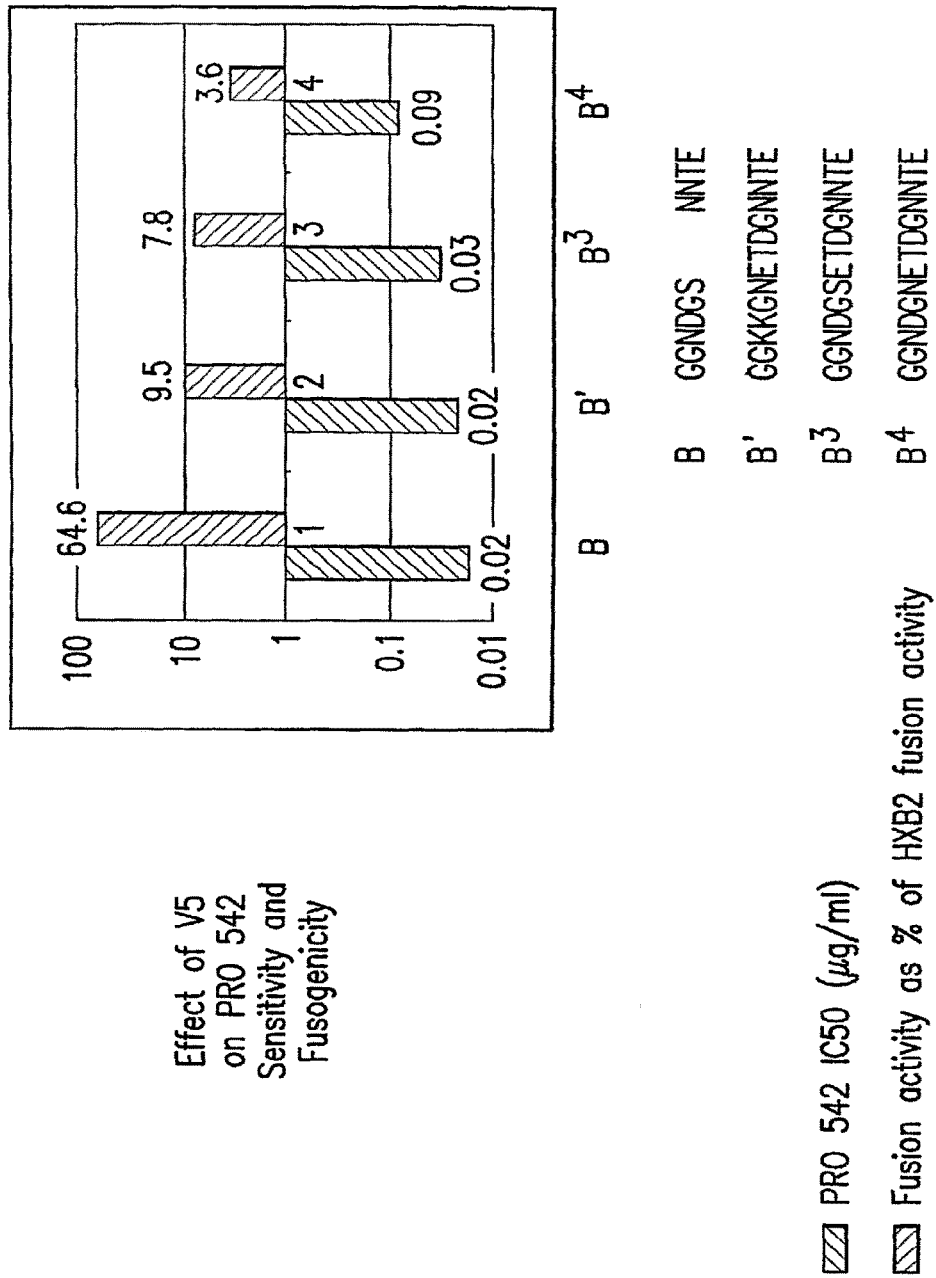

FIG. 12: Effects of Changes in Variable Region 5 on Sensitivity to PRO542 and Fusogenicity.

FIG. 12 presents a graphical representation of the effects of changes in the V5 region of the envelope protein on sensitivity to PRO542 and fusogenicity. Strain B is as described above in the legend to FIG. 10 (amino acids 1-10 of SEQ ID NO:12), strain B' (amino acids 1-14 of SEQ ID NO:13) is as described above in the legend to FIG. 11, and strains B$^3$ (SEQ ID NO:26) and B$^4$ (SEQ ID NO:27) are strain B with their V5 sequences replaced with the sequences shown in FIG. 12.

Figure 13:
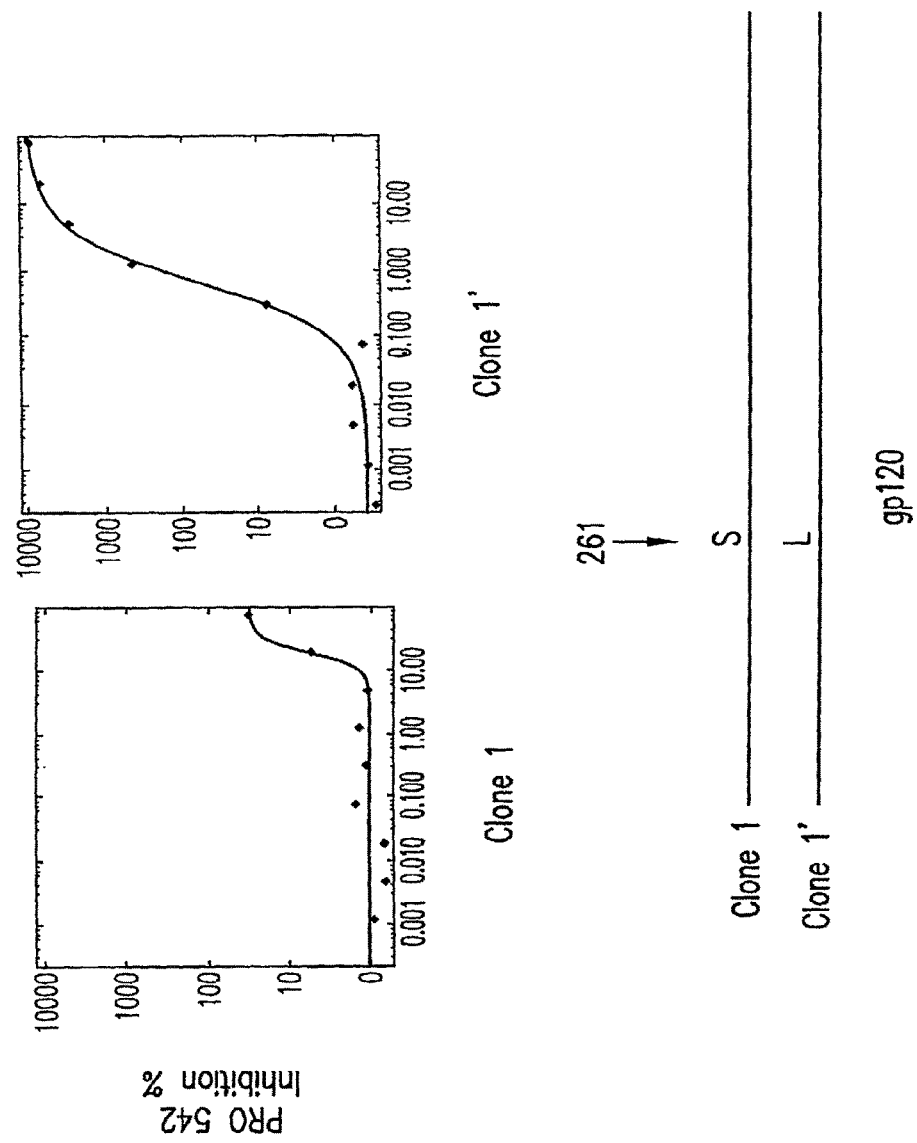

FIG. 13: Suppression of Sensitivity to PRO542 by the L261S Mutation.

FIG. 13 presents log-sigmoid curves showing the sensitivity or resistance to PRO542 in the presence and absence of the L261S mutation. As shown in FIG. 13, an otherwise sensitive virus (IC$_{50}$ of about 0.9 µg/ml) is more resistant to PRO542 (IC$_{50}$ of about 11 µg/ml) in the presence of the L261S mutation.

5. DEFINITIONS

As used herein, the following terms shall have the following meanings:

A "phenotypic assay" is a test that measures a phenotype of a particular virus, such as, for example, HIV, or a population of viruses, such as, for example, the population of HIV infecting a subject. The phenotypes that can be measured include, but are not limited to, the resistance or susceptibility of a virus, or of a population of viruses, to a specific anti-viral agent or that measures the replication capacity of a virus.

A "genotypic assay" is an assay that determines a genotype of an organism, a part of an organism, a population of organisms, a gene, a part of a gene, or a population of genes. Typically, a genotypic assay involves determination of the nucleic acid sequence of the relevant gene or genes. Such assays are frequently performed in HIV to establish, for example, whether certain mutations are associated with drug resistance or resistance or altered replication capacity are present.

The term "% sequence identity" is used interchangeably herein with the term "% identity" and refers to the level of amino acid sequence identity between two or more peptide sequences or the level of nucleotide sequence identity between two or more nucleotide sequences, when aligned using a sequence alignment program. For example, as used herein, 80% identity means the same thing as 80% sequence identity determined by a defined algorithm, and means that a given sequence is at least 80% identical to another length of another sequence. Exemplary levels of sequence identity include, but are not limited to, 60, 70, 80, 85, 90, 95, 98% or more sequence identity to a given sequence.

The term "% sequence homology" is used interchangeably herein with the term "% homology" and refers to the level of amino acid sequence homology between two or more peptide sequences or the level of nucleotide sequence homology between two or more nucleotide sequences, when aligned using a sequence alignment program. For example, as used herein, 80% homology means the same thing as 80% sequence homology determined by a defined algorithm, and accordingly a homologue of a given sequence has greater than 80% sequence homology over a length of the given sequence. Exemplary levels of sequence homology include, but are not limited to, 60, 70, 80, 85, 90, 95, 98% or more sequence homology to a given sequence.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet at the NCBI website. See also Altschul et al., 1990, J. Mol. Biol. 215:403-10 (with special reference to the published default setting, i.e., parameters w=4, t=17) and Altschul et al., 1997, Nucleic Acids Res., 25:3389-3402. Sequence searches are typically carried out using the BLASTP program when evaluating a given amino acid sequence relative to amino acid sequences in the GenBank Protein Sequences and other public databases. The BLASTX program is preferred for searching nucleic acid sequences that have been translated in all reading frames against amino acid sequences in the GenBank Protein Sequences and other public databases. Both BLASTP and BLASTX are run using default parameters of an open gap penalty of 11.0, and an extended gap penalty of 1.0, and utilize the BLOSUM-62 matrix. See id.

A preferred alignment of selected sequences in order to determine "% identity" between two or more sequences, is performed using for example, the CLUSTAL-X program, operated with default parameters, including an open gap penalty of 10.0, an extended gap penalty of 0.1, and a BLOSUM 30 similarity matrix.

"Polar Amino Acid" refers to a hydrophilic amino acid having a side chain that is uncharged at physiological pH, but which has at least one bond in which the pair of electrons shared in common by two atoms is held more closely by one of the atoms. Genetically encoded polar amino acids include Asn (N), Gln (O) Ser (S) and Thr (T).

"Nonpolar Amino Acid" refers to a hydrophobic amino acid having a side chain that is uncharged at physiological pH and which has bonds in which the pair of electrons shared in common by two atoms is generally held equally by each of the two atoms (i.e., the side chain is not polar). Genetically encoded nonpolar amino acids include Ala (A), Gly (G), Ile (I), Leu (L), Met (M) and Val (V).

"Hydrophilic Amino Acid" refers to an amino acid exhibiting a hydrophobicity of less than zero according to the normalized consensus hydrophobicity scale of Eisenberg et al., 1984, J. Mol. Biol. 179:125-142. Genetically encoded hydrophilic amino acids include Arg (R), Asn (N), Asp (D), Glu (E), Gln (O), H is (H), Lys (K), Ser (S) and Thr (T).

"Hydrophobic Amino Acid" refers to an amino acid exhibiting a hydrophobicity of greater than zero according to the normalized consensus hydrophobicity scale of Eisenberg et al., 1984, J. Mol. Biol. 179:125-142. Genetically encoded hydrophobic amino acids include Ala (A), Gly (G), Ile (I), Leu (L), Met (M), Phe (F), Pro (P), Trp (W), Tyr (Y) and Val (V).

"Acidic Amino Acid" refers to a hydrophilic amino acid having a side chain pK value of less than 7. Acidic amino acids typically have negatively charged side chains at physiological pH due to loss of a hydrogen ion. Genetically encoded acidic amino acids include Asp (D) and Glu (E).

"Basic Amino Acid" refers to a hydrophilic amino acid having a side chain pK value of greater than 7. Basic amino acids typically have positively charged side chains at physiological pH due to association with a hydrogen ion. Genetically encoded basic amino acids include Arg (R), His (H) and Lys (K).

A "mutation" is a change in an amino acid sequence or in a corresponding nucleic acid sequence relative to a reference nucleic acid or polypeptide. For embodiments of the invention comprising HIV protease or reverse transcriptase, the reference nucleic acid encoding protease, reverse transcriptase, or envelope is the protease, reverse transcriptase, or envelope coding sequence, respectively, present in NL4-3 HIV (GenBank Accession No. AF324493). Likewise, the reference protease, reverse transcriptase, or envelope polypeptide is that encoded by the NL4-3 HIV sequence. Although the amino acid sequence of a peptide can be determined directly by, for example, Edman degradation or mass spectroscopy, more typically, the amino sequence of a peptide is inferred from the nucleotide sequence of a nucleic acid that encodes the peptide. Any method for determining the sequence of a nucleic acid known in the art can be used, for example, Maxam-Gilbert sequencing (Maxam et al., 1980, Methods in Enzymology 65:499), dideoxy sequencing (Sanger et al., 1977, Proc. Natl. Acad. Sci. USA 74:5463) or hybridization-based approaches (see e.g., Sambrook et al., 2001, Molecular Cloning: A Laboratory Manual, Cold Spring Harbor Laboratory, $3^{rd}$ ed., NY; and Ausubel et al., 1989, Current Protocols in Molecular Biology, Greene Publishing Associates and Wiley Interscience, NY).

A "mutant" is a virus, gene or protein having a sequence that has one or more changes relative to a reference virus, gene or protein.

The terms "peptide," "polypeptide" and "protein" are used interchangeably throughout.

The term "wild-type" refers to a viral genotype that does not comprise a mutation known to be associated with drug resistance.

The terms "polynucleotide," "oligonucleotide" and "nucleic acid" are used interchangeably throughout.

As used herein, a "glycosylation site" refers to a single amino acid or a specific sequence of amino acids that is recognized by one skilled in the art as being suitable for glycosylation as well as a single amino acid or a specific sequence of amino acids that is actually glycosylated.

6. DETAILED DESCRIPTION OF THE INVENTION

In certain aspects, the invention provides a method for determining whether an HIV is resistant to an HIV entry inhibitor. The methods are useful, for example, to guide therapeutic decisions in treatment subjects infected with HIV, whether newly infected or failing treatment, for screening compounds to identify compounds that will affect viruses resistant to other entry inhibitors, and to test whether anti-HIV antibodies can neutralize infection by a broad range of HIV that may be resistant to other strategies for treating and/or preventing HIV infection. Other uses of such methods will be apparent to those of skill in the art.

6.1 Methods for Determining Whether an HIV or HIV Population is Resistant to Entry Inhibitors In one aspect, the invention provides a method for determining whether an HIV is resistant to an HIV entry inhibitor. In certain aspects, the method for determining whether an HIV is likely to be more resistant to a CD4 binding site entry inhibitor than a reference HIV comprises comparing the length of one or more variable regions of an envelope protein of the HIV and/or a number of glycosylation sites on the envelope protein of the HIV to the length of one or more corresponding variable regions of an envelope protein of the reference HIV or the number of glycosylation sites on the envelope protein of the reference HIV, respectively, wherein the HIV is likely to be more resistant to the CD4 binding site entry inhibitor than the reference HIV when the HIV has a longer variable region or regions than the reference HIV and/or the HIV has more glycosylation sites than the reference HIV. In certain embodiments, the CD4 binding site entry inhibitor is selected from the group consisting of PRO542, TNX-355 and monoclonal antibody B12. Generally, a CD4 binding site inhibitor, as described herein, is an entry inhibitor that competes with CD4 for binding to gp120. Accordingly, in certain embodiments, the CD4 binding site inhibitor can be any entry inhibitor that competes with CD4 for binding to gp120 without limitation. For example, any soluble form of CD4 is a CD4 binding site inhibitor. In certain embodiments, the reference HIV is NL4-3, HXB2, or SF2. In certain embodiments, the HIV has longer variable regions than the reference HIV. In certain embodiments, the HIV has more glycosylation sites than the reference HIV. In certain embodiments, the HIV has longer variable regions and more glycosylation sites than the reference HIV.

In certain embodiments, at least one of the variable regions of the HIV is at least 2 amino acids longer than a corresponding variable region of the reference HIV. In certain embodiments, at least one of the variable regions of the HIV is at least 5 amino acids longer than a corresponding variable region of the reference HIV. In certain embodiments, at least one of the variable regions of the HIV is at least 8 amino acids longer than a corresponding variable region of the reference HIV. In certain embodiments, at least one of the variable regions of the HIV is at least 10 amino acids longer than a corresponding variable region of the reference HIV. In certain embodiments, at least one of the variable regions of the HIV is at least 12 amino acids longer than a corresponding variable region of the reference HIV. In certain embodiments, at least one of the variable regions of the HIV is at least 15 amino acids longer than a corresponding variable region of the reference HIV. In certain embodiments, at least one of the variable regions of the HIV is at least 17 amino acids longer than a corresponding variable region of the reference HIV. In certain embodiments, at least one of the variable regions of the HIV is at least 20 amino acids longer than a corresponding variable region of the reference HIV. In certain embodiments, at least one of the variable regions of the HIV is at least 22 amino acids longer than a corresponding variable region of the reference HIV. In certain embodiments, at least one of the variable regions of the HIV is at least 25 amino acids longer than a corresponding variable region of the reference HIV. In certain embodiments, at least one of the variable regions of the HIV is at least 28 amino acids longer than a corresponding variable region of the reference HIV. In certain embodiments, at least one of the variable regions of the HIV is at least 30 amino acids longer than a corresponding variable region of the reference HIV. In certain embodiments, at least one of the variable regions of the HIV is at least 35 amino acids longer than a corresponding variable region of the reference HIV. In certain embodiments, at least one of the variable regions of the HIV is at least 40 amino acids longer than a corresponding variable region of the reference HIV.

In certain embodiments, at least one of the variable regions of the HIV is at least 5% longer than a corresponding variable region of the reference HIV. In certain embodiments, at least one of the variable regions of the HIV is at least 10% longer than a corresponding variable region of the reference HIV. In certain embodiments, at least one of the variable regions of the HIV is at least 15% longer than a corresponding variable region of the reference HIV. In certain embodiments, at least one of the variable regions of the HIV is at least 20% longer than a corresponding variable region of the reference HIV. In certain embodiments, at least one of the variable regions of the HIV is at least 25% longer than a corresponding variable region of the reference HIV. In certain embodiments, at least one of the variable regions of the HIV is at least 30% longer than a corresponding variable region of the reference HIV. In certain embodiments, at least one of the variable regions of the HIV is at least 35% longer than a corresponding variable region of the reference HIV. In certain embodiments, at least one of the variable regions of the HIV is at least 40% longer than a corresponding variable region of the reference HIV. In certain embodiments, at least one of the variable regions of the HIV is at least 45% longer than a corresponding variable region of the reference HIV. In certain embodiments, at least one of the variable regions of the HIV is at least 50% longer than a corresponding variable region of the reference HIV. In certain embodiments, at least one of the variable regions of the HIV is at least 55% longer than a corresponding variable region of the reference HIV. In certain embodiments, at least one of the variable regions of the HIV is at least 60% longer than a corresponding variable region of the reference HIV. In certain embodiments, at least one of the variable regions of the HIV is at least 65% longer than a corresponding variable region of the reference HIV. In certain embodiments, at least one of the variable regions of the HIV is at least 70% longer than a corresponding variable region of the reference HIV. In certain embodiments, at least one of the variable regions of the HIV is at least 75% longer than a corresponding variable region of the reference HIV. In certain embodiments, at least one of the variable regions of the HIV is at least 80% longer than a corresponding variable region of the reference HIV. In certain embodiments, at least one of the variable regions of the HIV is at least 85% longer than a corresponding variable region of the reference HIV. In certain embodiments, at least one of the variable regions of the HIV is at least 90% longer than a corresponding variable region of the reference HIV. In certain embodiments, at least one of the variable regions of the HIV is at least 95% longer than a corresponding variable region of the reference HIV. In certain embodiments, at least one of the variable regions of the HIV is at least 100% longer than a corresponding variable region of the reference HIV. In certain embodiments, at least one of the variable regions of the HIV is at least 125% longer than a corresponding variable region of the reference HIV. In certain embodiments, at least one of the variable regions of the HIV is at least 150% longer than a corresponding variable region of the reference HIV. In certain embodiments, at least one of the variable regions of the HIV is at least 175% longer than a corresponding variable region of the reference HIV. In certain embodiments, at least one of the variable regions of the HIV is at least 200% longer than a corresponding variable region of the reference HIV.

In certain embodiments, at least one of the variable regions of the HIV is longer than a corresponding variable region of the reference HIV. In certain embodiments, at least two of the variable regions of the HIV are longer than a corresponding variable region of the reference HIV. In certain embodiments, at least three of the variable regions of the HIV are longer than a corresponding variable region of the reference HIV. In certain embodiments, at least four of the variable regions of the HIV are longer than a corresponding variable region of the reference HIV. In certain embodiments, at least five of the variable regions of the HIV are longer than a corresponding variable region of the reference HIV. In certain embodiments, all of the variable regions of the HIV are longer than a corresponding variable region of the reference HIV. In certain embodiments, the V1 region of the HIV is longer than the V1 region of the reference HIV. In certain embodiments, the V2 region of the HIV is longer than the V2 region of the reference HIV. In certain embodiments, the V3 region of the HIV is longer than the V3 region of the reference HIV. In certain embodiments, the V4 region of the HIV is longer than the V4 region of the reference HIV. In certain embodiments, the V5 region of the HIV is longer than the V5 region of the reference HIV.

In certain embodiments, the HIV's envelope protein comprises at least one more glycosylation site than the reference HIV's envelope protein. As is well-known in the art, HIV envelope protein is glycosylated at T or S residues present in the motif N—X-T/S—X, where X is any amino acid that is not proline. In certain embodiments, the HIV's envelope protein comprises at least two more glycosylation sites than the reference HIV's envelope protein. In certain embodiments, the HIV's envelope protein comprises at least three more glycosylation sites than the reference HIV's envelope protein. In certain embodiments, the HIV's envelope protein comprises at least four more glycosylation sites than the reference HIV's envelope protein. In certain embodiments, the HIV's envelope protein comprises at least five more glycosylation sites than the reference HIV's envelope protein. In certain embodiments, the HIV's envelope protein comprises at least six more glycosylation sites than the reference HIV's envelope protein. In certain embodiments, the HIV's envelope protein comprises at least seven more glycosylation sites than the reference HIV's envelope protein. In certain embodiments, the HIV's envelope protein comprises at least eight more glycosylation sites than the reference HIV's envelope protein. In certain embodiments, the HIV's envelope protein comprises at least nine more glycosylation sites than the reference HIV's envelope protein. In certain embodiments, the HIV's envelope protein comprises at least ten more glycosylation sites than the reference HIV's envelope protein. In certain embodiments, the HIV's envelope protein comprises at least eleven more glycosylation sites than the reference HIV's envelope protein. In certain embodiments, the HIV's envelope protein comprises at least twelve more glycosylation sites than the reference HIV's envelope protein. In certain embodiments, the HIV's envelope protein comprises at least thirteen more glycosylation sites than the reference HIV's envelope protein. In certain embodiments, the HIV's envelope protein comprises at least fourteen more glycosylation sites than the reference HIV's envelope protein. In certain embodiments, the HIV's envelope protein comprises at least fifteen more glycosylation sites than the reference HIV's envelope protein.

In another aspect, the invention provides a method for determining whether an HIV is likely to be more resistant to a CD4-blocking entry inhibitor than a reference HIV, comprising comparing the length of one or more variable regions of an envelope protein of the HIV and/or the number of glycosylation sites on the envelope protein of the HIV to the length of one or more corresponding variable regions of an envelope protein of the reference HIV and/or the number of glycosylation sites on the envelope protein of the reference HIV, respectively, wherein the HIV is likely to be more resistant to the CD4 binding site entry inhibitor than the reference HIV when the HIV has a shorter variable region or regions than the reference HIV and/or the HIV has fewer glycosylation sites than the reference HIV. In certain embodiments, the entry inhibitor is monoclonal antibody B4. As used herein, a CD4 blocking inhibitor is an entry inhibitor that binds CD4 in a manner that does not compete with gp120 but nonetheless interferes with CD4-gp120 interactions. Accordingly, in certain embodiments, the CD4-blocking entry inhibitor can be any entry inhibitor that binds CD4 in a manner that does not compete with gp120 but nonetheless interferes with CD4-gp120 interactions without limitation. In certain embodiments, the reference HIV is NL4-3, HXB2, or SF2. In certain embodiments, the HIV has shorter variable regions than the reference HIV. In certain embodiments, the HIV has fewer glycosylation sites than the reference HIV. In certain embodiments, the HIV has shorter variable regions and fewer glycosylation sites than the reference HIV.

In certain embodiments, at least one of the variable regions of the HIV is at least 2 amino acids shorter than a corresponding variable region of the reference HIV. In certain embodiments, at least one of the variable regions of the HIV is at least 5 amino acids shorter than a corresponding variable region of the reference HIV. In certain embodiments, at least one of the variable regions of the HIV is at least 8 amino acids shorter than a corresponding variable region of the reference HIV. In certain embodiments, at least one of the variable regions of the HIV is at least 10 amino acids shorter than a corresponding variable region of the reference HIV. In certain embodiments, at least one of the variable regions of the HIV is at least 12 amino acids shorter than a corresponding variable region of the reference HIV. In certain embodiments, at least one of the variable regions of the HIV is at least 15 amino acids shorter than a corresponding variable region of the reference HIV. In certain embodiments, at least one of the variable regions of the HIV is at least 17 amino acids shorter than a corresponding variable region of the reference HIV. In certain embodiments, at least one of the variable regions of the HIV is at least 20 amino acids shorter than a corresponding variable region of the reference HIV. In certain embodiments, at least one of the variable regions of the HIV is at least 22 amino acids shorter than a corresponding variable region of the reference HIV. In certain embodiments, at least one of the variable regions of the HIV is at least 25 amino acids shorter than a corresponding variable region of the reference HIV. In certain embodiments, at least one of the variable regions of the HIV is at least 28 amino acids shorter than a corresponding variable region of the reference HIV. In certain embodiments, at least one of the variable regions of the HIV is at least 30 amino acids shorter than a corresponding variable region of the reference HIV. In certain embodiments, at least one of the variable regions of the HIV is at least 35 amino acids shorter than a corresponding variable region of the reference HIV. In certain embodiments, at least one of the variable regions of the HIV is at least 40 amino acids shorter than a corresponding variable region of the reference HIV.

In certain embodiments, at least one of the variable regions of the HIV is at least 5% shorter than a corresponding variable region of the reference HIV. In certain embodiments, at least one of the variable regions of the HIV is at least 10% shorter than a corresponding variable region of the reference HIV. In certain embodiments, at least one of the variable regions of the HIV is at least 15% shorter than a corresponding variable region of the reference HIV. In certain embodiments, at least one of the variable regions of the HIV is at least 20% shorter than a corresponding variable region of the reference HIV. In certain embodiments, at least one of the variable regions of the HIV is at least 25% shorter than a corresponding variable region of the reference HIV. In certain embodiments, at least one of the variable regions of the HIV is at least 30% shorter than a corresponding variable region of the reference HIV. In certain embodiments, at least one of the variable regions of the HIV is at least 35% shorter than a corresponding variable region of the reference HIV. In certain embodiments, at least one of the variable regions of the HIV is at least 40% shorter than a corresponding variable region of the reference HIV. In certain embodiments, at least one of the variable regions of the HIV is at least 45% shorter than a corresponding variable region of the reference HIV. In certain embodiments, at least one of the variable regions of the HIV is at least 50% shorter than a corresponding variable region of the reference HIV. In certain embodiments, at least one of the variable regions of the HIV is at least 55% shorter than a corresponding variable region of the reference HIV. In certain embodiments, at least one of the variable regions of the HIV is at least 60% shorter than a corresponding variable region of the reference HIV. In certain embodiments, at least one of the variable regions of the HIV is at least 65% shorter than a corresponding variable region of the reference HIV. In certain embodiments, at least one of the variable regions of the HIV is at least 70% shorter than a corresponding variable region of the reference HIV. In certain embodiments, at least one of the variable regions of the HIV is at least 75% shorter than a corresponding variable region of the reference HIV. In certain embodiments, at least one of the variable regions of the HIV is at least 80% shorter than a corresponding variable region of the reference HIV. In certain embodiments, at least one of the variable regions of the HIV is at least 85% shorter than a corresponding variable region of the reference HIV. In certain embodiments, at least one of the variable regions of the HIV is at least 90% shorter than a corresponding variable region of the reference HIV. In certain embodiments, at least one of the variable regions of the HIV is at least 95% shorter than a corresponding variable region of the reference HIV.

In certain embodiments, at least one of the variable regions of the HIV is shorter than a corresponding variable region of the reference HIV. In certain embodiments, at least two of the variable regions of the HIV are shorter than a corresponding variable region of the reference HIV. In certain embodiments, at least three of the variable regions of the HIV are shorter than a corresponding variable region of the reference HIV. In certain embodiments, at least four of the variable regions of the HIV are shorter than a corresponding variable region of the reference HIV. In certain embodiments, at least five of the variable regions of the HIV are shorter than a corresponding variable region of the reference HIV. In certain embodiments, all of the variable regions of the HIV are shorter than a corresponding variable region of the reference HIV. In certain embodiments, the V1 region of the HIV is shorter than the V1 region of the reference HIV. In certain embodiments, the V2 region of the HIV is shorter than the V2 region of the reference HIV. In certain embodiments, the V3 region of the HIV is shorter than the V3 region of the reference HIV. In certain embodiments, the V4 region of the HIV is shorter than the V4 region of the reference HIV. In certain embodiments, the V5 region of the HIV is shorter than the V5 region of the reference HIV.

In certain embodiments, the HIV's envelope protein comprises at least one fewer glycosylation site than the reference HIV's envelope protein. In certain embodiments, the HIV's envelope protein comprises at least two fewer glycosylation sites than the reference HIV's envelope protein. In certain embodiments, the HIV's envelope protein comprises at least three fewer glycosylation sites than the reference HIV's envelope protein. In certain embodiments, the HIV's envelope protein comprises at least four fewer glycosylation sites than the reference HIV's envelope protein. In certain embodiments, the HIV's envelope protein comprises at least five fewer glycosylation sites than the reference HIV's envelope protein. In certain embodiments, the HIV's envelope protein comprises at least six fewer glycosylation sites than the reference HIV's envelope protein. In certain embodiments, the HIV's envelope protein comprises at least seven fewer glycosylation sites than the reference HIV's envelope protein. In certain embodiments, the HIV's envelope protein comprises at least eight fewer glycosylation sites than the reference HIV's envelope protein. In certain embodiments, the HIV's envelope protein comprises at least nine fewer glycosylation sites than the reference HIV's envelope protein. In certain embodiments, the HIV's envelope protein comprises at least ten fewer glycosylation sites than the reference HIV's envelope protein. In certain embodiments, the HIV's envelope protein comprises at least eleven fewer glycosylation sites than the reference HIV's envelope protein. In certain embodiments, the HIV's envelope protein comprises at least twelve fewer glycosylation sites than the reference HIV's envelope protein. In certain embodiments, the HIV's envelope protein comprises at least thirteen fewer glycosylation sites than the reference HIV's envelope protein. In certain embodiments, the HIV's envelope protein comprises at least fourteen fewer glycosylation sites than the reference HIV's envelope protein. In certain embodiments, the HIV's envelope protein comprises at least fifteen fewer glycosylation sites than the reference HIV's envelope protein.

In certain embodiments, the HIV entry inhibitor binds to a cell surface receptor, e.g., CD4, CXCR4, or CCR5. In certain embodiments, the compound is a ligand of the cell surface receptor. In certain embodiments, the compound comprises an antibody. In certain embodiments, the compound inhibits membrane fusion. In certain embodiments, the compound is a peptide, a peptidomimetic, an organic molecule, or a synthetic compound. In certain embodiments, the compound binds the viral envelope protein, e.g., gp120, gp41, and/or gp160.

The invention provides a method for determining whether a virus has developed resistance to an entry inhibitor which comprises: (a) determining whether a virus is resistant to an entry inhibitor according to a method of the invention, wherein a nucleic acid encoding a viral envelope protein is obtained from a subject at a first time; (b) determining whether a virus is resistant to an entry inhibitor according a method of the invention, wherein the nucleic acid encoding the viral envelope protein is obtained from the subject at a later second time; and (c) comparing the susceptibilities determined in steps (a) and (b), wherein a decrease in susceptibility at the later second time indicates that the virus has developed resistance to the entry inhibitor. In a particular embodiment, the subject has undergone or is undergoing anti-HIV therapy comprising an entry inhibitor. In certain embodiments, the entry inhibitor is a CD4 binding site entry inhibitor. In certain embodiments, the entry inhibitor is a CD4 blocking entry inhibitor.

In another aspect, the invention provides a method for determining whether an HIV is likely to exhibit altered susceptibility to an entry inhibitor, comprising detecting, in a nucleic acid encoding an envelope protein of the HIV, a mutation in a codon corresponding to codon 261 of reference HIV strain HXB2, wherein the presence of a mutation in codon 261 indicates that the HIV is likely to be resistant to the entry inhibitor.

In certain embodiments, the mutation in codon 261 encodes serine (S). In certain embodiments, the HIV is an HIV-1. In certain embodiments, the HIV exhibits reduced susceptibility to the entry inhibitor relative to a reference HIV. In certain embodiments, the nucleic acid does not encode a mutation at a codon corresponding to codon 639 of reference HIV strain HXB2. In certain embodiments, the nucleic acid does not encode a mutation at a codon corresponding to codon 749 of reference HIV strain HXB2. In certain embodiments, the nucleic acid does not encode a mutation at a codon corresponding to codon 639 or at codon 749 of reference HIV strain HXB2. In certain embodiments, the nucleic acid does not encode an alanine (A) at a codon corresponding to codon 639 of reference HIV strain HXB2. In certain embodiments, the nucleic acid does not encode an alanine (A) at a codon corresponding to codon 749 of reference HIV strain HXB2. In certain embodiments, the nucleic acid does not encode an alanine (A) at a codon corresponding to codon 639 or at codon 749 of reference HIV strain HXB2.

In another aspect, the invention provides a method for determining whether an HIV is likely to exhibit altered susceptibility to an entry inhibitor, comprising detecting, in a nucleic acid encoding an envelope protein of the HIV, a mutation in one or more codons corresponding to codon 117 and/or at codon 421 of reference HIV strain HXB2, wherein the presence of the mutations indicates that the HIV is likely to be resistant to the entry inhibitor.

In certain embodiments, the HIV is HIV-1. In certain embodiments, the mutation in codon 117 encodes glutamate (E). In certain embodiments, the mutation in codon 421 encodes glutamate (E). In certain embodiments, the HIV exhibits increased susceptibility to an entry inhibitor relative to a reference HIV.

In another aspect, the invention provides a method for determining whether an HIV is likely to exhibit altered susceptibility to an entry inhibitor, comprising detecting, in a nucleic acid encoding an envelope protein of the HIV, a mutation in a codon corresponding to codon 121 and/or codon 298 reference HIV strain HXB2, wherein the presence of the mutations indicates that the HIV is likely to be resistant to the entry inhibitor.

In certain embodiments, the HIV is HIV-1. In certain embodiments, the mutation in codon 121 encodes glutamate (E). In certain embodiments, the mutation in codon 298 encodes serine (S). In certain embodiments, the HIV exhibits reduced susceptibility to an entry inhibitor relative to a reference HIV.

The invention provides for a method for identifying a mutation in a virus that confers resistance to a compound that inhibits viral entry into a cell which comprises: (a) determining the nucleic acid sequence or the amino acid sequence of the virus prior to any treatment of the virus with the compound; (b) obtaining a virus resistant to the compound; (c) determining the nucleic acid sequence or the amino acid sequence of the resistant virus from step (b); and (d) comparing the nucleic acid sequence or the amino acid sequences of steps (a) and (c), respectively, so as to identify the mutation in the virus that confers resistance to the compound.

In certain embodiments, the virus obtained in step (b) is the virus of step (a) grown in the presence of the compound until resistance is developed.

In certain embodiments, the virus obtained in step (b) is isolated from a subject which has been undergoing treatment with the compound.

In certain embodiments, this invention further provides a means and method for discovering, optimizing and characterizing novel or new drugs that target various defined and as yet undefined steps in the virus attachment and entry process.

In certain embodiments, this invention further provides a means and method for discovering, optimizing and characterizing HIV-1 vaccines (either preventative or therapeutic) that target various defined and as yet undefined steps in the virus attachment and entry process.

In certain embodiments, this invention provides a means and method for identifying amino acid substitutions/mutations in HIV-1 envelope proteins (gp41 and/or gp120) that alter susceptibility to inhibitors of virus entry.

In certain embodiments, this invention further provides a means and method for determining HIV-1 envelope amino acid substitutions/mutations that are frequently observed, either alone or in combination, in viruses that exhibit altered susceptibility to virus entry inhibitors.

In certain embodiments, this invention further provides a means and method for using virus entry inhibitor susceptibility to guide the treatment of subjects failing antiretroviral drug treatment.

In certain embodiments, this invention further provides the means and methods for using virus entry inhibitor susceptibility to guide the treatment of subjects newly infected with HIV-1.

In another aspect, the methods comprise determining that a subject is infected with an HIV that is resistant to an HIV entry inhibitor according to a method of the invention, then advising a medical professional of the treatment option of administering to the subject a therapeutic regimen that does not include the HIV entry inhibitor. In certain embodiments, the HIV entry inhibitor is PRO542, TNX-355, mAb B12, or mAb B4. In certain embodiments, the entry inhibitor is selected from the group consisting of BMS-488,403, PRO542, mAb B4, mAb B12, TNX-355, UK-427,857, SCH-D, GW-873,140, AMD-11070, TAK-220, Pro-140, and mAb004. In certain embodiments, the entry inhibitor is selected from the group consisting of TNX-355, UK-427, 857, SCH-D, GW-873,140, AMD-11070, and TAK-220. In certain embodiments, the entry inhibitor is selected from the group consisting of TNX-355, UK-427,857, SCH-D, GW-873,140, and TAK-220. In certain embodiments, the entry inhibitor is BMS-488,403. In certain embodiments, the entry inhibitor is PRO542. In certain embodiments, the entry inhibitor is mAb B4. In certain embodiments, the entry inhibitor is TNX-355. In certain embodiments, the entry inhibitor is UK-427,857. In certain embodiments, the entry inhibitor is SCH-D. In certain embodiments, the entry inhibitor is GW-873,140. In certain embodiments, the entry inhibitor is AMD-11070. In certain embodiments, the entry inhibitor is TAK-220. In certain embodiments, the entry inhibitor is PRO140. In certain embodiments, the entry inhibitor is mAb004. In certain embodiments, the entry inhibitor is mAb B12.

In another aspect, the methods comprise determining that a subject is infected with an HIV that is resistant to an HIV entry inhibitor according to a method of the invention, then advising a medical professional not to treat the subject with the HIV entry inhibitor. In certain embodiments, the HIV entry inhibitor is PRO542, TNX-355, mAb B12, or mAb B4. In certain embodiments, the entry inhibitor is selected from the group consisting of BMS-488,403, PRO542, mAb B4, mAb B12, TNX-355, UK-427,857, SCH-D, GW-873,140, AMD-11070, TAK-220, Pro-140, and mAb004. In certain embodiments, the entry inhibitor is selected from the group consisting of TNX-355, UK-427,857, SCH-D, GW-873,140, AMD-11070, and TAK-220. In certain embodiments, the entry inhibitor is selected from the group consisting of TNX-355, UK-427,857, SCH-D, GW-873,140, and TAK-220. In certain embodiments, the entry inhibitor is BMS- 488,403. In certain embodiments, the entry inhibitor is PRO542. In certain embodiments, the entry inhibitor is mAb B4. In certain embodiments, the entry inhibitor is TNX-355. In certain embodiments, the entry inhibitor is UK-427,857. In certain embodiments, the entry inhibitor is SCH-D. In certain embodiments, the entry inhibitor is GW-873,140. In certain embodiments, the entry inhibitor is AMD-11070. In certain embodiments, the entry inhibitor is TAK-220. In certain embodiments, the entry inhibitor is PRO140. In certain embodiments, the entry inhibitor is mAb004. In certain embodiments, the entry inhibitor is mAb B12.

In still another aspect, the methods comprise determining that a subject is infected with an HIV that is resistant to an HIV entry inhibitor according to a method of the invention, and administering to the subject a combination of anti-HIV agents that does not comprise the HIV entry inhibitor. In certain embodiments, the HIV entry inhibitor is PRO542, TNX-355, mAb B12, or mAb B4. In certain embodiments, the entry inhibitor is selected from the group consisting of BMS-488,403, PRO542, mAb B4, mAb B12, TNX-355, UK-427,857, SCH-D, GW-873,140, AMD-11070, TAK-220, Pro-140, and mAb004. In certain embodiments, the entry inhibitor is selected from the group consisting of TNX-355, UK-427,857, SCH-D, GW-873,140, AMD-11070, and TAK-220. In certain embodiments, the entry inhibitor is selected from the group consisting of TNX-355, UK-427,857, SCH-D, GW-873,140, and TAK-220. In certain embodiments, the entry inhibitor is BMS-488,403. In certain embodiments, the entry inhibitor is PRO542. In certain embodiments, the entry inhibitor is mAb B4. In certain embodiments, the entry inhibitor is TNX-355. In certain embodiments, the entry inhibitor is UK-427,857. In certain embodiments, the entry inhibitor is SCH-D. In certain embodiments, the entry inhibitor is GW-873,140. In certain embodiments, the entry inhibitor is AMD-11070. In certain embodiments, the entry inhibitor is TAK-220. In certain embodiments, the entry inhibitor is PRO140. In certain embodiments, the entry inhibitor is mAb004. In certain embodiments, the entry inhibitor is mAb B12.

In still another aspect, the methods comprise determining that a subject is infected with an HIV that is likely to be more resistant to an HIV entry inhibitor than a reference HIV according to a method of the invention, then advising a medical professional of the treatment option of administering to the subject a combination of anti-HIV agents that does not comprise an effective amount of the HIV entry inhibitor. In certain embodiments, the HIV entry inhibitor is PRO542, TNX-355, mAb B12, or mAb B4. In certain embodiments, the entry inhibitor is selected from the group consisting of BMS-488,403, PRO542, mAb B4, mAb B12, TNX-355, UK-427,857, SCH-D, GW-873,140, AMD-11070, TAK-220, Pro-140, and mAb004. In certain embodiments, the entry inhibitor is selected from the group consisting of TNX-355, UK-427,857, SCH-D, GW-873,140, AMD-11070, and TAK-220. In certain embodiments, the entry inhibitor is selected from the group consisting of TNX-355, UK-427,857, SCH-D, GW-873,140, and TAK-220. In certain embodiments, the entry inhibitor is BMS-488,403. In certain embodiments, the entry inhibitor is PRO542. In certain embodiments, the entry inhibitor is mAb B4. In certain embodiments, the entry inhibitor is TNX-355. In certain embodiments, the entry inhibitor is UK-427,857. In certain embodiments, the entry inhibitor is SCH-D. In certain embodiments, the entry inhibitor is GW-873,140. In certain embodiments, the entry inhibitor is AMD-11070. In certain embodiments, the entry inhibitor is TAK-220. In certain embodiments, the entry inhibitor is PRO140. In certain embodiments, the entry inhibitor is mAb004. In certain embodiments, the entry inhibitor is mAb B12.

In another aspect, the methods comprise determining that a subject is infected with an HIV that is likely to be more resistant to an HIV entry inhibitor than a reference HIV according to a method of the invention, then advising a medical professional of the treatment option of administering to the subject a therapeutic regimen that does not include the HIV entry inhibitor. In certain embodiments, the HIV entry inhibitor is PRO542, TNX-355, mAb B12, or mAb B4. In certain embodiments, the entry inhibitor is selected from the group consisting of BMS-488,403, PRO542, mAb B4, mAb B12, TNX-355, UK-427,857, SCH-D, GW-873,140, AMD-11070, TAK-220, Pro-140, and mAb004. In certain embodiments, the entry inhibitor is selected from the group consisting of TNX-355, UK-427,857, SCH-D, GW-873,140, AMD-11070, and TAK-220. In certain embodiments, the entry inhibitor is selected from the group consisting of TNX-355, UK-427,857, SCH-D, GW-873,140, and TAK-220. In certain embodiments, the entry inhibitor is BMS-488,403. In certain embodiments, the entry inhibitor is PRO542. In certain embodiments, the entry inhibitor is mAb B4. In certain embodiments, the entry inhibitor is TNX-355. In certain embodiments, the entry inhibitor is UK-427,857. In certain embodiments, the entry inhibitor is SCH-D. In certain embodiments, the entry inhibitor is GW-873,140. In certain embodiments, the entry inhibitor is AMD-11070. In certain embodiments, the entry inhibitor is TAK-220. In certain embodiments, the entry inhibitor is PRO140. In certain embodiments, the entry inhibitor is mAb004. In certain embodiments, the entry inhibitor is mAb B12.

In another aspect, the methods comprise determining that a subject is infected with an HIV that is likely to be more susceptible to an HIV entry inhibitor than a reference HIV according to a method of the invention, then advising a medical professional to treat the subject with the HIV entry inhibitor. In certain embodiments, the HIV entry inhibitor is PRO 542, TNX-355, mAb B12, or mAb B4. In certain embodiments, the entry inhibitor is selected from the group consisting of BMS-488,403, PRO542, mAb B4, mAb B12, TNX-355, UK-427,857, SCH-D, GW-873,140, AMD-11070, TAK-220, Pro-140, and mAb004. In certain embodiments, the entry inhibitor is selected from the group consisting of TNX-355, UK-427,857, SCH-D, GW-873,140, AMD-11070, and TAK-220. In certain embodiments, the entry inhibitor is selected from the group consisting of TNX-355, UK-427,857, SCH-D, GW-873,140, and TAK-220. In certain embodiments, the entry inhibitor is BMS-488,403. In certain embodiments, the entry inhibitor is PRO542. In certain embodiments, the entry inhibitor is mAb B4. In certain embodiments, the entry inhibitor is TNX-355. In certain embodiments, the entry inhibitor is UK-427,857. In certain embodiments, the entry inhibitor is SCH-D. In certain embodiments, the entry inhibitor is GW-873,140. In certain embodiments, the entry inhibitor is AMD-11070. In certain embodiments, the entry inhibitor is TAK-220. In certain embodiments, the entry inhibitor is PRO140. In certain embodiments, the entry inhibitor is mAb004. In certain embodiments, the entry inhibitor is mAb B12.

In still another aspect, the methods comprise determining that a subject is infected with an HIV that is likely to be more susceptible to an HIV entry inhibitor than a reference HIV according to a method of the invention, and administering to the subject a combination of anti-HIV agents that comprises the HIV entry inhibitor. In certain embodiments, the HIV entry inhibitor is PRO542, TNX-355, mAb B12, or mAb B4. In certain embodiments, the entry inhibitor is selected from the group consisting of BMS-488,403, PRO542, mAb B4, mAb B12, TNX-355, UK-427,857, SCH-D, GW-873,140, AMD-11070, TAK-220, Pro-140, and mAb004. In certain embodiments, the entry inhibitor is selected from the group consisting of TNX-355, UK-427,857, SCH-D, GW-873,140, AMD-11070, and TAK-220. In certain embodiments, the entry inhibitor is selected from the group consisting of TNX-355, UK-427,857, SCH-D, GW-873,140, and TAK-220. In certain embodiments, the entry inhibitor is BMS-488,403. In certain embodiments, the entry inhibitor is PRO542. In certain embodiments, the entry inhibitor is mAb B4. In certain embodiments, the entry inhibitor is TNX-355. In certain embodiments, the entry inhibitor is UK-427,857. In certain embodiments, the entry inhibitor is SCH-D. In certain embodiments, the entry inhibitor is GW-873,140. In certain embodiments, the entry inhibitor is AMD-11070. In certain embodiments, the entry inhibitor is TAK-220. In certain embodiments, the entry inhibitor is PRO140. In certain embodiments, the entry inhibitor is mAb004. In certain embodiments, the entry inhibitor is mAb B12.

In still another aspect, the methods comprise determining that a subject is infected with an HIV that is likely to be more susceptible to an HIV entry inhibitor than a reference HIV according to a method of the invention, then advising a medical professional of the treatment option of administering to the subject a combination of anti-HIV agents that comprises an effective amount of the HIV entry inhibitor. In certain embodiments, the HIV entry inhibitor is PRO542, TNX-355, mAb B12, or mAb B4. In certain embodiments, the entry inhibitor is selected from the group consisting of BMS-488,403, PRO542, mAb B4, mAb B12, TNX-355, UK-427,857, SCH-D, GW-873,140, AMD-11070, TAK-220, Pro-140, and mAb004. In certain embodiments, the entry inhibitor is selected from the group consisting of TNX-355, UK-427,857, SCH-D, GW-873,140, AMD-11070, and TAK-220. In certain embodiments, the entry inhibitor is selected from the group consisting of TNX-355, UK-427,857, SCH-D, GW-873,140, and TAK-220. In certain embodiments, the entry inhibitor is BMS-488,403. In certain embodiments, the entry inhibitor is PRO542. In certain embodiments, the entry inhibitor is mAb B4. In certain embodiments, the entry inhibitor is TNX-355. In certain embodiments, the entry inhibitor is UK-427,857. In certain embodiments, the entry inhibitor is SCH-D. In certain embodiments, the entry inhibitor is GW-873,140. In certain embodiments, the entry inhibitor is AMD-11070. In certain embodiments, the entry inhibitor is TAK-220. In certain embodiments, the entry inhibitor is PRO 140. In certain embodiments, the entry inhibitor is mAb004. In certain embodiments, the entry inhibitor is mAb B12.

In yet another aspect, the methods comprise determining that a subject is infected with an HIV that is likely to be more susceptible to an HIV entry inhibitor than a reference HIV according to a method of the invention, then advising a medical professional of the treatment option of administering to the subject an effective amount of the HIV entry inhibitor. In certain embodiments, the HIV entry inhibitor is PRO542, TNX-355, mAb B12, or mAb B4. In certain embodiments, the entry inhibitor is selected from the group consisting of BMS-488,403, PRO542, mAb B4, mAb B12, TNX-355, UK-427,857, SCH-D, GW-873,140, AMD-11070, TAK-220, Pro-140, and mAb004. In certain embodiments, the entry inhibitor is selected from the group consisting of TNX-355, UK-427,857, SCH-D, GW-873,140, AMD-11070, and TAK-220. In certain embodiments, the entry inhibitor is selected from the group consisting of TNX-355, UK-427,857, SCH-D, GW-873,140, and TAK-220. In certain embodiments, the entry inhibitor is BMS-488,403. In certain embodiments, the entry inhibitor is PRO542. In certain embodiments, the entry inhibitor is mAb B4. In certain embodiments, the entry inhibitor is TNX-355. In certain embodiments, the entry inhibitor is UK-427,857. In certain embodiments, the entry inhibitor is SCH-D. In certain embodiments, the entry inhibitor is GW-873,140. In certain embodiments, the entry inhibitor is AMD-11070. In certain embodiments, the entry inhibitor is TAK-220. In certain embodiments, the entry inhibitor is PRO140. In certain embodiments, the entry inhibitor is mAb004. In certain embodiments, the entry inhibitor is mAb B12.

In still another aspect, the methods comprise determining whether a subject is infected with an HIV that is likely to be more resistant to an HIV entry inhibitor than a reference HIV according to a method of the invention at a first time, then determining whether the subject remains infected with an HIV that is likely to be more resistant to an HIV entry inhibitor than a reference HIV according to a method of the invention at a later second time. In other embodiments, the methods comprise determining whether a subject is infected with an HIV that is likely to be less resistant to an HIV entry inhibitor than a reference HIV according to a method of the invention at a first time, then determining whether the subject is infected with an HIV that is likely to be more resistant to an HIV entry inhibitor than a reference HIV according to a method of the invention at a later second time. In certain embodiments, the entry inhibitor is a CD4 binding site inhibitor as described herein. In certain embodiments, the entry inhibitor is a CD4 blocking inhibitor as described herein.

In yet another aspect, the methods comprise determining whether a subject is infected with an HIV that is likely to be more susceptible to an HIV entry inhibitor than a reference HIV according to a method of the invention at a first time, then determining whether the subject remains infected with an HIV that is likely to be more susceptible to an HIV entry inhibitor than a reference HIV according to a method of the invention at a later second time. In other embodiments, the methods comprise determining whether a subject is infected with an HIV that is likely to be more susceptible to an HIV entry inhibitor than a reference HIV according to a method of the invention at a first time, then determining whether the subject is infected with an HIV that is likely to be more susceptible to an HIV entry inhibitor than a reference HIV according to a method of the invention at a later second time. In certain embodiments, the entry inhibitor is a CD4 binding site inhibitor as described herein. In certain embodiments, the entry inhibitor is a CD4 blocking inhibitor as described herein. In a certain embodiments, the subject has undergone or is undergoing anti-HIV therapy comprising an entry inhibitor. In certain embodiments, the entry inhibitor is a CD4 binding site entry inhibitor. In certain embodiments, the entry inhibitor is a CD4 blocking entry inhibitor.

In still another aspect, the invention provides a method for identifying compounds that can inhibit HIV entry into a cell expressing a receptor that is bound by an HIV envelope protein, comprising performing an entry assay (e.g., as described in Example 1) with an HIV that is more likely to be resistant to an entry inhibitor than a reference HIV as determined with a method of the invention. In still another aspect, the invention provides a method for identifying compounds that can inhibit HIV entry into a cell expressing a receptor that is bound by an HIV envelope protein, comprising performing an entry assay (e.g., as described in Example 1) with an HIV that is less likely to be susceptible to an entry inhibitor than a reference HIV as determined with a method of the invention. In certain embodiments, the entry inhibitor is a CD4 binding site inhibitor as described herein. In certain embodiments, the entry inhibitor is a CD4 blocking inhibitor as described herein.

In yet another aspect, the invention provides a method of assessing an antibody response for its ability to neutralize infection. Methods for performing such assays are extensively described in U.S. application Ser. Nos. 10/077,027 and 10/504,821. In certain embodiments, the assays are performed with an HIV that is more likely to be resistant to an entry inhibitor than a reference HIV as determined with a method of the invention. In certain embodiments, the assays are performed with an HIV that is more likely to be susceptible to an entry inhibitor than a reference HIV as determined with a method of the invention. In certain embodiments, the entry inhibitor is a CD4 binding site inhibitor as described herein. In certain embodiments, the entry inhibitor is a CD4 blocking inhibitor as described herein.

6.2 Determining Viral Variable Region or Glycosylation Genotypes

The length of envelope protein variable regions and/or number of envelope protein glycosylation sites and/or the sequence of envelope protein variable or constant regions can be determined by any means known in the art for detecting a mutation. For example, the length of envelope protein variable regions and/or number of envelope protein glycosylation sites can be detected in the viral gene that encodes a particular protein, or in the protein itself, i.e., in the amino acid sequence of the protein.

A length of envelope protein variable regions and/or number of envelope protein glycosylation sites within the env gene can be detected by utilizing any suitable technique known to one of skill in the art without limitation. Viral DNA or RNA can be used as the starting point for such assay techniques, and may be isolated according to standard procedures which are well known to those of skill in the art.

The determination of specific nucleic acid sequences, such as in a particular region of the env gene, can be accomplished be a variety of methods including, but not limited to, restriction-fragment-length-polymorphism detection based on allele-specific restriction-endonuclease cleavage (Kan and Dozy, 1978, Lancet ii:910-912), mismatch-repair detection (Faham and Cox, 1995, Genome Res 5:474-482), binding of MutS protein (Wagner et al., 1995, Nucl Acids Res 23:3944-3948), denaturing-gradient gel electrophoresis (Fisher et al., 1983, Proc. Natl. Acad. Sci. U.S.A. 80:1579-83), single-strand-conformation-polymorphism detection (Orita et al., 1983, Genomics 5:874-879), RNAase cleavage at mismatched base-pairs (Myers et al, 1985, Science 230:1242), chemical (Cotton et al., 1988, Proc. Natl. Acad. Sci. U.S.A. 85:4397-4401) or enzymatic (Youil et al., 1995, Proc. Natl. Acad. Sci. U.S.A. 92:87-91) cleavage of heteroduplex DNA, methods based on oligonucleotide-specific primer extension (Syvanen et al., 1990, Genomics 8:684-692), genetic bit analysis (Nikiforov et al., 1994, Nucl Acids Res 22:4167-4175), oligonucleotide-ligation assay (Landegren et al., 1988, Science 241:1077), oligonucleotide-specific ligation chain reaction ("LCR") (Barrany, 1991, Proc. Natl. Acad. Sci. U.S.A. 88:189-193), gap-LCR (Abravaya et al., 1995, Nucl Acids Res 23:675-682), radioactive or fluorescent DNA sequencing using standard procedures well known in the art, and peptide nucleic acid (PNA) assays (Orum et al., 1993, Nucl. Acids. Res. 21:5332-5356; Thiede et al., 1996, Nucl. Acids Res. 24:983-984).

In addition, viral DNA or RNA may be used in hybridization or amplification assays to detect abnormalities involving gene structure, including point mutations, insertions, deletions and genomic rearrangements. Such assays may include, but are not limited to, Southern analyses (Southern, 1975, J. Mol. Biol. 98:503-517), single stranded conformational polymorphism analyses (SSCP) (Orita et al., 1989, Proc. Natl. Acad. Sci. USA 86:2766-2770), and PCR analyses (U.S. Pat. Nos. 4,683,202; 4,683,195; 4,800,159; and 4,965,188; PCR Strategies, 1995 Innis et al. (eds.), Academic Press, Inc.).

Such diagnostic methods can involve for example, contacting and incubating the viral nucleic acids with one or more labeled nucleic acid reagents including recombinant DNA molecules, cloned genes or degenerate variants thereof, under conditions favorable for the specific annealing of these reagents to their complementary sequences. Preferably, the lengths of these nucleic acid reagents are at least 15 to 30 nucleotides. After incubation, all non-annealed nucleic acids are removed from the nucleic acid molecule hybrid. The presence of nucleic acids which have hybridized, if any such molecules exist, is then detected. Using such a detection scheme, the nucleic acid from the virus can be immobilized, for example, to a solid support such as a membrane, or a plastic surface such as that on a microtiter plate or polystyrene beads. In this case, after incubation, non-annealed, labeled nucleic acid reagents of the type described above are easily removed. Detection of the remaining, annealed, labeled nucleic acid reagents is accomplished using standard techniques well-known to those in the art. The gene sequences to which the nucleic acid reagents have annealed can be compared to the annealing pattern expected from a normal gene sequence in order to determine the length of envelope protein variable regions and/or number of envelope protein glycosylation sites in the env gene.

These techniques can easily be adapted to provide high-throughput methods for determining the length of envelope protein variable regions and/or number of envelope protein glycosylation sites in viral genomes. For example, a gene array from Affymetrix (Affymetrix, Inc., Sunnyvale, Calif.) can be used to rapidly identify genotypes of a large number of individual viruses. Affymetrix gene arrays, and methods of making and using such arrays, are described in, for example, U.S. Pat. Nos. 6,551,784, 6,548,257, 6,505,125, 6,489,114, 6,451,536, 6,410,229, 6,391,550, 6,379,895, 6,355,432, 6,342,355, 6,333,155, 6,308,170, 6,291,183, 6,287,850, 6,261,776, 6,225,625, 6,197,506, 6,168,948, 6,156,501, 6,141,096, 6,040,138, 6,022,963, 5,919,523, 5,837,832, 5,744,305, 5,834,758, and 5,631,734, each of which is hereby incorporated by reference in its entirety.

In addition, Ausubel et al., eds., Current Protocols in Molecular Biology, 2002, Vol. 4, Unit 25B, Ch. 22, which is hereby incorporated by reference in its entirety, provides further guidance on construction and use of a gene array for determining the genotypes of a large number of viral isolates. Finally, U.S. Pat. Nos. 6,670,124; 6,617,112; 6,309,823; 6,284,465; and 5,723,320, each of which is incorporated by reference in its entirety, describe related array technologies that can readily be adapted for rapid identification of a large number of viral genotypes by one of skill in the art.

Alternative diagnostic methods for the detection of gene specific nucleic acid molecules may involve their amplification, e.g., by PCR (U.S. Pat. Nos. 4,683,202; 4,683,195; 4,800,159; and 4,965,188; PCR Strategies, 1995 Innis et al. (eds.), Academic Press, Inc.), followed by the detection of the amplified molecules using techniques well known to those of skill in the art. The resulting amplified sequences can be compared to those which would be expected if the nucleic acid being amplified contained only normal copies of the respective gene in order to determine the length of envelope protein variable regions and/or number of envelope protein glycosylation sites.

Additionally, the nucleic acid can be sequenced by any sequencing method known in the art. For example, the viral DNA can be sequenced by the dideoxy method of Sanger et al., 1977, Proc. Natl. Acad. Sci. USA 74:5463, as further described by Messing et al., 1981, Nuc. Acids Res. 9:309, or by the method of Maxam et al., 1980, Methods in Enzymology 65:499. See also the techniques described in Sambrook et al., 2001, Molecular Cloning: A Laboratory Manual, Cold Spring Harbor Laboratory, $3^{rd}$ ed., NY; and Ausubel et al., 1989, Current Protocols in Molecular Biology, Greene Publishing Associates and Wiley Interscience, NY.

Antibodies directed against the viral gene products, i.e., viral proteins or viral peptide fragments can also be used to detect the length of envelope protein variable regions and/or number of envelope protein glycosylation sites in the viral proteins. Alternatively, the viral protein or peptide fragments of interest can be sequenced by any sequencing method known in the art in order to yield the amino acid sequence of the protein of interest. An example of such a method is the Edman degradation method which can be used to sequence small proteins or polypeptides. Larger proteins can be initially cleaved by chemical or enzymatic reagents known in the art, for example, cyanogen bromide, hydroxylamine, trypsin or chymotrypsin, and then sequenced by the Edman degradation method.

Further, glycosylation of particular viral peptides can be detected by any method known to one of skill in the art without limitation. For example, conventional mass spectroscopy or NMR techniques can be used to detect the presence and/or identify of glycosylated viral peptides or proteins. See, e.g., Rusnak et al., 2002, J. Biomol. Tech. 13(4):228-237.

6.3 Computer-Implemented Methods for Determining Whether a Virus is Resistant to an Entry Inhibitor and Articles Related Thereto In another aspect, the present invention provides computer-implemented methods for determining whether an HIV is resistant to an entry inhibitor. In such embodiments, the methods of the invention are adapted to take advantage of the processing power of modern computers. One of skill in the art can readily adapt the methods in such a manner. Therefore, in certain embodiments, the invention provides a computer-implemented method for determining whether an HIV is likely to be more resistant to a CD4 binding site entry inhibitor than a reference HIV, comprising inputting genotypic information into a memory system of a computer, wherein the genotypic information comprises the length of at least one variable region of the envelope protein of the HIV and/or the number of glycosylation sites of the envelope protein of the HIV and the length of the corresponding at least one variable region of the envelope protein of the reference HIV and/or the number of glycosylation sites of the envelope protein of the reference HIV, respectively; comparing the length of the at least one variable region of the envelope proteins of the HIV or the number of glycosylation sites of the envelope protein of the HIV to the length of the corresponding at least one variable region of the envelope protein of the HIV and/or the number of glycosylation sites of the envelope protein of the reference HIV, and determining whether the HIV is resistant to the entry inhibitor, wherein the HIV is likely to be more resistant to the CD4 binding site inhibitor than the reference HIV if the at least one variable region of the HIV is longer than the corresponding at least one variable region of the reference HIV and/or the HIV's envelope protein comprises more glycosylation sites than the reference HIV's envelope protein.

In other embodiments, the invention provides a computer-implemented method for determining whether an HIV is likely to be more resistant to a CD4-blocking entry inhibitor than a reference HIV, comprising inputting genotypic information into a memory system of a computer, wherein the genotypic information comprises the length of at least one variable region of the envelope protein of the HIV and/or the number of glycosylation sites of the envelope protein of the HIV and the length of a corresponding at least one variable region of the envelope protein of the reference HIV and/or the number of glycosylation sites of the envelope protein of the reference HIV, respectively; comparing the length of the at least one variable region of the envelope proteins of the HIV or the number of glycosylation sites of the envelope protein of the HIV to the length of the corresponding at least one variable region of the envelope protein of the HIV and/or the number of glycosylation sites of the envelope protein of the reference HIV, and determining whether the HIV is resistant to the entry inhibitor, wherein the HIV is likely to be more resistant to the CD4-blocking entry inhibitor than the reference HIV if the at least one variable region of the HIV is shorter than the corresponding at least one variable region of the reference HIV and/or the HIV's envelope protein comprises fewer glycosylation sites than the reference HIV's envelope protein.

In certain embodiments, the methods further comprise displaying whether the HIV is likely to be more resistant to an HIV entry inhibitor than a reference HIV on a display of the computer. In certain embodiments, the methods further comprise printing whether the HIV is likely to be more resistant to an HIV entry inhibitor than a reference HIV.

In another aspect, the invention provides a tangible medium indicating whether an HIV is likely to be more resistant to an HIV entry inhibitor than a reference HIV produced according to a method of the invention. In certain embodiments, the tangible medium is a computer-readable medium. In certain embodiments, the tangible medium is a paper document. In certain embodiments, the paper document is a printed document, e.g., a computer print-out. In still another aspect, the invention provides a computer-readable medium comprising data indicating whether an HIV is likely to be more resistant to an HIV entry inhibitor than a reference HIV produced according to a method of the invention.

In yet another aspect, the invention provides a computer-readable medium that comprises data indicating whether an HIV is likely to be more resistant to an HIV entry inhibitor than a reference HIV produced according a method of the invention. In certain embodiments, the computer-readable medium is a random-access memory. In certain embodiments, the computer-readable medium is a fixed disk. In certain embodiments, the computer-readable medium is a floppy disk. In certain embodiments, the computer-readable medium is a portable memory device, such as, e.g., a USB key or an iPod™.

In still another aspect, the invention provides an article of manufacture that comprises computer-readable instructions for performing a method of the invention. In certain embodiments, the article of manufacture is a random-access memory. In certain embodiments, the article of manufacture is a fixed disk. In certain embodiments, the article of manufacture is a floppy disk. In certain embodiments, the article of manufacture is a portable memory device, such as, e.g., a USB key or an iPod™.

In yet another aspect, the invention provides a computer-readable medium that comprises data indicating whether an HIV is likely to be more resistant to an HIV entry inhibitor than a reference HIV and computer-readable instructions for performing a method of the invention. In certain embodiments, the computer-readable medium is a random-access memory. In certain embodiments, the computer-readable medium is a fixed disk. In certain embodiments, the computer-readable medium is a floppy disk. In certain embodiments, the computer-readable medium is a portable memory device, such as, e.g., a USB key or an iPod™.

In yet another aspect, the invention provides a computer system that is configured to perform a method of the invention.

6.4 Viruses and Viral Samples

The length of envelope protein variable regions and/or number of envelope protein glycosylation sites can be determined from a viral sample obtained by any means known in the art for obtaining viral samples. Such methods include, but are not limited to, obtaining a viral sample from a human or an animal infected with the virus or obtaining a viral sample from a viral culture. In one embodiment, the viral sample is obtained from a human individual infected with the virus. The viral sample could be obtained from any part of the infected individual's body or any secretion expected to contain the virus. Examples of such parts include, but are not limited to blood, serum, plasma, sputum, lymphatic fluid, semen, vaginal mucus and samples of other bodily fluids. In a preferred embodiment, the sample is a blood, serum or plasma sample.

In another embodiment, the length of envelope protein variable regions and/or number of envelope protein glycosylation sites is determined from a virus that can be obtained from a culture. In some embodiments, the culture can be obtained from a laboratory. In other embodiments, the culture can be obtained from a collection, for example, the American Type Culture Collection. In certain embodiments, the length of envelope protein variable regions and/or number of envelope protein glycosylation sites is determined for NL4-3, SF2, or HXB2.

In certain embodiments, the length of envelope protein variable regions and/or number of envelope protein glycosylation sites is determined from a derivative of a virus. In one embodiment, the derivative of the virus is not itself pathogenic. In another embodiment, the derivative of the virus is a plasmid-based system, wherein replication of the plasmid or of a cell transfected with the plasmid is affected by the presence or absence of the selective pressure, such that mutations are selected that increase resistance to the selective pressure. In some embodiments, the derivative of the virus comprises the nucleic acids or proteins of interest, for example, those nucleic acids or proteins to be targeted by an anti-viral treatment. In one embodiment, the genes of interest can be incorporated into a vector. See, e.g., U.S. application Ser. Nos. 09/874,475 and 10/077,027, each of which is incorporated herein by reference. In certain embodiments, the genes can be those that encode envelope protein (gp160).

In another embodiment, the intact virus need not be used. Instead, a part of the virus incorporated into a vector can be used. Preferably that part of the virus is used that is targeted by an anti-viral drug.

In another embodiment, the length of envelope protein variable regions and/or number of envelope protein glycosylation sites is determined in a genetically modified virus. The virus can be genetically modified using any method known in the art for genetically modifying a virus. For example, the virus can be grown for a desired number of generations in a laboratory culture. In one embodiment, no selective pressure is applied (i.e., the virus is not subjected to a treatment that favors the replication of viruses with certain characteristics), and new mutations accumulate through random genetic drift. In another embodiment, a selective pressure is applied to the virus as it is grown in culture (i.e., the virus is grown under conditions that favor the replication of viruses having one or more characteristics). In one embodiment, the selective pressure is an anti-viral treatment. Any known anti-viral treatment can be used as the selective pressure.

In certain embodiments, the virus is HIV and the selective pressure is a NNRTI. In another embodiment, the virus is HIV-1 and the selective pressure is a NNRTI. Any NNRTI can be used to apply the selective pressure. Examples of NNRTIs include, but are not limited to, nevirapine, delavirdine and efavirenz. By treating HIV cultured in vitro with a NNRTI, one can select for mutant strains of HIV that have an increased resistance to the NNRTI. The stringency of the selective pressure can be manipulated to increase or decrease the survival of viruses not having the selected—for characteristic.

In other embodiments, the virus is HIV and the selective pressure is a NRTI. In another embodiment, the virus is HIV-1 and the selective pressure is a NRTI. Any NRTI can be used to apply the selective pressure. Examples of NRTIs include, but are not limited to, AZT, ddI, ddC, d4T, 3TC, abacavir, and tenofovir. By treating HIV cultured in vitro with a NRTI, one can select for mutant strains of HIV that have an increased resistance to the NRTI. The stringency of the selective pressure can be manipulated to increase or decrease the survival of viruses not having the selected-for characteristic.

In still other embodiments, the virus is HIV and the selective pressure is a PI. In another embodiment, the virus is HIV-1 and the selective pressure is a PI. Any PI can be used to apply the selective pressure. Examples of P is include, but are not limited to, saquinavir, ritonavir, indinavir, nelfinavir, amprenavir, lopinavir and atazanavir. By treating HIV cultured in vitro with a PI, one can select for mutant strains of HIV that have an increased resistance to the PI. The stringency of the selective pressure can be manipulated to increase or decrease the survival of viruses not having the selected-for characteristic.

In still other embodiments, the virus is HIV and the selective pressure is an entry inhibitor. In another embodiment, the virus is HIV-1 and the selective pressure is an entry inhibitor. Any entry inhibitor can be used to apply the selective pressure. An example of a entry inhibitor includes, but is not limited to, fusion inhibitors such as, for example, enfuvirtide. Other entry inhibitors include co-receptor inhibitors, such as, for example, AMD3100 (AnorMED). Such co-receptor inhibitors can include any compound that interferes with an interaction between HIV and a co-receptor, e.g., CCR5 or CRCX4, without limitation. Still other entry inhibitors include UK-427857 (Pfizer), TNX-355 (Tanox Inc.), AMD-070 (AnorMED), Pro 140 (Progenics), FP-21399 (EMD Lexigen), BMS-488043 (Bristol-Myers Squibb), and GSK-873,140 (GlaxoSmithKline). By treating HIV cultured in vitro with an entry inhibitor, one can select for mutant strains of HIV that have an increased resistance to the entry inhibitor. The stringency of the selective pressure can be manipulated to increase or decrease the survival of viruses not having the selected-for characteristic.

In another aspect, a mutation associated with NNRTI hypersusceptibility according to the present invention can be made by mutagenizing a virus, a viral genome, or a part of a viral genome. Any method of mutagenesis known in the art can be used for this purpose. In certain embodiments, the mutagenesis is essentially random. In certain embodiments, the essentially random mutagenesis is performed by exposing the virus, viral genome or part of the viral genome to a mutagenic treatment. In another embodiment, a gene that encodes a viral protein that is the target of an anti-viral therapy is mutagenized. Examples of essentially random mutagenic treatments include, for example, exposure to mutagenic substances (e.g., ethidium bromide, ethylmethanesulphonate, ethyl nitroso urea (ENU) etc.) radiation (e.g., ultraviolet light), the insertion and/or removal of transposable elements (e.g., Tn5, Tn10), or replication in a cell, cell extract, or in vitro replication system that has an increased rate of mutagenesis. See, e.g., Russell et al., 1979, Proc. Nat. Acad. Sci. USA 76:5918-5922; Russell, W., 1982, Environmental Mutagens and Carcinogens: Proceedings of the Third International Conference on Environmental Mutagens. One of skill in the art will appreciate that while each of these methods of mutagenesis is essentially random, at a molecular level, each has its own preferred targets.

In another aspect, the length of envelope protein variable regions and/or number of envelope protein glycosylation sites can be determined in an HIV or HIV derivative made using site-directed mutagenesis. Any method of site-directed mutagenesis known in the art can be used (see e.g., Sambrook et al., 2001, Molecular Cloning: A Laboratory Manual, Cold Spring Harbor Laboratory, 3$^{rd}$ ed., NY; and Ausubel et al., 1989, Current Protocols in Molecular Biology, Greene Publishing Associates and Wiley Interscience, NY). See, e.g., Sarkar and Sommer, 1990, Biotechniques, 8:404-407. The site directed mutagenesis can be directed to, e.g., a particular gene or genomic region, a particular part of a gene or genomic region, or one or a few particular nucleotides within a gene or genomic region. In one embodiment, the site directed mutagenesis is directed to a viral genomic region, gene, gene fragment, or nucleotide based on one or more criteria. In one embodiment, a gene or a portion of a gene is subjected to site-directed mutagenesis because it encodes a protein that is known or suspected to be a target of an anti-viral therapy, e.g., the gene encoding the HIV reverse transcriptase. In another embodiment, a portion of a gene, or one or a few nucleotides within a gene, are selected for site-directed mutagenesis. In one embodiment, the nucleotides to be mutagenized encode amino acid residues that are known or suspected to interact with an anti-viral compound. In another embodiment, the nucleotides to be mutagenized encode amino acid residues that are known or suspected to be mutated in viral strains that are resistant or susceptible or hypersusceptible to one or more antiviral agents. In another embodiment, the mutagenized nucleotides encode amino acid residues that are adjacent to or near in the primary sequence of the protein residues known or suspected to interact with an anti-viral compound or known or suspected to be mutated in viral strains that are resistant or susceptible or hypersusceptible to one or more antiviral agents. In another embodiment, the mutagenized nucleotides encode amino acid residues that are adjacent to or near to in the secondary, tertiary or quaternary structure of the protein residues known or suspected to interact with an anti-viral compound or known or suspected to be mutated in viral strains having an altered replication capacity. In another embodiment, the mutagenized nucleotides encode amino acid residues in or near the active site of a protein that is known or suspected to bind to an anti-viral compound.

7. EXAMPLES

The following examples are presented to further illustrate and explain the present invention and should not be taken as limiting in any regard. Certain of these experiments were also described in U.S. application Ser. Nos. 09/874,475 and 10/077,027, each of which is incorporated by reference in its entirety.

7.1 Example 1

Measuring Phenotypic Drug Susceptibility to Inhibitors of HIV-1 Entry

This example provides a means and method for accurately and reproducibly measuring susceptibility to inhibitors of HIV-1 attachment and entry (heretofore collectively referred to as entry). Based on this example, the means and method for measuring susceptibility to inhibitors of HIV-1 entry can be adapted to other viruses, including, but not limited to other lentiviruses (e.g. HIV-2), other retroviruses (e.g. HTLV-1 and 2), hepadnaviruses (human hepatitis B virus), flaviviruses (human hepatitis C virus) and herpesviruses human cytomegalovirus). This example further provides a means and method for measuring alterations (increases and decreases) in susceptibility to entry inhibitors.

Measurements of entry inhibitor susceptibility are carried out using adaptations of the means and methods for phenotypic drug susceptibility and resistance tests described in U.S. Pat. No. 5,837,464 (International Publication Number WO 97/27319) which is hereby incorporated by reference.

One vector, an example of the envelope expression vector, (pHIVenv) is designed to express the envelope polyprotein (gp160) encoded by subject derived HIV envelope sequences (FIG. 1). Gp160 is subsequently cleaved by a cellular protease to generate the surface (gp120SU) and transmembrane (gp41™) subunits that comprise the envelope protein on the surface of HIV-1 virus particles. A second vector, an example of the viral expression vector, (either pHIVluc or pHIVluc.DELTAA.U3) is designed to express genomic and subgenomic viral RNAs and all HIV proteins except the envelope polyprotein (FIGS. 1A-1B).

In this application, patient-derived segment(s) correspond to the coding region (~2.5 KB) of the HIV-1 envelope polyprotein (gp160) and represent either (a) envelope sequences amplified by the reverse transcription-polymerase chain reaction method CRT-PCR) using viral RNA isolated from virus derived from HIV-infected individuals, or (b) envelope sequences derived from molecular clones of HIV-1 that contain specific mutations introduced by site directed mutagenesis of a parental molecular clone (typically NL4-3).

Isolation of viral RNA was performed using standard procedures (e.g. RNAgents Total RNA Isolation System, Promega, Madison Wis. or RNAzol, Tel-Test, Friendswood, Tex.). The RT-PCR protocol was divided into two steps. A retroviral reverse transcriptase [e.g. Superscript II (Invitrogen, Life Technologies) Moloney MuLV reverse transcriptase (Roche Molecular Systems, Inc., Branchburg, N.J.), or avian myeloblastosis virus (AMV) reverse transcriptase, (Boehringer Mannheim, Indianapolis, Ind.)] was used to copy viral RNA into first strand cDNA. The cDNA was then amplified to high copy number using a thermostable DNA polymerase [e.g. Taq (Roche Molecular Systems, Inc., Branchburg, N.J.), Tth (Roche Molecular Systems, Inc., Branchburg, N.J.), PrimeZyme (isolated from Thermus brockianus, Biometra, Gottingen, Germany)] or a combination of thermostable polymerases as described for the performance of "long PCR" (Barnes, W. M., (1994) Proc. Natl. Acad. Sci, USA 91, 2216-2220) [e.g. Expand High Fidelity PCR System (Taq+Pwo), (Boehringer Mannheim. Indianapolis, Ind.) OR GeneAmp XL PCR kit (Tth+Vent), (Roche Molecular Systems, Inc., Branchburg, N.J.), Advantage-2, (CloneTech).

Oligo-dT was used for reverse transcription of viral RNA into first strand cDNA. Envelope PCR primers, forward primer Xho/Pin and reverse primer Mlu/Xba (Table 3) were used to amplify the patient-derived segments. These primers are designed to amplify the ~2.5 kB envelope gene encoding the gp160 envelope polyprotein, while introducing Xho I and Pin AI recognition sites at the 5' end of the PCR amplification product, and Mlu I and Xba I sites at the 3' end of the PCR amplification product.

Subject derived segments (2.5 kB envelope sequence amplification product) were inserted into HIV-1 envelope expression vectors using restriction endonuclease digestion, DNA ligation and bacterial transformation methods as described in U.S. Pat. No. 5,837,464 (International Publication Number WO 97/27319), with minor adaptations. The ~2.5 kB amplification product was digested with either Xho I or Pin AI at the 5' end and either Mlu I or Xba I at the 3' end. The resulting digestion products were ligated, using DNA ligase, into the 5' Xho I/Pin AI and 3' Mlu I/Xba I sites of modified pCXAS or pCXAT expression vectors. The construction of the pCXAS and pCXAT vectors has been described in U.S. Pat. No. 5,837,464 (International Publication Number WO 97/27319)). Modified pCXAS and pCXAT vectors contain a Pin AI restriction site in addition to the Xho I, Mlul and Xba I restriction sites that exist in pCXAS and pCXAT. The Pin AI site was introduced between the Xho I and Mlu I sites by site directed mutagenesis, such that the four sites are located 5' to 3' in the following order; Xho I, Pin AI, Mlu I and Xba I. In a preferred embodiment, the 2.5 kB amplification products were digested with Pin AI and Mlu I and ligated into the 5' Pin AI site and the 3' Mlu I site of the modified pCXAS expression vector. Ligation reaction products were used to transform $E.\ coli$. Following a 24-36 h incubation period at 30-37.degree. C., the expression vector plasmid DNA was purified from the $E.\ coli$ cultures. To ensure that expression vector preparations adequately represents the HIV quasispecies present in the serum of a given subject, many (>100) independent $E.\ coli$ transformants were pooled and used for the preparations of pHIVenv plasmid DNA. Vectors that are assembled in this manner for the purposes of expressing subject virus derived envelope proteins are collectively referred to as pHIVenv (FIGS. 1 and 3).

The genomic HIV expression vectors pHIVluc and pHIVlucΔU3 are designed to transcribe HIV genomic RNA and subgenomic mRNAs and to express all HIV proteins except the envelope polyprotein (FIG. 1B). In these vectors, a portion of the envelope gene has been deleted to accommodate a functional indicator gene cassette, in this case, "Firefly Luciferase" that is used to monitor the ability of the virus to replicate in the presence or absence of anti-viral drugs. In pHIVlucΔU3, a portion of the 3' U3 region has been deleted to prevent transcription of viral RNAs from the 5' LTR in infected cells.

Susceptibility assays for HIV-1 entry inhibitors were performed using packaging host cells consisting of the human embryonic kidney cell line 293 (Cell Culture Facility, UC San Francisco, SF, Calif.) and target host cells consisting of a human osteosarcoma (HOS) cell line expressing CD4 (HT4) plus CCR5, and CXCR4, or astrocytoma (U-87) cell lines expressing either CD4 and CCR5 or CD4 and CXCR4.

Drug susceptibility testing was performed using pHIVenv and pHIVluc or pHIVlucΔU3. Pseudotyped HIV particles containing envelope proteins encoded by the subject derived segment were produced by transfecting a packaging host cell (HEK 293) with resistance test vector DNA. Virus particles were collected (~48 h) after transfection and are used to infect target cells (HT4/CCR5/CXCR4, or U-87/CD4/CXCR4, or U-87/CD4/CCR5) that express HIV receptors (i.e. CD4) and co-receptors (i.e. CXCR4, CCR5). After infection (~72 h) the target cells are lysed and luciferase activity is measured. HIV must complete one round of replication to successfully infect the target host cell and produce luciferase activity. The amount of luciferase activity detected in the infected cells is used as a direct measure of "infectivity" (FIGS. 1 and 2). If for any reason (e.g. lack of the appropriate receptor or co-receptor, inhibitory drug activity, neutralizing antibody binding), the virus is unable to enter the target cell, luciferase activity is diminished. Drug susceptibility is assessed by comparing the infectivity in the absence of drug to infectivity in the presence of drug. Relative drug susceptibility can be quantified by comparing the susceptibility of the "test" virus to the susceptibility of a well-characterized reference virus (wildtype) derived from a molecular clone of HIV-1, for example NL4-3 or HXB2.

Packaging host cells were seeded in 10-cm-diameter dishes and were transfected one day after plating with pHIVenv and pHIVluc or pHIVlucΔU3. Transfections were performed using a calcium-phosphate co-precipitation procedure. The cell culture media containing the DNA precipitate was replaced with fresh medium, from one to 24 hours, after transfection. Cell culture media containing viral particles was typically harvested 2 days after transfection and was passed through a 0.45-mm filter. Before infection, target cells were plated in cell culture media. Entry inhibitor drugs were typically added to target cells at the time of infection (one day prior to infection on occasion). Typically, 3 days after infection target cells were assayed for luciferase activity using the Steady-Glo reagent (Promega) and a luminometer.

7.2 Example 2

Identifying Envelope Amino Acid Substitutions/Mutations that Alter Susceptibility to Virus Entry Inhibitors This example provides a means and method for identifying mutations in HIV-1 envelope that confer reduced susceptibility/resistance to virus entry inhibitors. This example also provides a means and method for quantifying the degree of reduced susceptibility to entry inhibitors conferred by specific envelope mutations.

Envelope sequences derived from subject samples, or individual clones derived from subject samples, or envelope sequences engineered by site directed mutagenesis to contain specific mutations, were tested in the entry assay to quantify drug susceptibility based on a well-characterized reference standard (e.g. NL4-3, HXB2).

In one embodiment, susceptibility to longitudinal subject samples (viruses collected from the same subject at different timepoints) is evaluated. For example, susceptibility to entry inhibitors is measured prior to initiating therapy, before or after changes in drug treatment, or before or after changes in virologic (RNA copy number), immunologic (CD4 T-cells), or clinical (opportunistic infection) markers of disease progression.

7.2.1 Genotypic Analysis of Subject HIV Samples

Envelope sequences representing subject sample pools, or clones derived from subject pools, can be analyzed by any broadly available DNA sequencing methods. In this example, subject HIV sample sequences were determined using viral RNA purification, RT/PCR and dideoxynucleotide chain terminator sequencing chemistry and capillary gel electrophoresis (Applied Biosystems, Foster City, Calif.). Envelope sequences of subject virus pools or clones were compared to reference sequences and other subject samples. The genotypes of the viruses were examined for sequences that are different from the reference or pre-treatment sequence and correlated to differences in entry inhibitor susceptibility, as described below.

7.2.2 Entry Inhibitor Susceptibility of Site Directed Mutants

Genotypic changes that correlate with changes in fitness are evaluated by constructing envelope expression vectors (pHIVenv) containing the specific mutation on a defined, drug susceptible, genetic background (e.g. NL4-3 reference strain). Mutations may be incorporated alone and/or in combination with other mutations that are thought to modulate the entry inhibitor susceptibility. Envelope mutations are introduced into pHIVenv vectors using any of the broadly available methods for site-directed mutagenesis. In certain embodiments the mega-primer PCR method for site-directed mutagenesis is used (Sarkar, G. and Summer, S. S., 1990). A pHIVenv vector containing a specific envelope mutation or group of mutations are tested using the virus entry assay described in Example 1. Drug susceptibility of the virus containing envelope mutations is compared to the drug susceptibility of a genetically defined drug susceptible virus that lacks the specific mutations under evaluation. Observed changes in entry inhibitor susceptibility are attributed to the specific mutations introduced into the pHIVenv vector.

7.3 Example 3

Measuring Susceptibility to Virus Entry Inhibitors to Guide Treatment Decisions

This example provides a means and method for using virus entry inhibitor susceptibility to guide the treatment of HIV-1. This example further provides a means and method for using virus entry inhibitor susceptibility to guide the treatment of subjects that have received previous antiretroviral treatment with a virus entry inhibitor. This invention further provides the means and methods for using virus entry inhibitor susceptibility to guide the treatment of subjects that have not received previous treatment with a virus entry inhibitor.

In one embodiment, the susceptibility of subject's viruses to virus entry inhibitors is used to guide the treatment of subjects failing antiretroviral regimens that include one or more virus entry inhibitors. Treatment failure (also referred to as virologic failure) is generally defined as partially suppressive antiviral treatment resulting in detectable levels of virus, which is typically measured in the subject plasma). Guidance may include, but is not limited to, (a) clarification of available drug treatment options, (b) selection of more active treatment regimens, (c) clarification of the etiology of rising viral load in treated subjects (i.e. poor adherence, drug resistance), and (d) reduction in the use of inactive and potentially toxic drugs. In this embodiment, resistance test vectors are derived from a subject virus samples and tested for susceptibility to various virus entry inhibitors using the phenotypic virus entry assay. Virus entry inhibitors may include, but are not limited to, fusion inhibitors (e.g. T-20, T-1249), co-receptors antagonists (AMD3100, AMD8664, TAK779, PRO542, and peperidin-lyl butane compounds) and CD4 antagonists (MAb B4). Appropriate treatment decisions are based on the results of the virus entry assay (e.g. see FIG. 4B) and additional relevant laboratory test results and clinical information.

In another embodiment, the susceptibility of subject's viruses to virus entry inhibitors is used to guide the treatment of subjects that have not been previously treated with antiretroviral regimens that include one or more virus entry inhibitors. Guidance may include, but is not limited to, (a) clarification of available drug treatment options, (b) selection of more active treatment regimens, (c) clarification of the baseline susceptibility to virus entry inhibitors, and (d) reduction in the use of inactive and potentially toxic drugs. Determining baseline susceptibility of virus entry inhibitors in treatment naive subjects is important for two reasons. First, the natural susceptibility of viruses to entry inhibitors can vary widely (e.g. see FIG. 4A). Second, the increased use of virus entry inhibitors will undoubtedly result in the generation of drug resistant variants that can be transmitted to newly infected individuals. In this embodiment, resistance test vectors are derived from a subject virus samples and tested for susceptibility to various virus entry inhibitors using the phenotypic virus entry assay. Virus entry inhibitors may include, but are not limited to, fusion inhibitors (e.g. T-20, T-1249), co-receptors antagonist (e.g. AMD3100, AMD8664, TAK-355, PRO542, and peperidin-lyl butane compounds) and CD4 antagonists (MAb 5A8). Appropriate treatment decisions are based on the results of the virus entry assay and additional relevant laboratory test results and clinical information.

7.4 Example 4

Assays Assessing Fusogenicity of HIV Envelope Proteins

This example provides means and methods for determining the fusogenicity, e.g., the propensity of a virus to mediate aggregation of susceptible cells and fusion of their membranes to form syncytia, of a virus's envelope protein. Briefly, nucleic acids encoding HIV-1 envelope proteins were amplified from patient plasma and introduced to an expression vector as described above in Example 1. See FIG. 5. Membrane fusion was measured by co-culturing HEK-293 cells transiently transfected with an HIV genomic vector comprising a deletion of the env gene (similar to pHIVluc, described above, but lacking luciferase activity) and the expression vector and CD4/CCR5/CXCR4-positive 5.25 cells transformed with plasmids expressing both green fluorescent protein (GFP) and luciferase under control of the HIV-1 long terminal repeat (LTR). Fusion was visualized by detecting GFP activity and quantified by determining amounts of luciferase activity.

More specifically, the fusion assay was developed by replacing the U87 target cell line used in the entry assay with the 5.25.Luc4.M7 cell line. The 5.25.Luc4.M7 cell line was derived from the CEMX174 cell line and contains green fluorescent protein (GFP) and firefly luciferase (LUC) reporter genes. GFP and LUC expression in 5.25.Luc4.M7 cells is regulated by tat-induction of the HIV-1 LTR. The fusion assay was performed by co-transfecting 293 effector cells with an envelope deleted HIV genomic vector plus an HIV envelope expression vector. At 48 hours post-transfection, the 293 effector cells were harvested, washed thoroughly to remove virus particles, and added to 5.25.Luc4.M7 target cell cultures in the presence of a reverse transcriptase inhibitor to inhibit virus replication. Membrane fusion was triggered in the co-cultures by the interaction of the HIV envelope protein produced in the 293 effector cells with the CD4, CCR5 and/or CXCR4 expressed on the surface of the 5.25.Luc4.M7 target cells. The tat protein derived from the effector cells trans-activates the GFP and LUC reporter genes. In this assay, cell-cell fusion can be observed directly using fluorescence microscopy to view GFP expression, and can be accurately quantified using luciferase (or immuno-chemical detection of GFP).

7.5 Example 5

Identifying Determinants of Fusogenicity or Resistance to Entry Inhibitors

This example provides methods and compositions for determining increased or decreased fusogenicity and/or increased or decreased susceptibility to viral entry inhibitors. Binding and entry of appropriate cells was assessed as described in Example 1, while fusogenicity was tested as described in Example 4. To determine genotypes of the envelope proteins for which entry and fusogenicity phenotypes were determined, envelope gene sequences were determined using viral RNA purification, RT/PCR and ABI chain terminator automated sequencing according to conventional protocols as described in Example 2.

To define genetic and structural determinants that confer differential sensitivity to CD4-gp120 inhibition and membrane fusion, 16 envelope molecular clones derived from a virus population infecting a single patient were sequenced as described above and tested for susceptibility to entry inhibitors and for fusogenicity. In particular, susceptibility to CD4 binding site inhibitors (PRO542, a soluble form of CD4; Progenics Pharmaceuticals, Inc.; Tarrytown, N.Y.; and IgG-b12; Scripps Research Institute; La Jolla, Calif.) and anti-CD4 monoclonal antibody B4 (United BioMedical, Inc.; Hauppauge, N.Y.) was assessed using these assays. In addition, the envelope genes of these sixteen clones were sequenced as described above and the sequence of the encoded envelope protein was deduced. Phylogenetic analysis revealed two related virus populations that segregated based on sensitivity to CD4-gp120 inhibitors. In summary, clonal and chimeric envelopes containing shorter gp120 variable loops and fewer glycosylation sites exhibited increased susceptibility to CD4-binding site inhibitors PRO542 and IgG-b12 but decreased susceptibility to the anti-CD4 monoclonal antibody B4. Further, the envelopes containing shorter gp120 variable loops induced higher levels of membrane fusion.

First, the sensitivity of the 16 different clones to the three different entry inhibitors was assessed using the methods described in Example 1. As shown in FIG. 6, the sixteen clones exhibited increasing resistance to the anti-CD4 mAb B4 from clone 1 to clone 16. Sensitivity to TNX-355 and PRO542 generally varied inversely to sensitivity to B4. Further, fusogenicity generally corresponded to sensitivity to B4 and varied inversely to sensitivity to TNX 355 and PRO542. Two samples, clones 1 and 4, exhibited altered susceptibility to PRO542 that did not correlate well with resistance to TNX 355 and susceptibility to B4; these clones are believed to have an as-yet uncharacterized mutation that is believed to cause resistance to TNX 355 in an otherwise susceptible genetic background. Experiments to identify the genetic determinants of TNX 355 resistance in these clones are presently ongoing.

To assess the genetic basis of the differences in susceptibility observed in the sixteen clones, the sequences of the envelope genes encoding the envelope proteins of the sixteen clones were determined and compared. At the outset, it should be noted that the sixteen clones of FIG. 6 are the same as the clones of FIG. 7-9. The correspondence of the clones is as follows: clone 1 of FIG. 6 is clone 43 of FIGS. 7-9; clone 2 of FIG. 6 is clone 24 of FIGS. 7-9; clone 3 of FIG. 6 is clone 11 of FIGS. 7-9; clone 4 of FIG. 6 is clone 36 of FIGS. 7-9; clone 5 of FIG. 6 is clone 26 of FIGS. 7-9; clone 6 of FIG. 6 is clone 6 of FIGS. 7-9; clone 7 of FIG. 6 is clone 21 of FIGS. 7-9; clone 8 of FIG. 6 is clone 3 of FIGS. 7-9; clone 9 of FIG. 6 is clone 18 of FIGS. 7-9; clone 10 of FIG. 6 is clone 17 of FIGS. 7-9; clone 11 of FIG. 6 is clone 35 of FIGS. 7-9; clone 12 of FIG. 6 is clone 20 of FIGS. 7-9; clone 13 of FIG. 6 is clone 5 of FIGS. 7-9; clone 14 of FIG. 6 is clone 48 of FIGS. 7-9; clone 15 of FIG. 6 is clone 47 of FIGS. 7-9; and clone 16 of FIG. 6 is clone 39 of FIGS. 7-9.

FIG. 7 presents an alignment of variable region 1 (V1) of the envelope proteins of the sixteen samples. As shown in FIG. 7, the 11 clones that exhibited increased fusogenicity, sensitivity to PRO542, and resistance to B4 had shorter variable regions than the 5 clones that exhibited increased fusogenicity, sensitivity to PRO542, and resistance to B4.

In addition, the differences in length of the V1 region between the two sets of clones altered the distances between glycosylation sites in the region. As is well-known in the art, HIV envelope protein is heavily glycosylated at well-defined positions. The motif that is glycosylated can be represented with the formula N—X-T/S—X, where N is asparagine, T is threonine, S is serine, and X is any amino acid that is not proline. The T or S residue in the motif is the point of attachment for N-linked glycosylation. The glycosylation sites in variable regions of the HIV envelope protein shown in the figures are indicated with bold type. As shown in FIG. 7, the length present in the less fusogenic, resistant to PRO542, and sensitive to B4 clones results in separation of glycosylation sites by an additional 23 amino acids relative to more fusogenic, sensitive to PRO542, and resistant to B4 clones. This separation of the glycosylation sites may additionally contribute to the phenotypes observed for the less fusogenic, resistant to PRO542, and sensitive to B4 clones.

Further, the sequences of variable region 4 (V4) of the sixteen clones' envelope proteins were also aligned as shown in FIG. 8. As shown in FIG. 8, clones more fusogenic, sensitive to PRO542, and resistant to B4 had slightly shorter V4 regions relative to less fusogenic, resistant to PRO542, and sensitive to B4 clones. Further, several of the more fusogenic, sensitive to PRO542, and resistant to B4 clones comprised mutations that eliminated glycosylation motifs present in the less fusogenic, resistant to PRO542, and sensitive to B4 clones. For example, the last two clones (identified as clones 36 and 43), which were resistant to PRO542 and sensitive to B4, comprised two glycosylation sites not present in the first 11 clones (clones 3, 20, 39, 47, 48, 18, 17, 35, 11, 24, and 5). In addition, the V4 region of the last two clones (clones 36 and 43) were three amino acids longer than the V4 regions of the first 11 clones, again indicating that the length of the variable regions of the envelope protein affects fusogenicity, sensitivity to PRO542, and resistance to B4. However, the twelfth through fourteenth clones (clones 21, 26, and 6) comprised only one glycosylation motif not present in the first 11 clones and were the same length as the first 11 clones.

Alignments of variable region 5 (V5) of the sixteen clones' envelope proteins are presented as FIG. 9. Similar to the observations for the V1 and V4 regions, clones more fusogenic, sensitive to PRO542, and resistant to B4 had slightly shorter V5 regions relative to less fusogenic, resistant to PRO542, and sensitive to B4 clones. Further, the residues present in the less fusogenic, resistant to PRO542, and sensitive to B4 clones added a glycosylation motif not present in the more fusogenic, sensitive to PRO542, and resistant to B4 clones. Thus, consistent with the observations from the V1 and V4 regions, added length to the V5 regions and/or additional glycosylation motifs present in the V5 region resulted in less fusion, resistance to PRO542, and sensitivity to B4.

To explore the relative contributions of length and glycosylation to this phenomenon, several recombinant clones were constructed. In general, the recombinant clones were constructed by swapping the V5 region of different clones using conventional techniques. The results of these swapping experiments are shown in FIGS. 10-13. FIG. 10 presents the effects of a domain swapping experiment on fusogenicity and PRO542 sensitivity. Three strains, A, B, and C, served as the basis for the experiment presented in FIG. 10; strain A is resistant to PRO542 and exhibits low fusogenicity, strain B is sensitive to PRO542 and exhibits high fusogenicity, and strain C is moderately sensitive to PRO542 and exhibits low fusogenicity. The portion of the V5 region shown in FIG. 10 from strain B was swapped into the remainder of the envelope protein from strains A and C, respectively. As shown in FIG. 10, swapping this portion of strain B's V5 region into strain A and C to form strains A' and C' both shortens the V5 region and destroys a glycosylation site. As also shown in FIG. 10, strain A' exhibits increased sensitivity to PRO542 and increased fusogenicity relative to strain A, demonstrating that shortening of the V5 region and/or deletion of a glycosylation site results in increased sensitivity to PRO542 and increased fusogenicity. Similarly, strain C' also exhibits increased sensitivity to PRO542 and increased fusogenicity relative to strain C, confirming this result.

To assess whether the phenotypic differences observed between strain A and strain C result from the different sequences present in V5 in these strains (seen in FIG. 10) or from differences in other envelope regions, two additional constructs, strains B' and B" were constructed. Strain B' was constructed to contain the V5 region of strain A in an otherwise strain B background, and strain B" was constructed to contain the V5 region of strain C in an otherwise strain B background. As shown in FIG. 11, strains B' and B" exhibit essentially identical susceptibility to PRO542 and fusogenicity, demonstrating that differences between strain A's and strain C's susceptibility to PRO542 and fusogenicity result from differences in the envelope protein other than in V5. Thus, the sequence variation observed in V5 between strain A and strain C does not appear to affect susceptibility to PRO542 and fusogenicity; rather, the presence or absence of the additional length and/or glycosylation site in V5 was responsible for the differences observed between strains A and C and strain B.

Two additional strains, $B^1$ and $B^4$, Were constructed. As shown in FIG. 12, strains $B^3$ and $B^4$ were constructed to comprise altered V5 regions: strain $B^3$ includes four amino acids in V5 that are not present in strain B but do encode not a glycosylation site, while strain B includes four amino acids not present in strain B and also comprises an extra glycosylation site. As shown in FIG. 11, strains $B^3$ and $B^4$ each exhibit substantially reduced fusogenicity relative to strain B, while strain $B^4$ exhibits reduced sensitivity to PRO542. Interestingly, strain B' exhibits further reductions in fusogenicity and sensitivity to PRO542, indicating that such phenotypes can also be influenced by the sequence present in the V5 region. Nonetheless, FIG. 11 demonstrates that additional length and/or additional glycosylation sites in V5 resulted in reduced fusogenicity and increased resistance to PRO 542.

Finally, two clones presented in FIG. 6 exhibited divergent results from the remainder of the clones and were therefore subjected to further analysis. In particular, clones 2 and 3 (clones 24 and 11 in the alignments of FIG. 7-9) were predicted to be sensitive to PRO542 based on their relative lack of glycosylation and short variable loops. However, both clones 2 and 3 were resistant to PRO542 (see FIG. 6). Genotypic analysis revealed that both clones 1 and 4 contained a single mutation in constant region 2 (C2) of the envelope protein (L261S) that was not present in other clones with V1, V4, and V5 similar to those of clones 1 and 4. Position 261 in this clone corresponds to amino acid 262 the envelope protein of a reference HIV strain, NL4-3 (Accession No. AAB60578).

To assess the role of the L261S mutation in suppressing the PRO542-sensitive phenotype of viruses with short variable regions and/or few glycosylation sites, a recombinant envelope gene was constructed that comprised the wild-type residue at position 261 of C2 in the same genetic background as clone 3 of FIG. 6 (Clone 11 of FIGS. 7-9). Reversion of the L261S mutation to wild-type restored sensitivity to PRO542 of clone 3, as shown in FIG. 13. Thus, clones 2 and 3 both had short variable regions and few glycosylation sites in those regions, like, for example, clone 1, but L261S in clones 2 and 3 suppressed the PRO542-sensitive phenotype predicted from the short variable regions and few glycosylation sites.

7.6 Example 6

Characterization of Determinants for Fusogenicity and Resistance to Entry Inhibitors This example describes the results of experiments designed to identify and characterize particular molecular determinants for fusogenicity, infectivity, and resistance to entry inhibitors. In the experiments, individual patient-derived envelope genes prepared according to Example 1 were characterized as described in Examples 2, 3, and 4. To assess the relative contributions of mutations present in gp120 and/or gp41 to altered fusogenicity, infectivity, and susceptibility to entry inhibitors, chimeric envelope genes were constructed to encode a portion of the gp120 from one envelope gene isolate while holding the remainder of the gene constant. To ensure that no unrecognized mutations were introduced through this procedure, the nucleotide sequences of the recombinant clones were verified as described in Example 2. The results of these experiments are presented in Tables 4-Y, below. In the Tables, infectivity results are presented as a raw number of relative fluorescence units observed, fusogenicity is presented as a percentage of fusogenicity observed relative to reference strain HXB2, and susceptibility to a representative entry inhibitor, PRO542, is presented as the $IC_{50}$.

In the experiments presented in Table 4, the interaction between the L261S mutation and mutations at positions 639 and 749 were tested. First, the envelope gene sequences of two clones (clone 4 and clone 5) from a single patient were determined as described above. The envelope proteins encoded by these genes had identical sequences except for variance at positions 261, 639, and 749, numbered as the residues are found in the gp160 polyprotein. The numbering of these residues corresponds to the numbering found in reference strain HXB2 (Accession No. AAB50262).

TABLE 4

| | | | | | | Phenotypes | | |
|---|---|---|---|---|---|---|---|---|
| | gp120 | | gp41 | | | | | PRO 542 |
| Clone ID | 261 | mutations | 639 | 749 | mutations | RFU | Fusion, % | (IC50 ug/ml) |
| Clone 4 | S | L261S | T | V | | 135,982 | 1 | 53.7 |
| Clone 5 | L | | A | A | T639A, V749A | 542,286 | 18 | 1.09 |
| Clone 6 | L | | T | V | | 680,088 | 34 | 0.42 |
| Clone 7 | S | L261S | A | A | T639A, V749A | 237,648 | 7 | 0.40 |
| HXB2 | L | | T | V | | | | |

The residues at these positions, together with data showing infectivity (RFU), fusogenicity, and $IC_{50}$ for PRO542 shown in Table 4. Also shown in Table 4 is the amino acid found at these positions in reference strain HXB2. To confirm the effects of the L261S mutation on infectivity, fusogenicity, and susceptibility to PRO542, the portion of the envelope gene from clone 5 comprising the 261 position was introduced into clone 4 to form clone 6. As shown in Table 4, reversion of L261S to L resulted in increased infectivity, fusogenicity, and susceptibility to PRO542 relative to clone 4.

To test the interactions between mutations at position 261 and positions 639 and 749, the portion of the envelope gene comprising the L261S mutation from clone 4 was introduced into clone 5 to form clone 7. As shown in Table 4, combination of the L261S mutation with T639A and V749A resulted in increased infectivity, fusogenicity, and susceptibility to PRO 542 relative to clone 4, containing the L261S mutation alone. Thus, the combination of T639A and V749A appears to suppress the reduced infectivity, fusogenicity, and susceptibility to PRO542 phenotypes observed for the L261S mutation.

In another set of experiments, the interactions between variants at positions 117, 421, 741, and 854 were assessed. The residues present at these positions and the infectivity, fusogenicity, and susceptibility to PRO542 phenotypes are presented in Table 5.

Clones 8 and 9 were each single clones isolated from a patient. The clones were identical except for the variance at positions 117, 421, 741, and 854 as shown in Table 5, above. Clone 8 comprised three mutations, K117E, K421E, and I854P, and exhibited reduced infectivity and fusogenicity and increased susceptibility to PRO542 relative to Clone 9. Clone 9 comprised two mutations relative to HXB2, D741G and I854L.

To assess the relative contributions of the variant amino acids, clones 10, 11, 12, and 13 were constructed by cloning appropriate portions of clone 8 into a clone 9 background, or vice versa. First, the effects of the D741G mutation were assessed by comparing clone 10 to clone 9. As shown in Table 5, this mutation does not appear to significantly affect any of the tested phenotypes in the tested genetic background.

Next, the effects of the K117E and K421E mutations were tested by comparing clones 11, 12, and 13 to clone 10. As shown in Table 5, the K117E mutation alone (clone 11) resulted in reduced infectivity, fusogenicity, and PRO542 susceptibility relative to clone 10. The K421E mutation alone (clone 13) resulted in reduced infectivity and fusogenicity relative to clone 10; the $IC_{50}$ for PRO542 could not be determined for this clone because of its very low infectivity. The combination of K117E and K421E (clone 12) resulted in reduced infectivity and fusogenicity but increased PRO542 susceptibility relative to clone 10.

In another set of experiments, the relative contributions of variance at positions 121 and 298 were assessed for the same phenotypes as described above. The results of these experiments are presented in Table 6.

TABLE 5

| | gp120 | | | gp41 | | | Phenotypes | | |
|---|---|---|---|---|---|---|---|---|---|
| | | | | | | | | | PRO 542 |
| Clone ID | 117 | 421 | mutations | 741 | 854 | mutations | RFU | Fusion, % | (IC50 ug/ml) |
| clone 8 | E | E | K117E, K421E | D | P | I854P | 9,855 | 2 | 0.0062 |
| clone 9 | K | K | | G | L | D741G, I854L | 599,179 | 46 | 0.27 |
| clone 10 | K | K | | D | L | I854L | 680,088 | 34 | 0.42 |
| clone 11 | E | K | K117E | D | L | I854L | 17,931 | 1 | 4.00 |
| clone 12 | E | E | K117E, K421E | D | L | I854L | 8,377 | 2 | 0.0055 |
| clone 13 | K | E | K421E | D | L | I854L | 1,310 | 1 | DNR |
| HXB2 | K | K | | D | I | | | | |

TABLE 6

| | gp120 | | | Phenotypes | | |
|---|---|---|---|---|---|---|
| Clone ID | 121 | 298 | mutations | RFU | Fusion, % | PRO 542 (IC50 ug/ml) |
| clone 14 | K | G | R298G | 6,938 | 19 | 0.0082 |
| clone 15 | E | R | K121E | 96,981 | 1 | 70.0 |
| clone 16 | K | R | | 144,580 | 2 | 33.5 |
| clone 17 | E | G | K121E, R298G | 71,151 | 3 | 0.023 |
| clone 18 | K | G | R298G | 113,619 | 18 | 0.0055 |
| clone 19 | E | G | K121E, R298G | 7,687 | 14 | 0.010 |
| clone 20 | K | R | | 192,028 | 3 | 16.0 |
| HXB2 | K | R | | | | |

Next, clone 19 was constructed by replacing the region of clone 14 comprising position 298 with the corresponding region from clone 15. Clone 19 exhibited relatively similar infectivity, fusogenicity, and susceptibility to clone 14. Finally, clone 20 was constructed by was constructed by replacing the region of clone 14 comprising position 121 with the corresponding region from clone 15. Clone 20 exhibited increased infectivity and reduced fusogenicity and susceptibility to PRO542 relative to clone 14. Thus, reversion of the K121E mutation in the genetic background of clone 14 resulted in increased infectivity and reduced fusogenicity and susceptibility to PRO542.

Next the effects of pairs of mutations at positions 164 and 165 and at positions 344 and 346 were compared in a series of experiments summarized in Table 7, below.

TABLE 7

| | gp120 | | | Phenotypes | | |
|---|---|---|---|---|---|---|
| Clone ID | 164, 165 | 344, 346 | mutations | RFU | Fusion, % | PRO 542 (IC50 ug/ml) |
| Clone 21 | II | RA | S164I, Q344R | 25,409 | 74 | 0.034 |
| Clone 22 | VV | QV | S164V, I165V, A346V | 146,086 | 25 | 4.64 |
| Clone 23 | VV | RA | S164V, I165V, Q344R | 261,832 | 51 | 0.68 |
| Clone 24 | II | QV | A164V, I165V, A346V | 107,502 | 53 | 2.03 |
| Clone 25 | II | QV | S164I, A346V | 76,813 | 46 | 0.050 |
| Clone 26 | II | RA | S164I, Q344R | 78,126 | 90 | 0.038 |
| HXB2 | SI | QA | | | | |

Clones 14 and 15 were each single envelope clones isolated from the same patient. To begin to assess the relative contributions of the mutations observed in clones 14 and 15 (R298G and K121E, respectively), a series of chimeric envelope genes were constructed and their phenotypes determined as described above. As shown in Table 6, clone 14 exhibits reduced infectivity, increased fusogenicity, and increased susceptibility to PRO542 relative to clone 15.

First, clone 16 was constructed by replacing the region of clone 15 comprising position 121 with the corresponding region from clone 14. Reversion of the K121E mutation to wild-type in the clone 15 background resulted in increased infectivity, fusogenicity, and susceptibility to PRO542 relative to clone 15. Next, clone 17 was constructed by replacing the region of clone 15 comprising position 298 with the corresponding region from clone 14. The combination of the K121E mutation and the R298G mutation resulted in decreased infectivity, increased fusogenicity, and greatly increased susceptibility to PRO542 relative to clone 15. To confirm that the change in fusogenicity and susceptibility to PRO542 resulted from the K121E, mutation and not some other difference in envelope, clone 18 was constructed by cloning the region of clone 14 comprising positions 121 and 298 into clone 15. As expected, clone 18 showed increased fusogenicity and susceptibility to PRO542 relative to clone 15. Interestingly, clone 18 exhibited substantially increased infectivity relative to clone 14.

Clones 21 and 22 were each single envelope clones isolated from the same patient. To begin to assess the relative contributions of the mutations present in clones 21 and 22 to the infectivity, fusogenicity, and susceptibility to PRO542, clones 23-26 were constructed. First, clone 23 was constructed by cloning the region of clone 22 comprising residues 164 and 165 into a clone 21 background. As shown in Table 7, changing S164I to S164V and I165 to I165V resulted in an increase in infectivity, a decrease in fusogenicity, and a decrease in PRO542 susceptibility relative to clone 21. Next, clone 24 was constructed by cloning the region of clone 22 comprising positions 344 and 346 into clone 21. As shown in Table 7, reverting the Q344R mutation to wild-type while introducing the A346V mutation resulted in increased infectivity, decreased fusogenicity, and decreased susceptibility to PRO542 relative to clone 21.

Next, clone 25 was constructed by cloning the region of clone 21 comprising residues 164 and 165 into a clone 22 background. As shown in Table 7, the changing from S164V and I165V to S164I and I165 resulted in a decrease in infectivity, an increase in fusogenicity, and an increase in PRO542 susceptibility relative to clone 22. Clone 26 was constructed by cloning the region of clone 21 comprising positions 164 and 165 into clone 22. As shown in Table 7, introducing the S164I mutation and reverting the I165V mutation to wild-type resulted in decreased infectivity, increased fusogenicity, and increased susceptibility to PRO 542 relative to clone 22.

Finally, the infectivity, fusogenicity, and PRO542 susceptibility of two envelope clones isolated from the same patient were assessed in the same gp120 background. The gp41 genotypes of clones 27 and 28 are presented in Table 8, while as the infectivity, fusogenicity, and PRO542 susceptibility phenotypes are presented in Table 9.

TABLE 8

|  | 536 | 592 | 601 | 617 | 621 | 630 | 633 | 640 | 668 | 674 | 683 | 721 | 833 | 835 |
|---|---|---|---|---|---|---|---|---|---|---|---|---|---|---|
| clone 27 | M | L | K | K | K | E | R | D | S | N | K | H | V | G |
| clone 28 | T | F | R | R | E | Q | K | N | N | S | R | R | L | R |
| HXB2 | T | L | K | K | Q | E | R | S | S | S | K | L | V | G |

TABLE 9

|  | RFU | Fusion, % | PRO 542 (IC50 ug/ml) |
|---|---|---|---|
| Clone 27 | 58,149 | 21 | 0.04 |
| Clone 28 | 56,767 | 1 | 20.6 |

8. REFERENCES

Adachi, A., H. E. Gendelman, S. Koenig, T. Folks, R. Caney, A. Rabson, and M. A. Martin. 1986. Production of Acquired Immunodeficiency Syndrome-associated Retrovirus in Human and Nonhuman Cells Transfected with an Infectious Molecular Clone. J. Virol. 59:284-291.

Alkhatib, G., C. Combadiere, C. C. Broder, Y. Feng, P. E. Kennedy, P. M. Murphy, and E. A. Berger. 1996. CC CKR5: A Rantes, MIP-lalpha, MIP-1 Beta Receptor as a Fusion Cofactor for Macrophage-tropic HIV-1. Science 272:1955-8.

Allaway G. P., Ryder A. M., Beaudry G. A., and Maddon P. J. 1993. Synergistic Inhibition of HIV-1 Envelope-Mediated Cell Fusion by CD4-based Molecules in Combination with Antibodies to Gp120 or Gp41. Aids Res. Hum. Retroviruses 9:581-7.

Baba, M., O. Nishimura, N. Kanzaki, M. Okamoto, H. Sawada, Y. Iizawa, M. Shiraishi, Y. Aramaki, K. Okonogi, Y. Ogawa, K. Meguro, and M. Fujino. 1999. A Small-molecule, Nonpeptide CCR5 Antagonist with Highly Potent and Selective Anti-hiv-1 Activity. Proc. Natl. Acad. Sci. USA 96:5698-703.

Baxter, J., D. Mayers, D. Wentworth, J. Neaton, and T. Merigan. 1999. A Pilot Study of the Short-term Effects of Antiretroviral Management Based on Plasma Genotypic Antiretroviral Resistance Testing (Gart) in Subjects Failing Antiretroviral Therapy. Presented at the 6th Conference on Retroviruses and Opportunistic Infections. Chicago, Ill.

N., and Couturier M. 1993. The F Plasmid CcdB protein Induces Efficient ATP-dependent Dna Cleavage by Gyrase. J Mol. Biol. 23:534-41.

Bernard, P. and Couturier, M. 1992. Cell Killing by the F Plasmid Ccdb protein Involves Poisoning of DNAtopoisomerase II Complexes. J. Mol. Bio. 226:735-45.

Bleul, C. C., M. Farzan, H. Choe, C. Parolin, I. Clark-Lewis, J. Sodroski, and T. A. Springer. 1996. The Lymphocyte Chemoattractant Sdf-1 Is a Ligand for Lestr/fusin and Blocks Hiv-1 Entry. Nature 382:829-33.

Bridger G. J, Skerlj R. T., Padmanabhan S., Martellucci S. A., Henson G. W., Struyf S., Witvrouw M., Schols D., and De Clercq E. 1999. Synthesis and Structure-activity Relationships of Phenylenebis(methylene)-linked Bis-azamacrocycles That Inhibit HIV-1 and HIV-2 Replication by Antagonism of the Chemokine Receptor CXCR4. J. Med. Chem. 42:3971-81.

Carpenter, C. J., Cooper D. A., Fischl, M. A., Gatell J. M., Gazzard B. G., Hammer S. M., Hirsch M. S., Jacobsen D. M., Katzenstein D. A., Montaner J. S., Richman D., Saag M. S., Schechter M., Schooley R. T., Thompson M. A., Vello S., Yeni P. G., and Volberding P. A. 2000. Antiretroviral Therapy in Adults. JAMA 283:381-89.

CDC (Centers for Disease Control and Prevention). HIV/AIDS Surveillance Report, 1999; 11(no. 1).

Coffin, J. M. 1995. HIV Population Dynamics in Vivo: Implications for Genetic Variation, Pathogenesis, and Therapy. Science 267:483-489.

DHHS (Department of Health and Human Services). Henry Kaiser Family Foundation: Guidelines for the Use of Antiretrovirals Agents in HIV-infected Adults and Adolescents. (Jan. 28, 2000).

Gerdes, K., L. K. Poulsen. T. Thisted, A. K. Nielson, J. Martinussen, and P. H. Andreasen. 1990. The Hok Killer Gene Family in Gram-negative Bacteria. The New Biologist: 2:946-956.

Hertogs, K., M. P. De Bethune, V. Miller, T. Ivens, P. Schel, A. V. Cauwenberge, C. Van Den Eynde, V. Van Gerwen, H. Azijn, M. Van Houtte, F. Peeters, S. Staszewski, M. Conant, S. Bloor, S. Kemp, B. Larder, and R. Pauwels. 1998. A Rapid Method for Simultaneous Detection of Phenotypic Resistance to Inhibitors of protease and Reverse Transcriptase in Recombinant Human Immunodeficiency Virus Type 1 Isolates from Subjects Treated with Antiretroviral Drugs. Antimicrob. Agents Chemother. 42:269-276.

Hwang, J.-j., L. Li, W. f. Anderson. 1997. A Conditional Self-inactivating Retrovirus Vector That Uses a Tetracycline-responsive Expression System. J. Virol. 71: 7128-7131.

Japour, A. J., D. L. Mayers, V. A. Johnson, D. R. Kuritzkes, L. A. Beckett, J. M. Arduino, J. Lane, B. R. J., P. S. Reichelderfer, R. T. D-aquila, C. S. Crumpacker, T.R.-S. Group, T.A.C.T. Group, and V. C.R.W. Group. 1993. Standardized Peripheral Blood Mononuclear Cell Culture Assay for Determination of Drug Susceptibilities of Clinical Human Immunodefiency Virus Type 1 Isolates. Antimicrob. Agents Chemother. 37:1095-1101.

Judice J. K., Tom J. Y., Huang W., Wrin T., Vennari J., Petropoulos C. J., and Mcdowell R. S. 1997. Inhibition HIV Type 1 Infectivity by Constrained Alphahelical Peptides: Implications for the Viral Fusion Mechanism. Proc. Natl. Acad. Sci. USA 94:13426-30.

Kilby J M, Hopkins S, Venetta Tm, Dimassimo B, Cloud Ga, Lee Jy, Alldrdge L, Hunter E, Lambert D, Bolognesi D, Matthews T, Johnson Mr. Nowak Ma, Shaw Gm, and Saag Ms. 1998. Potent Suppression of HIV-1 Replication in Humans by T-20, a Peptide Inhibitor of Gp41-mediated Virus Entry. Nat Med. 4:1302-7.

Mascola, J. R., G. Stiegler, T. C. Vancott, H. Katinger, C. B. Carpenter, C. E. Hanson, H. Beary, D. Hayes, S. S. Frankel, D. L. Birx, and M. G. Lewis. 2000. Protection of Macaques Against Vaginal Transmission of a Pathogenic HIV-1/siv Chimeric Virus by Passive Infusion of Neutralizing Antibodies. Nature Med. 6:207-210.

Miyoshi, H., B. Ulrike, M. Takahashi, F. H. Gage, and I. M. Verma. 1998. Development of a Self-inactivating Lentivirus Vector. J. Virol. 72:8150-5157.

Naviaux, R. K., E. Costanzi, M. Haas, and I. M. Verma. 1996. The Pcl Vector System: Rapid production of Helper-free, High-titer, Recombinant Retroviruses. J. Virol. 70: 5701-5705.

Petropoulos, C. J., N. T. Parkin, K. L. Limoli, Y. S. Lie, T. Wrin, W. Huang, H. Tian, D. Smith, G. A. Winslow, D. Capon and J. M. Whitcomb. 2000. A Novel Phenotypic Drug Susceptibility Assay for HIV-1. Antimicrob. Agents & Chem. 44:920-928.

Phrma (Pharmaceutical Research and Manufacturers of America). New Medicines in Development for Aids 1999.

Piketty, C., E. Race, P. Castiel, L. Belec, G. Peytavin, A. si-mohamed, G. Gonzalez-canali, L. Weiss, F. Clavel, and M. Kazatchkine. 1999. Efficacy of a Five-drug Combination Including Ritonavir, Saquinavir and Efavirenz in Subjects Who Failed on a Conventional Triple-drug Regimen: Phenotypic Resistance to protease Inhibitors predicts Outcome of Therapy. Aids: 13:f71-f77.

Porter, C. C., K. V. Lukacs, G. Box, Y. Takeuchi, and M. K. L. Collins. 1998. Cationic Liposomes Enhance the Rate of Transduction by a Recombinant Retroviral Vector in Vitro and in Vivo. J. Virol. 72:4832-4840.

Reimann K. A., Cate R. L., Wu Y., Palmer L., Olson D., Waite B. C., Letvin N. L., and Burkly L. C. 1995. In Vivo Administration of CD4-specific Monoclonal Antibody: Effect on provirus Load in Rhesus Monkeys Chronically Infected with the Simian Immunodeficiency Virus of Macaques. Aids Res. Hum. Retroviruses 11:517-25.

Retroviruses. Coffin, J., S. Hughes, H. Varmus (Eds). 1997. Cold Spring Harbor Laboratory Press, Cold Spring Harbor, N.Y.

Richman, D. 1998. Nailing down Another HIV Target. Nature Med. 4:1232-1233.

Rimsky, L. T., D. C. Shugars, and T. J. Matthews. 1998. Determinants of Human Immunodeficiency Virus Type 1 Resistance to Gp41-derived Inhibitory Peptides. J. Virol. 72:986-993.

Rodriguez-Rosado, R., Briones, C. and Soriano, V. 1999. Introduction of HIV Drug-resistance Testing in Clinical Practice. Aids 13:1007-1014.

Schinazi, R. F., Larder, B. A., and Mellors, J. W. 1999. Mutations in Retroviral Genes Associated with Drug Resistance. Intl. Antiviral News: 7:46-49.

Shi C., and J. W. Mellors. 1997. A Recombinant Retroviral System for Rapid in Vivo Analysis of Human Immunodefiency Virus Type 1 Susceptibility to Reverse Transcriptase Inhibitors. Antimicrob. Agents Chemother 41:2781-2785.

Schurmann D et al. SCH D: antiviral activity of a CCR5 receptor antagonist. Eleventh Conference on Retroviruses and Opportunistic Infections, San Francisco, abstract 140LB, 2004.

Stephenson, J. 1999. New Class of Anti-HIV Drugs. Jama 282:1994.

Who, Unaids/World Health Organization. Report: Aids Epidemic Update: December 1999.

Wild, C., T. Oak, C. Mcdanal, D. Bolognesi, and T. Matthews. 1992. A Synthetic Peptide Inhibitor of HIV Replication: Correlation Between Solution Structure and Viral Inhibition. Proc. Natl. Acad. Sci. USA 89:10537-10541.

Zennou, V., F. Mammamo, S. Paulous, D. Mathez, and F. Calvel. 1998. Loss of Viral Fitness Associated with Multiple Gag and Gag-pol processing Defects in Human Immunodefiency Virus Type 1 Variants Selected for Resistance to Protease Inhibitors in vivo. J. Virol: 72:3300-06.

Ziermann, R., K. Limoli, K. Das, E. Arnold, C. J. Petropoulos, and N. T. Parkin. 2000. A Mutation in HIV-1 Protease, N88s, That Causes in Vitro Hypersensitivity to Amprenavir. J. Virol. 74:4414-4419.

TABLE 1

Cells

| Cell | Receptor |
| --- | --- |
| 5.25 | CXCR4, CD4, CCR5 (not expressed well) BONZO |
| 5.25.Luc4.M7 | CD4, CCR5, BONZO |
| HOS.CD4.CCR5 | CD4, CCR5 |
| HOS.CD4.CXCR4 | CD4,CXCR4 |
| HOS.CD4 | CD4, low level expression of CCR5 and CXCR4 |
| HOS HT4 R5 GFP wt | CD4, CXCR4, CCR5 |
| HOS.CD4.CCR5.GFP.M7#6* | CD4, CXCR4, CCR5 |
| P4.CCR5 | CD4, CXCR4, CCR5 |
| U87.CD4 | CD4 |
| U87.CD4 R5 | CD4, CCR5 |
| U87.CD4 X4 | CD4, CXCR4 |
| MT2 | CD4, CXCR4 |
| MT4 | CD4, CXCR4 |
| PM1 | CD4, CXCR4, CCR5 |
| CEM NKr CCR5 | CD4, CXCR4, CCR5 |

TABLE 2

Representative viruses and reagents

| Viruses | Envelope[a] | Source |
| --- | --- | --- |
| 89.6, SF2 | R5-X4/SI/B | ARRRP[b] |
| 92BR014, 92US076 | R5-X4/SI/B | ARRRP |
| JR-CSF, 91US005 | R5/NSI/B | ARRRP |
| 91US054 | SI/B | ARRRP |
| NL43, MN, ELI | X4/B | ARRRP |
| 92HT599 | X4 | ARRRP |
| 92UG031 | R5/NSI/A | ARRRP |
| 92TH014, 92TH026 | R5/NSI/B | ARRRP |
| 92BR025, 93MW959 | R5/SI/C | ARRRP |
| 92UG035 | R5/NSI/D | ARRRP |
| 92TH022, 92TH023 | R5/NSI/E | ARRRP |
| 93BR020 | R5-X4/SI/F | ARRRP |
| Antibodies | Epitope | SOURCE |
| Mabs 2F5, 1577 | gp41 TM | ARRRP |
| Mabs IG1b12, 2G12, 17b, 48D | gp120 SU | ARRRP |
| Neutralization sera #2, HIV-IG | Polyclonal | ARRRP |
| Entry inhibitors | Target | Source |
| CD4-IG | gp120 SU | Genentech |
| CD4-IGG2 | gp120 SU | Adarc |
| SCD4 (PRO 542) | Sigma | Progenics |
| T20 (DP178) | gp41 TM | Trimeris |
| Rantes, MIPla/b | CCR5 | SIGMA/ARRRP |
| SDFla/b | CXCR4 | SIGMA/ARRRP |
| AMD 3100 | CXCR4 | AnorMed |
| Dextran sulfate, Heparin | Non-specific | Sigma |

[a]R5 (CCR5 co-receptor), X4 (CXCR4 co-receptor)
SI (syncytium inducing), NSI (non-syncytium inducing) A, B, C, D, E, F (envelope clade designation)
[b]AIDS Research and Reference Reagent Program

TABLE 3

Primers Tested for the Amplification of HIV Envelope

| | | SEQ ID NO: |
|---|---|---|
| RT PRIMERS | | |
| Primer 1 | 5'-GGA GCA TTT ACA AGC AGC AAC ACA GC-3' | 16 |
| Primer 2 | 5'-TTC CAG TCA VAC CTC AGG TAC-3' | 17 |
| Primer 3 | 5'-AGA CCA ATG ACT TAY AAG G-3' | 18 |
| 5' PCR PRIMERS | | |
| Primer 4 | 5'-GGG CTC GAG ACC GGT CAG TGG CAA TGA GAG TGA AG-3' | 19 |
| Primer 5 | 5'-GGG CTC GAG ACC GGT GAG CAG AAG ACA GTG GCA ATG A-3' | 20 |
| Primer 6 | 5'-GGG CTC GAG ACC GGT GAG CAG AAG ACA GTG GCA ATG-3' | 21 |
| 3' PCR PRIMERS | | |
| Primer 7 | 5'-GGG TCT AGA ACG CGT TGC CAC CCA TCT TAT AGC AA-3' | 22 |
| Primer 8 | 5'-GGG TCT AGA ACG CGT CCA CTT GCC ACC CAT BTT ATA GC-3' | 23 |
| Primer 9 | 5'-GGG TCT AGA ACG CGT CCA CTT GCC ACC CAT BTT A-3' | 24 |
| Primer 10 | 5'-GAT GGT CTA AGA CGC TGT TCA ATA TCC CTG CCT AAC TC-3' | 25 |

What is claimed is:

1. A method for treating a patient having a human immunodeficiency virus (HIV) infection, comprising
    a) determining or having determined a length of one or more variable regions of an envelope protein of an HIV from a patient or determining or having determined a number of glycosylation sites on the envelope protein;
    b) comparing or having compared the length of the one or more variable regions of the envelope protein of the HIV or the number of glycosylation sites on the envelope protein of the HIV to a length of one or more corresponding variable regions of an envelope protein of a reference HIV or a number of glycosylation sites on the envelope protein of the reference HIV, respectively,
    c) determining or having determined that the HIV is likely to be less susceptible to a CD4 binding site entry inhibitor than the reference HIV if the one or more variable regions of the HIV are longer than corresponding variable regions of the reference HIV or if the HIV has more glycosylation sites than the reference HIV envelope protein; and
    d) treating the patient with an effective amount of the CD4 binding site entry inhibitor if the HIV is determined in step c) to be likely to be susceptible to the CD4 binding site entry inhibitor, or treating the patient with an effective amount of a different inhibitor if the HIV is determined in step c) to be likely to have reduced susceptibility to the CD4 binding site entry inhibitor.

2. The method of claim 1, wherein the CD4 binding site entry inhibitor is PRO542 or monoclonal antibody B12.

3. The method of claim 1, wherein the reference HIV is NL4-3, HXB2, or SF2.

4. The method of claim 1, wherein the HIV has at least one longer variable region than the reference HIV.

5. The method of claim 1, wherein the HIV has at least one more glycosylation site than the reference HIV.

6. The method of claim 1, wherein the HIV has at least one longer variable region and at least one more glycosylation site than the reference HIV.

* * * * *

SEQUENCE LISTING

<160> NUMBER OF SEQ ID NOS: 25

<210> SEQ ID NO 1
<211> LENGTH: 38
<212> TYPE: PRT
<213> ORGANISM: Homo sapiens
<220> FEATURE:
<223> OTHER INFORMATION: Variable Region 1 (V1) of Envelope Protein of
      Clones 3, 20, 47, 48, 18, 17, 35, 11, 24 and 5 isolated from a
      single patient

<400> SEQUENCE: 1

Cys Thr Glu Tyr Asn Ala Thr Tyr Ser Lys Asn Thr Thr Asp Asn
1               5                   10                  15

Thr Thr Val Asn Ala Thr Asp Thr Asn Ile Asn Asp Ser Ile Trp Arg
            20                  25                  30

Gln Val Lys Asn Cys Ser
        35

<210> SEQ ID NO 2
<211> LENGTH: 38
<212> TYPE: PRT
<213> ORGANISM: Homo sapiens
<220> FEATURE:
<223> OTHER INFORMATION: Variable Region 1 (V1) of Envelope Protein
      from Clone 39

<400> SEQUENCE: 2

Cys Thr Glu Tyr Asn Ala Thr Tyr Ser Lys Asp Thr Thr Thr Asp Asn
1               5                   10                  15

Thr Thr Val Asn Ala Thr Asp Thr Asn Ile Asn Asp Ser Ile Trp Arg
            20                  25                  30

Gln Val Lys Asn Cys Ser
        35

<210> SEQ ID NO 3
<211> LENGTH: 59
<212> TYPE: PRT
<213> ORGANISM: Homo sapiens
<220> FEATURE:
<223> OTHER INFORMATION: Variable Region 1 (V1) of Envelope Protein
      from Clones 21 and 26

```
<400> SEQUENCE: 3

Cys Thr Glu Tyr Asn Ala Thr Tyr Ser Lys Asn Thr Thr Val Ser Thr
1               5                  10                  15

Thr Thr Ser Thr Thr Thr Thr Thr Ser Ser Gln Thr Thr Thr Ser Ala
            20                  25                  30

Thr Val Thr Pro Asn Thr Thr Val Asn Pro Thr Thr Ile Asn Ile Asn
        35                  40                  45

Asp Ser Ile Trp Arg Gln Val Lys Asn Cys Ser
    50                  55

<210> SEQ ID NO 4
<211> LENGTH: 59
<212> TYPE: PRT
<213> ORGANISM: Homo sapiens
<220> FEATURE:
<223> OTHER INFORMATION: Variable Region 1 (V1) of Envelope Protein
      from Clone 6

<400> SEQUENCE: 4

Cys Thr Glu Tyr Asn Ala Thr Tyr Ser Lys Asn Thr Thr Val Ser Thr
1               5                  10                  15

Thr Thr Ser Thr Thr Thr Ala Thr Ser Ser Gln Thr Thr Thr Ser Ala
            20                  25                  30

Thr Val Thr Pro Asn Thr Thr Val Asn Pro Thr Thr Ile Asn Ile Asn
        35                  40                  45

Asp Ser Ile Trp Arg Gln Val Lys Asn Cys Ser
    50                  55

<210> SEQ ID NO 5
<211> LENGTH: 59
<212> TYPE: PRT
<213> ORGANISM: Homo sapiens
<220> FEATURE:
<223> OTHER INFORMATION: Variable Region 1 (V1) of Envelope Protein
      from Clone 36

<400> SEQUENCE: 5

Cys Thr Glu Tyr Asn Ala Thr Tyr Ser Lys Asn Thr Thr Val Ser Thr
1               5                  10                  15

Thr Thr Ser Pro Thr Thr Thr Thr Ser Ser Gln Thr Thr Thr Ser Ala
            20                  25                  30

Thr Val Thr Thr Asn Thr Thr Val Asn Pro Thr Thr Ile Asn Ile Asn
        35                  40                  45

Asp Ser Ile Trp Arg Gln Val Lys Asn Cys Ser
    50                  55

<210> SEQ ID NO 6
<211> LENGTH: 59
<212> TYPE: PRT
<213> ORGANISM: Homo sapiens
<220> FEATURE:
<223> OTHER INFORMATION: Variable Region 1 (V1) of Envelope Protein
      from Clone 43

<400> SEQUENCE: 6

Cys Thr Gly Tyr Asn Ala Thr Tyr Ser Lys Asn Thr Thr Val Ser Thr
1               5                  10                  15

Thr Thr Ser Pro Thr Thr Thr Ser Ser Gln Thr Thr Thr Ser Ala
            20                  25                  30

Thr Val Thr Thr Asn Thr Thr Val Asn Pro Thr Thr Ile Asn Ile Asn
        35                  40                  45
```

```
Asp Ser Ile Trp Arg Gln Val Lys Asn Cys Ser
    50                  55
```

```
<210> SEQ ID NO 7
<211> LENGTH: 33
<212> TYPE: PRT
<213> ORGANISM: Homo sapiens
<220> FEATURE:
<223> OTHER INFORMATION: glycosylation sites in V4 region of Envelope
      Protein from Clones 3, 20, 47, 48, 18, 17, 35, 11, and 5

<400> SEQUENCE: 7

Cys Asn Thr Ser Gln Leu Phe Asn Ser Thr Trp Asn Ser Thr Gly Glu
1               5                   10                  15

Asn Asp Ile Ser Glu Ser Asn Ser Thr Glu Gly Ile Ile Thr Leu Pro
            20                  25                  30

Cys
```

```
<210> SEQ ID NO 8
<211> LENGTH: 33
<212> TYPE: PRT
<213> ORGANISM: Homo sapiens
<220> FEATURE:
<223> OTHER INFORMATION: glycosylation sites in V4 region of Envelope
      Protein from Clone 39

<400> SEQUENCE: 8

Cys Asn Thr Ser Gln Leu Phe Asn Ser Thr Trp Asn Ser Thr Gly Glu
1               5                   10                  15

Asn Asp Ile Ser Glu Ser Asn Ser Thr Glu Gly Ile Ile Ala Leu Pro
            20                  25                  30

Cys
```

```
<210> SEQ ID NO 9
<211> LENGTH: 33
<212> TYPE: PRT
<213> ORGANISM: Homo sapiens
<220> FEATURE:
<223> OTHER INFORMATION: glycosylation sites in V4 region of Envelope
      Protein of Clone 24

<400> SEQUENCE: 9

Cys Asn Thr Ser Gln Leu Phe Asn Ser Thr Trp Asn Ser Thr Gly Glu
1               5                   10                  15

Asn Gly Ile Ser Glu Ser Asn Ser Thr Glu Gly Ile Ile Thr Leu Pro
            20                  25                  30

Cys
```

```
<210> SEQ ID NO 10
<211> LENGTH: 33
<212> TYPE: PRT
<213> ORGANISM: Homo sapiens
<220> FEATURE:
<223> OTHER INFORMATION: glycosylation sites in V4 region of Envelope
      Protein from Clones 21, 26 and 6

<400> SEQUENCE: 10

Cys Asn Thr Ser Gln Leu Phe Asn Ser Thr Trp Asn Ser Thr Glu Glu
1               5                   10                  15

Asn Asp Ile Ser Glu Ser Asn Ser Thr Arg Gly Asn Ile Thr Leu Pro
            20                  25                  30

Cys
```

```
<210> SEQ ID NO 11
<211> LENGTH: 36
<212> TYPE: PRT
<213> ORGANISM: Homo sapiens
<220> FEATURE:
<223> OTHER INFORMATION: glycosylation sites in V4 region of Envelope
      Protein from Clones 36 and 43

<400> SEQUENCE: 11

Cys Asn Thr Ser Gln Leu Phe Asn Ser Thr Trp Leu Gly Asn Ser Thr
1               5                   10                  15

Leu Glu Asn Asp Thr Thr Thr Glu Ser Asn Ser Thr Arg Gly Asn Ile
            20                  25                  30

Thr Leu Pro Cys
        35

<210> SEQ ID NO 12
<211> LENGTH: 20
<212> TYPE: PRT
<213> ORGANISM: Homo sapiens
<220> FEATURE:
<223> OTHER INFORMATION: glycosylation sites in V5 region of Envelope
      Protein from Clones 3, 20, 39, 47, 48, 18, 17, 35, 11, 24 and 5

<400> SEQUENCE: 12

Gly Gly Asn Asp Gly Ser Asn Asn Thr Glu Ile Phe Arg Pro Gly Gly
1               5                   10                  15

Gly Asn Met Lys
            20

<210> SEQ ID NO 13
<211> LENGTH: 24
<212> TYPE: PRT
<213> ORGANISM: Homo sapiens
<220> FEATURE:
<223> OTHER INFORMATION: glycosylation sites in V5 region of Envelope
      Protein from Clones 21 and 26

<400> SEQUENCE: 13

Gly Gly Lys Lys Gly Asn Glu Thr Asp Gly Asn Glu Thr Glu Ile Phe
1               5                   10                  15

Arg Pro Gly Gly Gly Asp Met Arg
            20

<210> SEQ ID NO 14
<211> LENGTH: 24
<212> TYPE: PRT
<213> ORGANISM: Homo sapiens
<220> FEATURE:
<223> OTHER INFORMATION: glycosylation sites in V5 region of Envelope
      Protein from Clone 6

<400> SEQUENCE: 14

Gly Gly Lys Lys Gly Asn Glu Thr Asp Gly Asn Gly Thr Glu Ile Phe
1               5                   10                  15

Arg Pro Gly Gly Gly Asp Met Arg
            20

<210> SEQ ID NO 15
<211> LENGTH: 24
<212> TYPE: PRT
<213> ORGANISM: Homo sapiens
<220> FEATURE:
<223> OTHER INFORMATION: glycosylation sites in V5 region of Envelope
```

Protein from Clones 36 and 43

<400> SEQUENCE: 15

Gly Gly Lys Lys Gly Asn Glu Thr Asp Gly Asn Glu Thr Glu Ile Phe
1               5                   10                  15

Arg Pro Gly Gly Gly Asn Met Arg
            20

<210> SEQ ID NO 16
<211> LENGTH: 26
<212> TYPE: DNA
<213> ORGANISM: Artificial Sequence
<220> FEATURE:
<223> OTHER INFORMATION: RT primer-1 for the amplification of HIV
      envelope protein

<400> SEQUENCE: 16
ggagcattta caagcagcaa cacagc                                          26

<210> SEQ ID NO 17
<211> LENGTH: 21
<212> TYPE: DNA
<213> ORGANISM: Artificial Sequence
<220> FEATURE:
<223> OTHER INFORMATION: RT primer-2 for the amplification of HIV
      envelope protein

<400> SEQUENCE: 17
ttccagtcav acctcaggta c                                               21

<210> SEQ ID NO 18
<211> LENGTH: 19
<212> TYPE: DNA
<213> ORGANISM: Artificial Sequence
<220> FEATURE:
<223> OTHER INFORMATION: RT primer-3 for the amplification of HIV
      envelope protein

<400> SEQUENCE: 18
agaccaatga cttayaagg                                                  19

<210> SEQ ID NO 19
<211> LENGTH: 35
<212> TYPE: DNA
<213> ORGANISM: Artificial Sequence
<220> FEATURE:
<223> OTHER INFORMATION: 5 prime PCR primer-4 for the amplification of
      HIV envelope protein

<400> SEQUENCE: 19
gggctcgaga ccggtcagtg gcaatgagag tgaag                                35

<210> SEQ ID NO 20
<211> LENGTH: 37
<212> TYPE: DNA
<213> ORGANISM: Artificial Sequence
<220> FEATURE:
<223> OTHER INFORMATION: 5 prime PCR primer-5 for the amplification of
      HIV envelope protein

<400> SEQUENCE: 20
gggctcgaga ccggtgagca gaagacagtg gcaatga                              37

<210> SEQ ID NO 21
<211> LENGTH: 36
<212> TYPE: DNA

```
<213> ORGANISM: Artificial Sequence
<220> FEATURE:
<223> OTHER INFORMATION: 5 prime PCR primer-6 for the amplification of
      HIV envelope protein

<400> SEQUENCE: 21
gggctcgaga ccggtgagca gaagacagtg gcaatg                                36

<210> SEQ ID NO 22
<211> LENGTH: 35
<212> TYPE: DNA
<213> ORGANISM: Artificial Sequence
<220> FEATURE:
<223> OTHER INFORMATION: 3 prime PCR primer-7 for the amplification of
      HIV envelope protein

<400> SEQUENCE: 22
gggtctagaa cgcgttgcca cccatcttat agcaa                                 35

<210> SEQ ID NO 23
<211> LENGTH: 38
<212> TYPE: DNA
<213> ORGANISM: Artificial Sequence
<220> FEATURE:
<223> OTHER INFORMATION: 3 prime PCR primer-8 for the amplification of
      HIV envelope protein

<400> SEQUENCE: 23
gggtctagaa cgcgtccact tgccacccat bttatagc                              38

<210> SEQ ID NO 24
<211> LENGTH: 34
<212> TYPE: DNA
<213> ORGANISM: Artificial Sequence
<220> FEATURE:
<223> OTHER INFORMATION: 3 prime PCR primer-9 for the amplification of
      HIV envelope protein

<400> SEQUENCE: 24
gggtctagaa cgcgtccact tgccacccat btta                                  34

<210> SEQ ID NO 25
<211> LENGTH: 38
<212> TYPE: DNA
<213> ORGANISM: Artificial Sequence
<220> FEATURE:
<223> OTHER INFORMATION: 3 prime PCR primer-10 for the amplification
      of HIV envelope protein

<400> SEQUENCE: 25
gatggtctaa gacgctgttc aatatccctg cctaactc                              38
```